(12) United States Patent
Cary et al.

(10) Patent No.: US 12,285,463 B2
(45) Date of Patent: Apr. 29, 2025

(54) MODULATION OF TUMOR IMMUNITY BY PROTEIN-MEDIATED $O_2$ DELIVERY

(71) Applicant: Omniox, Inc., San Carlos, CA (US)

(72) Inventors: Stephen P. L. Cary, San Mateo, CA (US); Ana Krtolica, San Francisco, CA (US); Natacha Le Moan, San Francisco, CA (US); Jonathan A Winger, Oakland, CA (US); Kevin G. Leong, Millbrae, CA (US)

(73) Assignee: Omniox, Inc., San Francisco, CA (US)

( * ) Notice: Subject to any disclaimer, the term of this patent is extended or adjusted under 35 U.S.C. 154(b) by 0 days.

(21) Appl. No.: 17/547,748

(22) Filed: Dec. 10, 2021

(65) Prior Publication Data

US 2022/0160823 A1 May 26, 2022

Related U.S. Application Data

(63) Continuation of application No. 15/558,957, filed as application No. PCT/US2016/022981 on Mar. 17, 2016, now abandoned.

(60) Provisional application No. 62/134,523, filed on Mar. 17, 2015.

(51) Int. Cl.
| | | |
|---|---|---|
| A61K 38/16 | (2006.01) | |
| A61K 39/39 | (2006.01) | |
| A61K 39/395 | (2006.01) | |
| A61K 45/06 | (2006.01) | |
| A61K 47/60 | (2017.01) | |
| A61P 35/00 | (2006.01) | |
| C07K 16/28 | (2006.01) | |
| A61N 5/10 | (2006.01) | |

(52) U.S. Cl.
CPC ............ *A61K 38/164* (2013.01); *A61K 39/39* (2013.01); *A61K 45/06* (2013.01); *A61K 47/60* (2017.08); *A61P 35/00* (2018.01); *A61N 5/10* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 4,873,192 A | 10/1989 | Kunkel | |
| 5,248,766 A | 9/1993 | Nelson et al. | |
| 5,295,944 A | 3/1994 | Teicher et al. | |
| 5,679,638 A | 10/1997 | Teicher et al. | |
| 5,776,898 A | 7/1998 | Teicher et al. | |
| 5,981,710 A | 11/1999 | Hai et al. | |
| 6,432,918 B1 | 8/2002 | Winslow | |
| 6,974,795 B2 | 12/2005 | Winslow et al. | |
| 7,989,593 B1 | 8/2011 | Wong et al. | |
| 8,106,011 B1 | 1/2012 | Wong et al. | |
| 8,404,631 B2 | 3/2013 | Cary et al. | |
| 8,404,632 B2 | 3/2013 | Cary et al. | |
| 8,742,073 B2 | 6/2014 | Wong et al. | |
| 9,493,526 B2 | 11/2016 | Cary et al. | |
| 9,493,527 B2 | 11/2016 | Cary et al. | |
| 10,385,116 B2 | 8/2019 | Kapp et al. | |
| 10,766,947 B2 | 9/2020 | Kapp et al. | |
| 11,117,952 B2 | 9/2021 | Kapp et al. | |
| 2002/0142957 A1 | 10/2002 | Hepler et al. | |
| 2005/0176108 A1* | 8/2005 | Kim | A61K 47/60 530/391.1 |
| 2010/0183545 A1 | 7/2010 | Puri | |
| 2011/0243849 A1 | 10/2011 | Marietta et al. | |
| 2011/0288023 A1 | 11/2011 | Kamei et al. | |
| 2013/0052232 A1 | 2/2013 | Wong et al. | |
| 2013/0177641 A1 | 7/2013 | Ghoroghchian | |
| 2014/0255477 A1 | 9/2014 | Ghoroghchian | |
| 2014/0363496 A1 | 12/2014 | Ghoroghchian | |
| 2015/0210769 A1* | 7/2015 | Freeman | A61P 13/08 435/254.2 |
| 2015/0273024 A1 | 10/2015 | Cary et al. | |
| 2016/0077096 A1* | 3/2016 | Dietz | A61N 5/10 424/85.1 |
| 2016/0185839 A1 | 6/2016 | Kapp et al. | |
| 2017/0267732 A1 | 9/2017 | Cary et al. | |
| 2017/0360706 A1 | 12/2017 | Ghoroghchian | |
| 2017/0361126 A1 | 12/2017 | Ghoroghchian | |

(Continued)

FOREIGN PATENT DOCUMENTS

| | | |
|---|---|---|
| CN | 101495506 A | 7/2009 |
| JP | 2011168521 A | 9/2011 |

(Continued)

OTHER PUBLICATIONS

Hernandez-Ledesma (Peptides, vol. 30, p. 426-430, 2009) (Year: 2009).*
Serwer (Neuro-Oncology, vol. 15, Supplement 3, p. iii57-iii58, Abstract ET-088, 2013) (Year: 2013).*
Lee (Int. J. Hyperthermia, vol. 26, No. 3, p. 232-246, 2010) (Year: 2010).*
Komenaka et al., Clinics in Dermatology, 2004, vol. 22, p. 251-265 (Year: 2004).*
Evans et al. (Q. J. Med 1999: 92: 299-307) (Year: 1999).*
Schiffman et al. (The New England Journal of Medicine, Vo. 353, No. 20, p. 2101-2104, 2005) (Year: 2005).*
Cuzick et al. (The Lancet, vol. 361, p. 296-300, 2003) (Year: 2003).*

(Continued)

*Primary Examiner* — Laura B Goddard
(74) *Attorney, Agent, or Firm* — Mintz, Levin, Cohn, Ferris, Glovsky and Popeo, P.C.

(57) ABSTRACT

The invention provides methods to modulate hypoxia-mediated tumor immunity by administration of an $O_2$ carrier polypeptide (e.g., an H-NOX protein). The methods of the invention target both hypoxia inducible factor 1 alpha (HIF-1α) pathways and non-HIF-1α pathways of tumor immunity. Such methods are useful in the treatment of a wide variety of cancers and may be used alone or in combination with other anti-cancer therapies.

18 Claims, 16 Drawing Sheets

Specification includes a Sequence Listing.

(56) References Cited

U.S. PATENT DOCUMENTS

| | | |
|---|---|---|
| 2018/0243364 A1 | 8/2018 | Cary et al. |
| 2020/0017574 A1 | 1/2020 | Kapp et al. |
| 2022/0048977 A1 | 2/2022 | Kapp et al. |

FOREIGN PATENT DOCUMENTS

| | | | |
|---|---|---|---|
| RU | 2475252 C1 | 2/2013 | |
| WO | WO-1992/020369 A1 | 11/1992 | |
| WO | WO-1999/003484 A1 | 1/1999 | |
| WO | WO-2006/091542 A2 | 8/2006 | |
| WO | WO-2007/079096 A2 | 7/2007 | |
| WO | WO-2007/133811 A2 | 11/2007 | |
| WO | WO-2007/139767 A2 | 12/2007 | |
| WO | WO-2007/139791 A2 | 12/2007 | |
| WO | WO-2008/034608 A1 | 3/2008 | |
| WO | WO-2008/074865 A1 | 6/2008 | |
| WO | WO-2011/149602 A1 | 12/2011 | |
| WO | WO-2012/094679 A2 | 7/2012 | |
| WO | WO-2013/032828 A2 | 3/2013 | |
| WO | WO-2014107171 A1 * | 7/2014 | ........... A61K 38/164 |
| WO | WO-2014/193898 A1 | 12/2014 | |
| WO | WO-2016/022805 A1 | 2/2015 | |
| WO | WO-2016/090111 A1 | 6/2016 | |

OTHER PUBLICATIONS

U.S. Appl. No. 62/088,199, filed Dec. 5, 2014, Ghoroghchian.
U.S. Appl. No. 62/127,557, filed Mar. 3, 2015, Ghoroghchian.
U.S. Appl. No. 15/984,275, filed May 18, 2018, Cary et al.
Abdelwahab et al., 2011, "Intracranial Implantation with Subsequent 3D in Vivo Bioluminescent Imaging of Murine Gliomas," J. Vis. Exp. (57):e3403, doi:10.3791/3403 (epub.). 8 pages.
El Andaloussi et al., 2006, "Prolongation of survival following depletion of CD4+CD25+ regulatory T cells in mice with experimental brain tumors," J. Neurosurg., 105:430-437. 8 pages.
Grossman et al., 2014, "Combination of anti-VEGF therapy and temozolomide in two experimental human glioma models," J. Neurooncol., 116:59-65. 7 pages.
Highlights of Prescribing Information and Full Prescribing Information for "Bavencio (avelumab) injection," revision Nov. 2020. 35 pages.
Highlights of Prescribing Information and Full Prescribing Information for "Keytruda (pembrolizumab) injection," revision Jan. 2020. 91 pages.
Highlights of Prescribing Information and Full Prescribing Information for "Opdivo (nivolumab) injection," revision Nov. 2020. 38 pages.
Highlights of Prescribing Information and Full Prescribing Information for "Tecentriq (atezolizumab) injection," revision Dec. 2020. 68 pages.
Kjaergaard et al., 2000, "Therapeutic Efficacy of OX-40 Receptor Antibody Depends on Tumor Immunogenicity and Anatomic Site of Tumor Growth," Cancer Res., 60:5514-5521. 9 pages.
Kjaergaard et al., 2005, "Active immunotherapy for advanced intracranial murine tumors by using dendritic cell-tumor cell fusion vaccines," J. Neurosurg., 103:156-164. 9 pages.
Leong et al., 2018, "Reversal of advanced colitis-associated colon cancer by OMX, a novel oxygen carrier that immunosensitizes the hypoxic tumor microenvironment," Poster, AACR Annual Meeting, Apr. 14-18, 2018. 1 page.
Momtaz et al., 2014, "Immunologic checkpoints in cancer therapy: focus on the programmed death-1 (PD-1) receptor pathway," Pharmacogenomics and Personalized Med., (7):357-365. 9 pages.
Udono, H., 2013, "Cancer immunotherapy with blocking of immune checkpoints," J. of Okayama Medical Association, 125(1):13-18 (in Japanese with English translation). 18 pages total.
Ueda et al., 2009, "Systemic Inhibition of Transforming Growth Factor-0 in Glioma-Bearing Mice Improves the Therapeutic Efficacy of Glioma-Associated Antigen Peptide Vaccines," Clin. Cancer Res., 15(21):6551-6559. 10 pages.
Walsh et al., 2014, "The Clinical Importance of Assessing Tumor Hypoxia: Relationship of Tumor Hypoxia to Prognosis and Therapeutic Opportunities," Antioxidants & Redox Signaling, 21(10):1516-1554). 39 pages.
Zhu et al., 2011, "Systemic delivery of neutralizing antibody targeting CCL2 for glioma therapy," J. Neurooncol., 104:83-92. 10 pages.
Response to Non-Final Office Action dated Apr. 18, 2018, filed in U.S. Appl. No. 14/759,635 (with Declaration of Stephen Cary Under 37 C.F.R. § 1.132 and Declaration of Nicolas Butowski Under 37 C.F.R. § 1.132); 51 pages.
Response to Final Office Action dated Nov. 1, 2018, filed in U.S. Appl. No. 14/759,635 (with Second Declaration of Stephen P.L. Cary Under 37 C.F.R. § 1.132 and Exhibits A-E); 28 pages.
Hu et al., 2008, "Allostery in recombinant soluble guanylyl cyclase from Manduca sexta," J. Biol. Chem., 283(30):20968-20977.
Le Moan et al., Jul. 2018, "The oxygen carrier omx restores antitumor immunity and cures tumors as a single agent or in combination with checkpoint inhibitors in an intracranial glioblastoma mouse model," Proceedings of the American Association for Cancer Research (AACR) Annual Meeting, Apr. 14-18, 2018, Chicago, Illinois; Cancer Res., 78(13 Suppl.): Abstract No. 4726A; published online Mar. 14, 2018.
Le Moan et al., 2018, "The oxygen carrier omx restores antitumor immunity and cures tumors as a single agent or in combination with anti-PD-1 in an intracranial glioblastoma mouse model," American Association for Cancer Research (AACR) Annual Meeting, Apr. 17, 2018, Chicago, Illinois, Poster.
Le Moan et al., 2018, "Immunosensitization of the hypoxic tumor microenvironment by the oxygen carrier OMX leads to tumor cures in mouse models of intracranial glioblastoma and advanced colitis-associated colon cancer," Keystone Symposia, published online on Mar. 23, 2018, [online], [retrieved on Jul. 26, 2019]. Retrieved from the Internet <URL:https://virtual.keystonesymposia.org/ks/articles/2518/view >.
Le Moan et al., 2018, "Immunosensitization of the hypoxic tumor microenvironment by the oxygen carrier OMX leads to tumor cures in mouse models of intracranial glioblastoma and advanced colitis-associated colon cancer," Keystone Symposia, Mar. 25, 2018, Whistler, Canada, Poster P469.
Le Moan et al., 2018, Abstract TMIC-15, "OMX is a tumor microenvironment modifier that restores anti-tumor immunity and improves anti-tumor efficacy by reducing tumor hypoxia in intracranial glioblastoma mouse model," Neuro-Oncology, 20(Suppl 6): vi259; published online Nov. 5, 2018.
Le Moan, 2018, "OMX is a tumor microenvironment modifier that restores anti-tumor immunity and improves anti-tumor efficacy by reducing tumor hypoxia in intracranial glioblastoma mouse model," Society for Neuro-Oncology Conference, New Orleans, Louisiana, Nov. 16, 2018, E-Talk (7 pages).
Leong et al., 2018, "Reversal of advanced colitis-associated colon cancer by OMX, a novel oxygen carrier that immunosensitizes the hypoxic tumor microenvironment," Proceedings of the American Association for Cancer Research (AACR) Annual Meeting, Apr. 14-18, 2018, Chicago, Illinois; Cancer Res., 78(13 Suppl.): Abstract No. 1744; published online Mar. 14, 2018.
Leong et al., 2018, "Reversal of advanced colitis-associated colon cancer by OMX, a novel oxygen carrier that immunosensitizes the hypoxic tumor microenvironment," American Association for Cancer Research (AACR) Annual Meeting, Apr. 16, 2018, Chicago, Illinois, Poster.
Ma et al., 2008, "PAS-mediated dimerization of soluble guanylyl cyclase revealed by signal transduction histidine kinase domain crystal structure," J. Biol. Chem., 283(2):1167-1178.
Arora et al., 2012, "Nitric oxide regulated two-component signaling in Pseudoalteromonas atlantica," Biochem Biophys Res Commun., 421(3):521-526.
Behrends et al., 2001, "Abstract No. 165: The beta2 subunit is the first example of a mammalian homodimeric nitric oxide-sensitive guanylyl Cyclase," Naunyn-Schmiedeberg's Archives of Pharmacology, 363(4 Supplement):R45.

(56) References Cited

OTHER PUBLICATIONS

Bhardwaj et al., 2007, "Domain Organization and Polarity of Tail Needle GP26 in the Portal Vertex Structure of Bacteriophage P22," J Mol Biol, 371:374-387.
Bhardwaj et al., 2008, "Foldon-guided Self-assembly of Ultrastable Protein Fibers," Protein Sci, 17:1475-1485.
Bobofchak et al., 2003, "A Recombinant Polymeric Hemoglobin with Conformational, Functional, and Physiological Characteristics of an in Vivo O2 Transporter," Am. J. Physiol Heart Circ., 285(2):H549-H561.
Boon et al., 2005, "A Molecular Basis for NO Selectivity in Soluble Guanylate Cyclase," Nature Chemical Biology 1(1):53-59.
Boon et al., 2005, "Ligand Discrimination in Soluble Guanylate Cyclase and the H-NOX Family of Heme Sensor Proteins," Curr. Opin. Chem. Biol., 9(5):441-446.
Boon et al., 2005, "Ligand Specificity of H-NOX Domains: From sGC to Bacterial NO Sensors," J. Inorg. Biochem., 99(4):892-902.
Boon et al., 2006, "Nitric Oxide Binding to Prokaryotic Homologs of the Soluble Guanylate Cyclase {1}1 H-NOX Domain," J. Biol. Chem., 281 (31):21892-21902.
Boon et al., 2006, "Sensitive and selective detection of nitric oxide using an H-NOX domain," J Am Chem Soc., 128(31):10022-10023.
Borlongan et al., 1988, "Transplantation of Cryopreserved Human Embryonal Carcinoma-Derived Neuron (NT2N Cells) Promotes Functional Recovery in Ischemic Rats," Experimental Neurology, 149:310-321.
Boudko et al., 2002, "Domain Organization, Folding and Stability of Bacteriophage T4 Fibritin, A Segmented Coiled-Coil Protein," Eur J. Biochem., 269:833-841.
Brown et al., 2010, "Stereotactic Ablative Radiotherapy Should be Combined with a Hypoxic Cell Radiosensitizer," Int J Radiat Oncol Biol Phys, 78:323-327.
Brown et al., 2010, "The remarkable yin and yang of tumour hypoxia," Int J Radiat Biol., 86(11):907-917.
Capece et al., 2008, "Dynamical characterization of the heme NO oxygen binding (HNOX) domain. Insight into soluble guanylate cyclase allosteric transition", Biochemistry, 47(36):9416-9427.
Cary et al., 2005, "Tonic and Acute Nitric Oxide Signaling Through Soluble Guanylate Cyclase is Mediated by Nonheme Nitric Oxide, ATP, and GTP," Proc. Natl. Acad. Sci. USA, 102(37):13064-13069.
Cary et al., 2006, "Nitric Oxide Signaling: No Longer Simply on or off," Trends Bio. Sci., 31(4):231-239.
Cary et al., 2011, "H-Nox: A nitric-oxide neutral, tunable oxygen delivery technology," Artificial Cells, Blood Substitutes and Biotechnology 40.3 (Abstracts from XIII International Symposium on Blood Substitutes and Oxygen Therapeutics):206.
Cary, 2012, Project No. 1R43NS076272-01A1 "Reducing Brain Injury After Focal Ischemia Using a Nitric Oxide-Neutral Oxygen CA," retrieved from www.sbir.gov/print/sbirsearch/detail/400994 on Nov. 14, 2018 (3 pages).
Chaturvedi et al., 2014, "Hypoxia-inducible factor-dependent signaling between triple-negative breast cancer cells and mesenchymal stem cells promotes macrophage recruitment," Proc Natl Acad Sci USA, 111(20):E2120-2129.
Choi et al., 2007, "Renal clearance of quantum dots," Nat Biotechnol., 25(10):1165-1170.
Codo et al., 2014, "MicroRNA-mediated down-regulation of NKG2D ligands contributes to glioma immune escape," Oncotarget, 5(17):7651-7662.
Corzo et al., 2010, "HIF-1a regulates function and differentiation of myeloid-derived suppressor cells in the tumor microenvironment," J Exp Med., 207(11):2439-2453.
Demaria et al., 2005, Combining radiotherapy and immunotherapy: a revived partnership. Int J Radiat Oncol Biol Phys. 63(3):655-666.
Dente, et al., 1985, "Chapter 5: The pEMBL Family of Singlestranded Vectors" DNA Cloning, vol. 1—A Practical Approach, Glover, Ed. IRL Press, pp. 101-107.
Derbyshire et al., 2011, "Probing Domain Interactions in Soluable Guanylate Cyclase," Biochemistry 50(20):4281-4290.

Dmochowski et al., 2000, "Enantiomeric Discrimination of Ru-Substmtes by Cytochrome P540cam," Journal of Inorganic Biochemistry, 81:221-228.
Dreher et al., 2006, "Tumor vascular permeability, accumulation, and penetration of macromolecular drug carriers," J Natl Cancer Inst., 98(5):335-344.
Du et al., 2008, "Improvement of Thermostability of Recombinant Collagen-like Protein by Incorporating a Foldon Sequence," Appl Microbiol Biotechnol, 79:195-202.
Efimov et al., 1994 "Fibritin Encoded by Bacteriophage T4 Gene wac has a Parallel Triple-Stranded a-Helical Coiled-coil Structure," J. Mol. Biol., 242:470-486.
Fang et al., 2009, "Hypoxia-inducible factors 1 and 2 are important transcriptional effectors in primary macrophages experiencing hypoxia," Blood, 114(4):844-859.
Guarnone et al., 1995, "Performance Characteristics of Hemox-Analyzer for Assessment of the Hemoglobin Dissociation Curve," Haematologica, 80(5):426-430.
Guthe et al., 2004, "Very Fast Folding and Association of a Trimerization Domain from bacteriophage T4 Fibritin," J. Mol. Biol., 337:905-915.
Hatfield et al., 2015, "Immunological mechanisms of the antitumor effects of supplemental oxygenation," Sci Transl Med., 7(277):277ra30.
Heller et al., 1999, "Conformational Stability of Lyophilized PEGylated Proteins in a Phase-Separating System," Journal of Pharmaceutical Sciences, 88(1):58-64.
Huang et al., 2007, "Ligand Binding and Inhibition of an Oxygen-Sensitive Soluble Guanylate Cyclase, Gyc-88E, from Drosphila," Biochemistry, 46:15115-15122.
International Search Report mailed Sep. 26, 2016, for International Application No. PCT/US2016/022981, filed on Mar. 17, 2016 (6 pages).
Irwin et al., 2008, "Polymerized bovine hemoglobin decreases oxygen delivery during normoxia," Am. J. Physiol. Heart Circ. Physiol., 295:H1090-H1099.
Ito et al, 2011, "Trimerization of murine TNF ligand family member Light increases the cytotoxic activity against the FM3A mammary carcinoma cell line," Appl Microbiol Biotechnol., 90(5):1691-1699.
Iyer et al., 2003, "Ancient Conserved Domains Shared by Animal Soluble Guanylyl Cyclases and Bacterial Signaling Proteins," BMC Genomics 4(1):5 (8 pages).
Jones et al., 1990, "A Rapid Method for Site-Specific Mutagenesis and Directional Subcloning by Using the Polymerase Chain Reaction to Generate Recombinant Circles," Biotechniques, 8(2):178-183.
Jones et al., 1991 "A Rapid Method for Recombination and Site-Specific Mutagenesis by Placing Homologous Ends on DNA Using Polymerase Chain Reaction," Biotechniques, 10(1):62-66.
Kallet et al., 2013, "Hyperoxic acute lung injury," Respir Care, 58(1):123-141.
Karow et al., 2004, "Spectroscopic Characterization of the Soluble Guanylate Cyclase-Like Heme Domains From Vibrio cholera and Thermoanaerobacter Tengcongensis," Biochemistry 43(31):10203-10211.
Karow et al., 2005, "Characterization of Functional Heme Domains from Soluble Guanylate cyclase," Biochemistry, 44(49):16266-16274.
Keating et al., 2015, "Epigenetics and Metabolism," Circulation Research, 116:715-736.
Koglin et al., 2001, "Nitric oxide activates the beta 2 subunit of soluble guanylyl cyclase in the absence of a second subunit," J Biol Chem., 276(33):30737-30743.
Krtolica et al., 2014, "Abstract No. ET-31: Radiosensitization By OMX-4.80p, A Pegylated H-Nox Oxygen Carrier That Penetrates and Oxygenates Hypoxic Tumors, In Preclinical Models of Glioblastoma and Other Hypoxic Cancers," Neuro-Oncology 16 (suppl. 5): v86.
Krtolica et al., 2014, "Abstract No. 02.04: Treatment With OMX-4.80, A Tumor-Penetrating Tunable Oxygen Carrier, Reduces Tumor Hypoxia and Dramatically Enhances Radiation Therapy in Intracranial Models of Glioblastoma," Neuro-Oncology 16 (suppl. 2):ii3-ii4.
Krtolica, 2013, Project 1R43CA165629-01A1 "Improving Chemotherapy with a Novel Oxygen-delivery Protein" National Institute of Health (1 page).

(56) References Cited

OTHER PUBLICATIONS

Kunkel, 1985, "Rapid and Efficient Site-Specific Mutagenesis Without Phenotypic Selection," Proc. Natl. Acad. Sci. USA, 82(2):488-492.

Kunkel, 1987, "Rapid and Efficient Site-Specific Mutagenesis Without Phenotypic Selection," Methods Enzymol, 154:367-382.

Laquintana et al., 2009, "New strategies to deliver anticancer drugs to brain tumors," Expert Opin Drug Deliv., (10):1017-1032.

Le Moan et al., 2013, "Abstract No. ET-055: Targeting Hypoxia in Glioblastoma Multiforme with a Novel Oxygen Carrier Protein," Neuro-Oncology 15 iii37-iii61.

Le Moan et al., 2013, "Targeting Hypoxia in Glioblastoma Multiforme with a Novel Oxygen Carrier Protein," Neuro-Oncology 15 (suppl. 3):iii50-Poster.

Le Moan et al., 2017, "A new paradigm in protecting ischemic brain: preserving the neurovascular unit before reperfusion," in Book titled Neuroprotective Therapy for Stroke and Ischemic Disease, Chapter 27, Lapchak & Zhang (des.), Springer International Publishing Switzerland, pp. 641-664.

Le Moan et al., 2018, "The oxygen carrier OMX restores anti-tumor immunity and when combined with checkpoint inhibitors improves anti-tumor efficacy in orthotopic and subcutaneous tumor models," Keystone Symposia & Digitell, Inc., Abstract (Identification: 2032).

Lee et al., 2010, "Hypoxia-driven immunosuppression: a new reason to use thermal therapy in the treatment of cancer?," Int J Hyperthermia, 26(3):232-246.

Letarov et al., 1999, "The Carboxy-Terminal Domain Initiates Trimerization of Bacteriophage T4 Fibritin," Biochemistry (Most), 64:817-823.

Lewis et al., 2007, "Inflammation and breast cancer. Microenvironmental factors regulating macrophage function in breast tumours: hypoxia and angiopoietin-2," Breast Cancer Res., 9(3):209 (4 pages).

Li et al., 1988, "Cloning of the *Escherichia coli* K-12 hemB Gene," Journal of Bacteriology, 170:1021-1025.

Mammen et al., 1998, "Polyvalent Interactions in Biological Systems: Implications for Design and Use of Multivalent Ligands and Inhibitors," Angew Chem Int Ed Engl., 37(20):2754-2794.

Migata et al., 1997, "Blood Volume and Cardiac Index in Rats After Exchange Transfusion with Hemoglobin-based Oxygen Carriers," J. Appl. Physiol., 82(6):1995-2002.

Mimura et al., 2011, "Pathophysiological response to hypoxia—from the molecular mechanisms of malady to drug discovery: epigenetic regulation of the hypoxic response via hypoxia-inducible factor and histone modifying enzymes," J Pharmacol Sci., 115(4):453-458.

Moeller et al., 2007, "Hypoxia and Radiotherapy: Opportunities for Improved Outcomes in Cancer Treatment," Cancer and Metastasis Rev., 26:241-248.

Morton et al., 2003, "MsGC-beta3 forms active homodimers and inactive heterodimers with NO-sensitive soluble guanylyl cyclase subunits," The Journal of Experimental Biology, 206 (Pt 6):937-947.

Nakamaye et al., 1986, "Inhibition of Restriction Endonuclease Nci I Cleavage by Phosphorothioate Groups and its Application to Oligonucleotide-Directed Mutagenesis," Nucleic Acids Res., 14(24):9679-9698.

Nemoto et al., 2006, "Salvage of focal cerebral ischemic damage by transfusion of high O2-affinity recombinant hemoglobin polymers in mouse," J. Appl. Physiol., 100:1688-1691.

Noguchi et al., 1998, "Early phase tumor accumulation of macromolecules: a great difference in clearance rate between tumor and normal tissues," Jpn J Cancer Res., 89(3):307-314.

Noman et al., 2014, "PD-L1 is a novel direct target of HIF-la, and its blockade under hypoxia enhanced MDSC-mediated T cell activation," J Exp Med., 211(5):781-790.

Ohta et al., 2006, "A2A adenosine receptor protects tumors from antitumor T cells," Proc Natl Acad Sci USA, 103(35):13132-13137.

Ouellet et al., 2002, "Truncated Hemoglobin HbN Protects Mycobacterium Bovis from Nitric Oxide," Proc. Natl. Acad. Sci. USA, 99(9):5902-5907.

Overgaard, 2007, "Hypoxic radiosensitization: adored and ignored," J Clin Oncol., 25(26):4066-4074.

Ozawa et al., 2010, "Establishing Intracranial Brain Tumor Xenografts with Subsequent Analysis of Tumor Growth and Response to Therapy Using Bioluminescence Imaging," J Vis Exp., 41:e1986.

Papanikolopoulou et al., 2004, "Adenovirus Fibre Shaft Sequences Fold into the Native Triple Beta-Spiral Fold when N-terminally Fused to the Bacteriophage T4 Fibritin Foldon Trimerisation Motif," J Mol Biol, 342:219-227.

Papanikolopoulou et al., 2004, "Formation of Highly Stable Chimeric Trimers by Fusion of an Adenovirus Fiber Shaft Fragment with the Foldon Domain of Bacteriophage T4 Fibritin," J. Bio. Chem., 279:8991-8998.

Pellicena et al., 2004, "Crystal Structure of an Oxygen-Binding Heme Domain Related to Soluble Guanylate Cyclases," Proc. Natl. Acad. Sci. USA, 101(35):12854-12859.

Phillips et al., 2006, "Molecular Subclasses of High-Grade Glioma Predict Prognosis, Delineate a Pattern of Disease Progression, and Resemble Stages in Neurogenesis," Cancer Cell, 9(3):157-173.

Rockwell et al., 2009, "Hypoxia and Radiation Therapy: Past History, Ongoing Research, and Future Promise," Curr Mol Med., 9(4):442-458.

Rohlfs et al., 1998, "Arterial Blood Pressure Responses to Cell-free hemoglobin Solutions and the Reaction with Nitric Oxide," J. Biol. Chem., 273(20):12128-12134.

Serwer et al., 2012, "Abstract No. 3301: Novel Oxygen Carrier Proteins, H-NOX, reduce Tumor Hypoxia and Act as Radio sensitizers in an Orthotopic Mouse Model of Human Cancer," International Journal of Radiation Oncology Biology Physics, 84(3S):S707.

Serwer et al., 2013, "Abstract No. ET-088: Preferential Accumulation of a multimeric H-Nox Oxygen Carrier Protein in Multiple Intracranial Glioblastoma Models," Neuro-Oncology, 15(suppl. 3):iii57-iii58.

Serwer et al., 2015, "Real-Time Pet Imaging Demonstrates Tumor Accumulation and Oxygenation by Omx-4.80p, an Oxygen Carrier Engineered for the Treatment of Glioblastoma." Neuro-Oncology, 17:v153-v171—Abstract No. NIMG-45.

Siemens et al., 2008, "Hypoxia increases tumor cell shedding of MHC class I chain-related molecule: role of nitric oxide," Cancer Res., 68(12):4746-4753.

Sissoeff et al. 2005, "Stable Trimerization of Recombinant Rabies Virus Glycoprotein Ectodomain is Required for Interaction with the p75NTR Receptor," J Gen Virol, 86:2543-2552.

Spence et al., 2008, "Regional Hypoxia in Glioblastoma Multiforme Quantified with [18F] Fluoromisonidazole Positron Emission Tomography before Radiotherapy: Correlation with Time to Progression and Survival," Clin Cancer Res, 14(9):2623-2630.

Stetefeld et al., 2003, "Collagen Stabilization at Atomic Level: Crystal Structure of Designed (GlyProPro)10foldon," Structure, 11:339-346.

Stojiljkovic et al., 2003, "Characterization of 9L Glioma Model of the Wistar Rat," J. Neurooncol, 63:1-7.

Takeda et al., 2010, "Differential activation and antagonistic function of HIF-{alpha} isoforms in macrophages are essential for NO homeostasis," Genes Dev., 24(5):491-501.

Tao et al., 1997, "Structure of Bacteriophage T4 Fibritin: A Segmented Coiled Coil and the Role of the C-Terminal Domain," Structure, 5:789-798.

Taylor et al., 1985, "The Rapid Generation of Oligonucleotide-Directed Mutations at High Frequency Using Phosphorothioate-Modified DNA," Nucleic Acids Res., 13(24):8765-8785.

Taylor et al., 1985, "The Use of Phosphorothioate-Modified DNA in Restriction Enzyme Reactions to Prepare Nicked DNA," Nucleic Acids Res., 13(24):8749-8764.

Thiel et al., 2005, "Oxygenation inhibits the physiological tissue-protecting mechanism and thereby exacerbates acute inflammatory lung injury," PLoS Biol., 3(6):e174.

Uversky, 2013, "Unusual biophysics of intrinsically disordered proteins," Biochim Biophys Acta., 1834(5):932-951.

Vandegriff et al., 2004, "Kinetics of NO and O2 Binding to a Maleimide Poly(ethylene glycol)—Conjugated Human Haemoglobin," Biochem. J., 382(Pt1):183-189.

(56) References Cited

OTHER PUBLICATIONS

Varlotto et al., 2005, "Anemia, Tumor Hypoxemia, and the Cancer Patient," Int J Radiat Oncol Biol Phys, 63(1):25-36.

Vaupel, 2004, "Tumor Microenvironmental Physiology and its Implications for Radiation Oncology," Semin Radiat Oncol., 14(3):198-206.

Verhaak et al., 2010, "An Intergrated Genomic Analysis Identifies Clinically Relevant Subtypes of Glioblastoma Characterized by Abnormalities in PDGFRA, IDH1, EGFR, and NF1," Cancer Cell, 17(1):98-110.

Vijayachandra et al., 2000, "characterization of the intracellular domain of the human guanylyl cyclase C receptor provides evidence for a catalytically active homotrimer," Biochemistry, 39(51):16075-16083.

Villard et al., 2002, "Use of a Blood Substitute to Determine Instantaneous Murine Right Ventricular Thickening with Optical Coherence Tomography," Circulation, 105:1843-1849.

Wei et al., 2011, "Hypoxia potentiates glioma-mediated immunosuppression," PLoS One, 6(1):e16195.

Winger et al., 2007, e-published in 2006, "Dissociation of Nitric Oxide from Soluble Guanylate Cyclase and Heme-Nitric Oxide/Oxygen Binding Domain Constructs," The Journal of Biological Chemistry, 282(2):897-907.

Written Opinion mailed Sep. 26, 2016, for International Application No. PCT/US2016/022981, filed on Mar. 17, 2016 (9 pages).

Yang et al., 2002, "Highly Stable Trimers Formed by Human Immunodeficiency Virus Type 1 Envelope Glycoproteins Fused with the Trimeric Motif of T4 Bacteriophage Fibritin," J. Virol 76:4634-4642.

Yao et al., 1992, "Site-directed Mutagenesis of Herpesvirus Glycoprotein Phosphorylation Sites by Recombination Polymerise Chain Reaction," Genome Res., 1(3):205-207.

Yokoi et al., 2010, "Construction of Robust Bio-nanotubes Using the Controlled Self-Assembly of Component Proteins of Bacteriophage T4," Small, 6(17):1873-1879.

Zhang et al., 2009, "Purification and Characterization of a Transgenic Corn Grain-derived Recombinant Collagen Type 1 alpha 1," Biotechnol Prog, 25(6):1660-1668.

Zhao et al., 1997, "Localization of the Heme Binding Region in Soluble Guanylate Cyclase," Biochemistry, 36(50):15959-15964.

Zhao et al., 1999, "Characterization of the nitric oxide sensing domain of soluble guanylate cyclase," Dissertation Abstracts International, vol. 60, No. 7B. Order No. AAl9938578, ProQuest Dissertations & Theses (204 pages).

Zhong et al., 2011, "A novel insight into the heme and NO/CO binding mechanism of the alpha subunit of human soluble guanylate cyclase", J Biol Inorg Chem., 16(8):1227-1239.

Kyi, C. et al. (Jan. 21, 2014, e-published Oct. 23, 2013). "Checkpoint blocking antibodies in cancer immunotherapy," *FEBS Lett* 588(2):368-376.

* cited by examiner

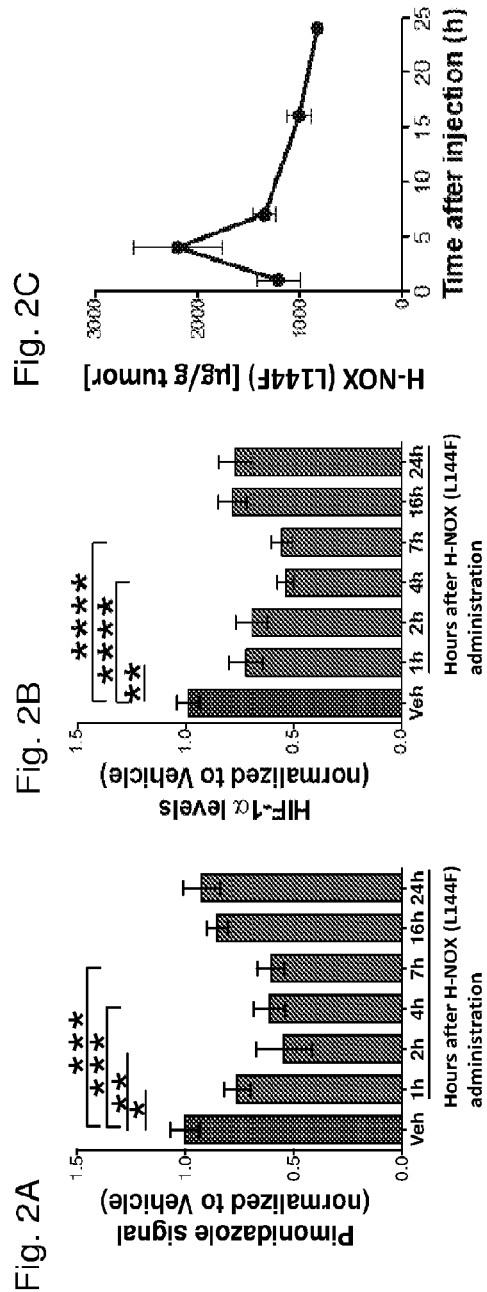

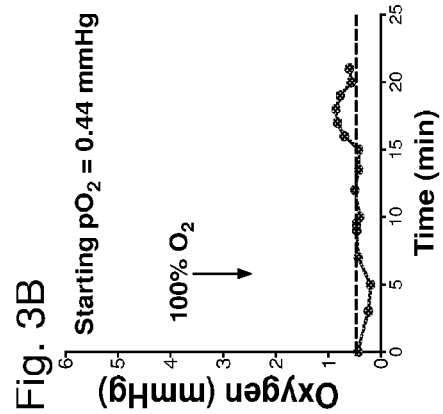
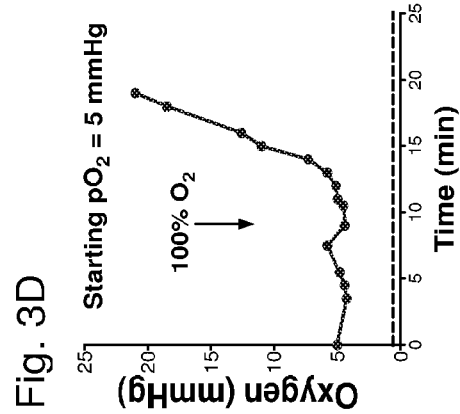
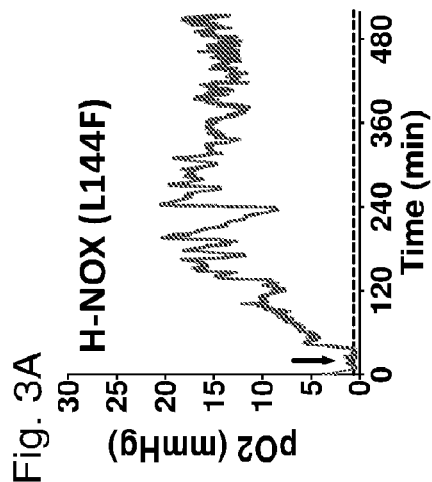
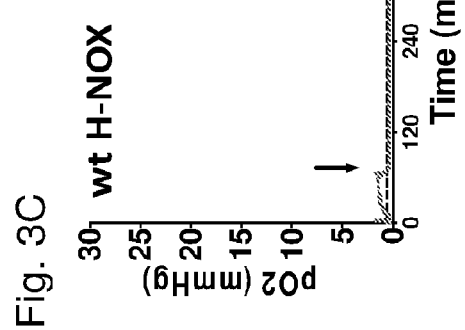

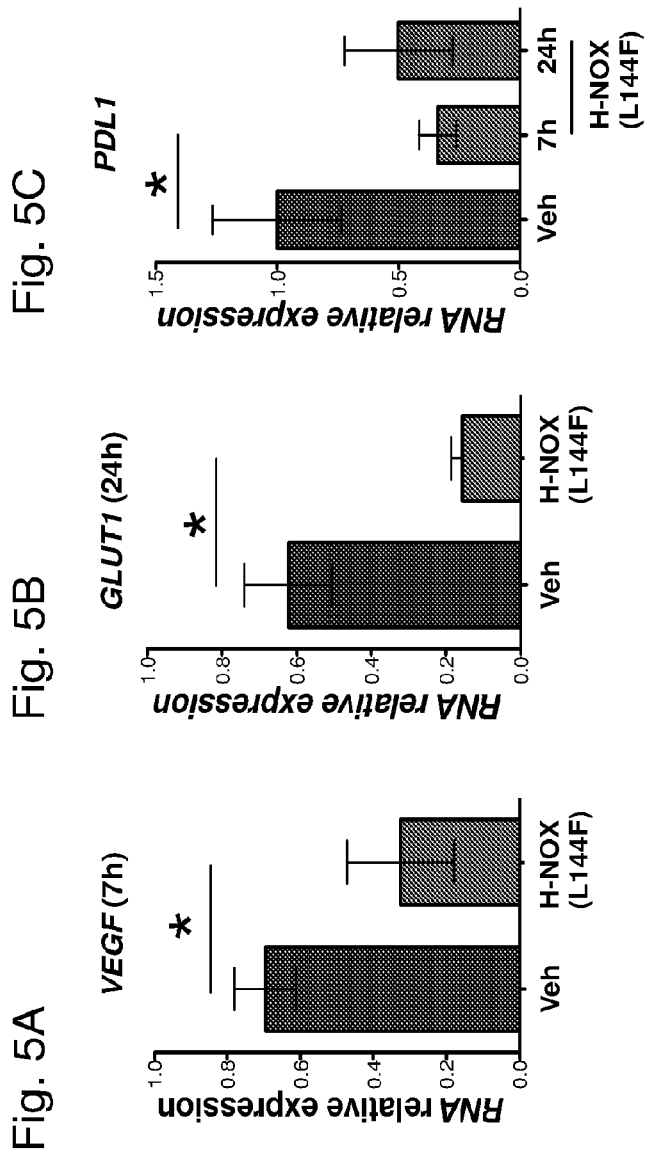

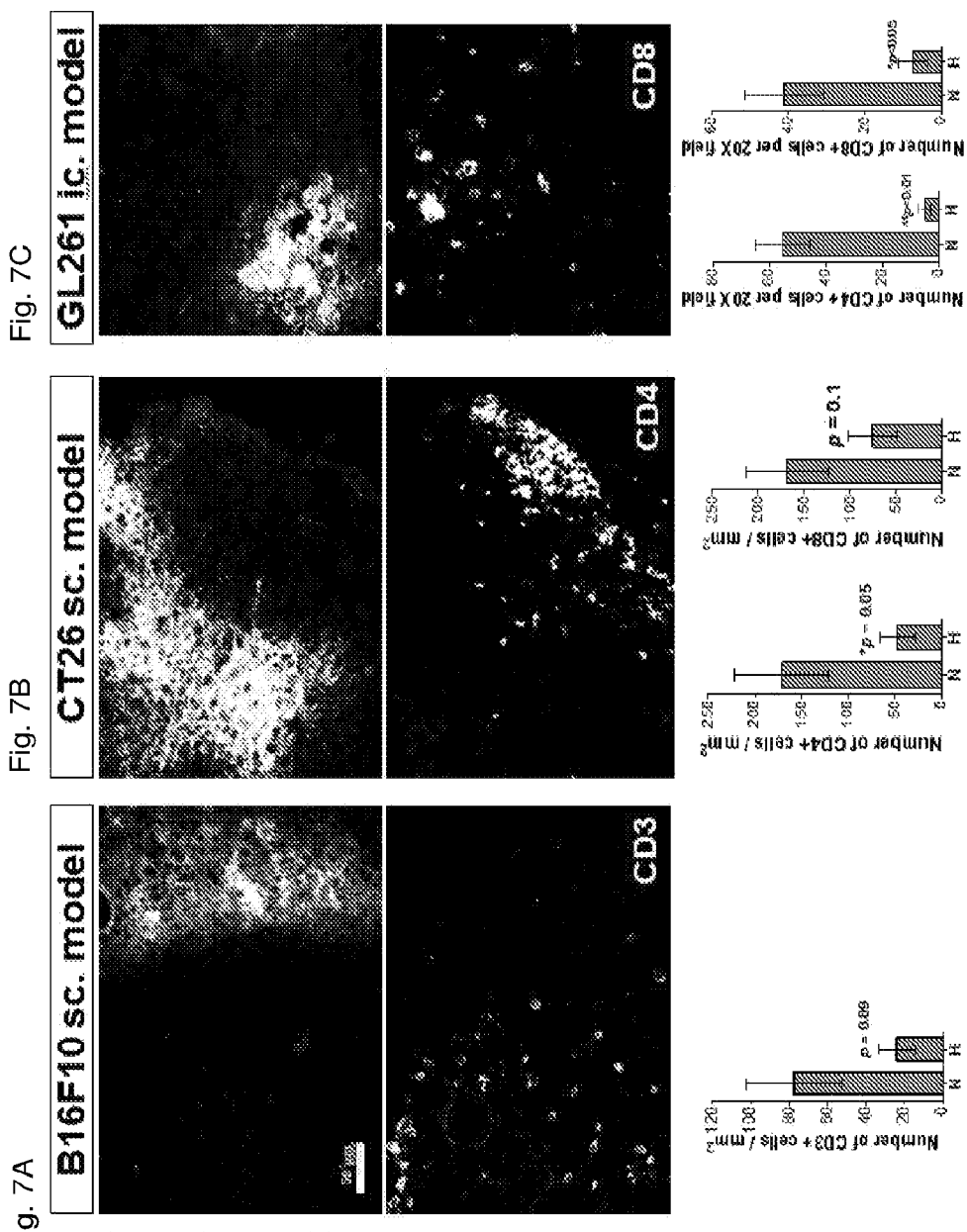

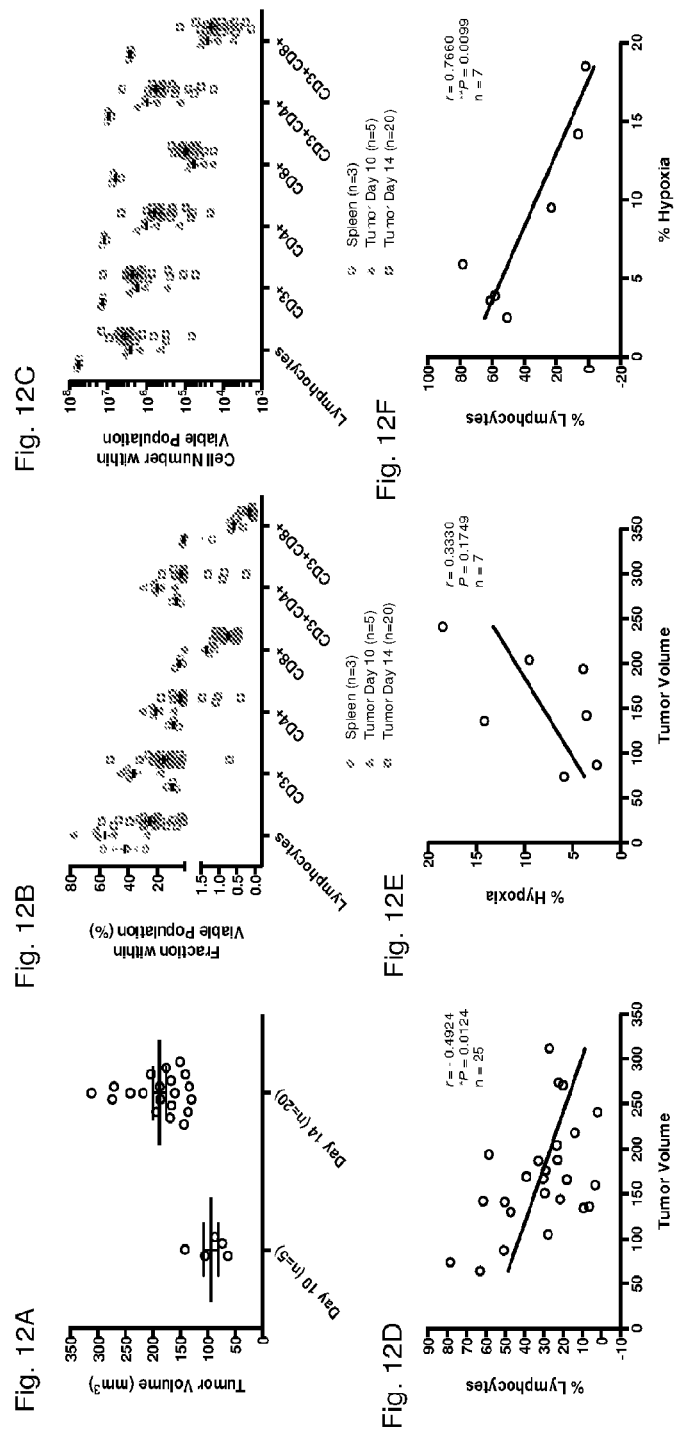

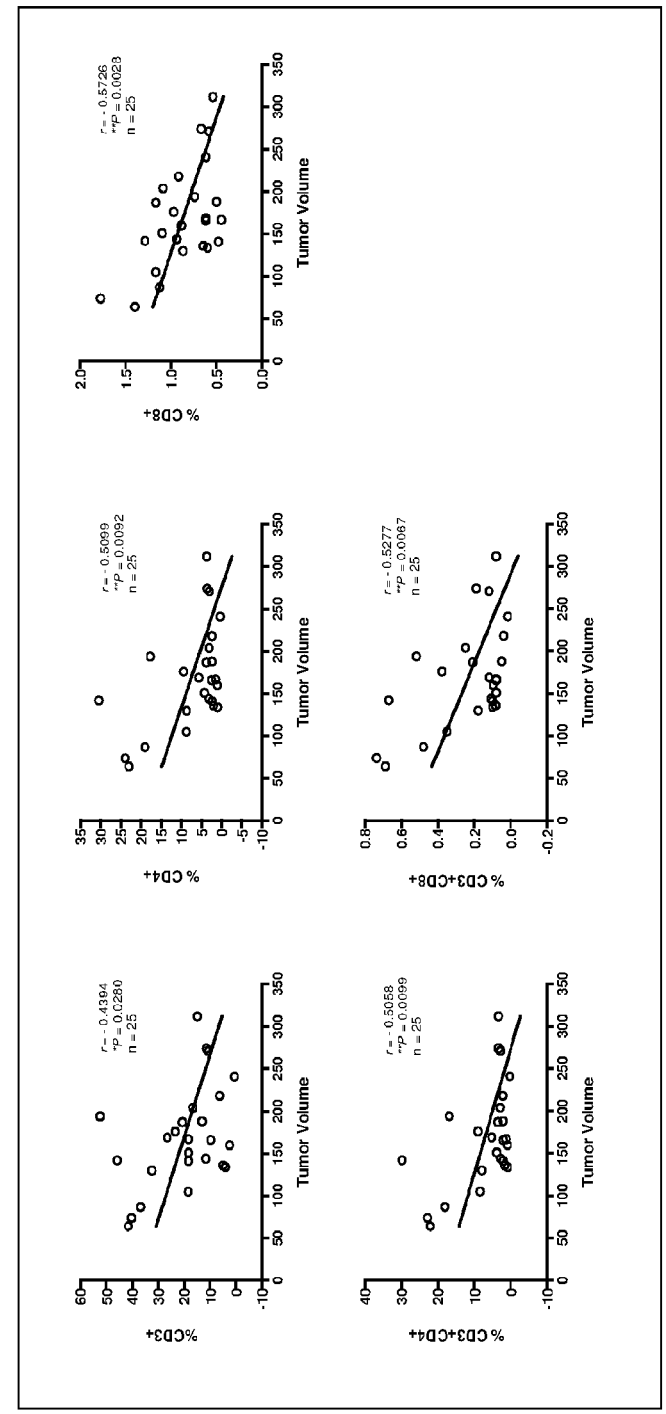

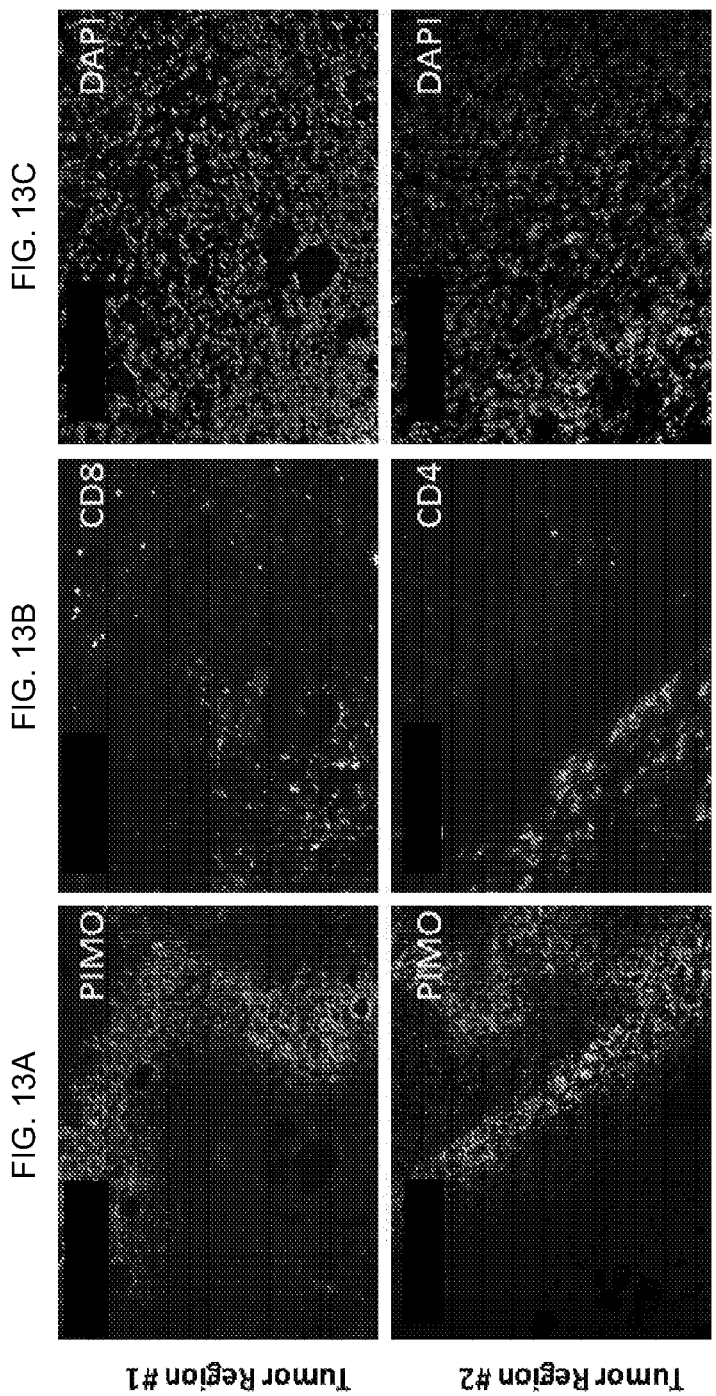

MODULATION OF TUMOR IMMUNITY BY PROTEIN-MEDIATED O$_2$ DELIVERY

CROSS-REFERENCE TO RELATED APPLICATIONS

This is application is a continuation of U.S. application Ser. No. 15/558,957, filed Mar. 17, 2016, which is a National Stage Entry of PCT/US2016/022981, filed Mar. 17, 2016, which claims the benefit of U.S. Provisional Patent Application No. 62/134,523, filed Mar. 17, 2015, the disclosures of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 627042000940SeqList.txt, date recorded: Mar. 17, 2016, size: 41 KB).

TECHNICAL FIELD

This application pertains to the modulation of tumor immunity by delivering oxygen to the tumor by way of a protein O$_2$ carrier polypeptide; for example an H-NOX protein.

BACKGROUND OF THE INVENTION

The hypoxic tumor microenvironment suppresses the host's immune anti-tumor defenses by modulating multiple signaling pathways including, but not limited to, hypoxia inducible factor (HIF-1) signaling (Codo et al., 2014 Oncotarget, 5 (17), 7651-7662; Lee, Mace, & Repasky, 2010 Int J Hyperthermia, 26 (3), 232-246; Wei et al., 2011 PLOS One, 6 (1), e16195). Major hypoxia immunomodulating pathways are summarized in FIG. 1. Briefly, HIF-1 has been shown to: a) activate adenosinergic A2 and PD-L1 pathways that inhibit recruitment and activation of helper and killer T-cells and NK cells, key effectors of anti-tumor responses (Noman et al., 2014 J Exp Med, 211 (5), 781-790; Ohta et al., 2006 Proc Natl Acad Sci USA, 103 (35), 13132-13137); b) recruit and activate inhibitory regulatory T cells (Treg), tumor associated macrophages (TAM) and other myeloid-derived suppressor cells (MDSC) (Chaturvedi et al., 2014 Proc Natl Acad Sci USA, 111 (20), E2120-2129; Corzo et al., 2010 J Exp Med, 207 (11), 2439-2453; Wei et al., 2011); c) directly inhibit the ability of tumor cells to be recognized by immune system (Siemens et al., 2008 Cancer Res, 68 (12), 4746-4753). In addition, HIF-1-dependent and -independent epigenetic mechanisms contribute to inhibition of anti-tumor immune-responses and enhance tumor growth, angiogenesis and metastasis (Codo et al., 2014; Mimura et al., 2011 J Pharmacol Sci, 115 (4), 453-458).

In mouse metastatic tumor models, continuous supplemental oxygenation has been shown to inhibit tumor growth and prevent tumor's immune escape through inhibition of A2AR (A2A adenosine receptor) adenosinergic pathway leading to T and NK cell activation (Hatfield et al., 2015 Sci Transl Med, 7 (277), 277ra230). Specifically, continuous treatment with 60% respiratory oxygen of mice bearing MCA205, B16 or 4T1 pulmonary metastases resulted in >2-fold decrease in number of metastatic foci and enhanced survival. These data correlated with decrease in tumor and lymphocyte hypoxia, increased activated CD8 T cell (CD8+ CD69+CD44+) tumor infiltration, upregulation of immunostimulating cytokines and chemokines and were dependent on intact A2AR signaling. At the same time respiratory hyperoxia was shown to reduce the number and suppressive the activity of Treg in pulmonary tumor microenvironment (TME) due to reduced Foxp3, CD39/CD73 (adenosine generating enzymes upstream of A2AR) and CTLA-4 expression. Finally, tumor regression induced by dual CTLA-4/PD-1 blockade of pulmonary tumors was enhanced by continuous respiratory hyperoxia.

Despite convincing pre-clinical evidence demonstrating the capacity of tumor oxygenation to reverse immunosuppressive TME and inhibit tumor growth, in human clinical trials supplemental oxygenation using hyperbaric or normobaric oxygen yielded limited effects (Overgaard, 2007 J Clin Oncol, 25 (26), 4066-4074). This is likely due to the inability of soluble oxygen to effectively diffuse beyond ~80 μm from blood vessels, limiting its penetration deep into hypoxic tumor tissue. Therefore, the need exists for oxygen delivery agents that penetrate into patients' tumors to transport oxygen beyond the normal diffusion limits, and thereby oxygenate hypoxic microenvironments to impede immunosuppressive pathways. This will result in maximal stimulation of anti-tumor immune responses, both alone and in combination with other immune checkpoint inhibitors and other cancer immunotherapy approaches.

H-NOX proteins (named for Heme-Nitric oxide and OXygen binding domain) are members of a highly-conserved, well-characterized family of hemoproteins (Iyer, L M et al. (2003) BMC Genomics 4 (1): 5; Karow, D S et al. (2004) Biochemistry 43 (31): 10203-10211; Boon, E M et al. (2005) Nature Chem. Biol. 1:53-59; Boon, E M et al. (2005) Curr. Opin. Chem. Biol. 9 (5): 441-446; Boon, E M et al. (2005) J. Inorg. Biochem. 99 (4): 892-902; Cary, S P et al. (2005) Proc Natl Acad Sci USA 102 (37): 13064-9; Karow D S et al. (2005) Biochemistry 44 (49): 16266-74; Cary, S P et al. (2006) Trends Biochem Sci 31 (4): 231-9; Boon, E M et al. (2006) J Biol Chem 281 (31): 21892-902; Winger, J A et al. (2007) J Biol Chem. 282 (2): 897-907). H-NOX proteins are nitric-oxide-neutral, unlike previous hemoglobin-based oxygen carriers, H-NOX do not scavenge circulating nitric oxide (NO), and thus are not associated with hypertensive or renal side effects. The intrinsic low NO reactivity (and high NO stability) makes wild-type and mutant H-NOX proteins desirable blood substitutes because of the lower probability of inactivation of H-NOX proteins by endogenous NO and the lower probability of scavenging of endogenous NO by H-NOX proteins. Importantly, the presence of a distal pocket tyrosine in some H-NOX proteins (Pellicena, P. et al. (2004) Proc Natl. Acad Sci USA 101 (35): 12854-12859) is suggestive of undesirable, high NO reactivity, contraindicating use as a blood substitute. For example, by analogy, a Mycobacterium tuberculosis hemoglobin protein, with a structurally analogous distal pocket tyrosine, reacts extremely rapidly with NO, and is used by the Mycobacterium to effectively scavenge and avoid defensive NO produced by an infected host (Ouellet, H. et al. (2002) Proc. Natl. Acad. Sci. USA 99 (9): 5902-5907). However, it was surprisingly discovered that H-NOX proteins actually have a much lower NO reactivity than that of hemoglobin making their use as blood substitutes possible.

H-NOX proteins for the delivery of O$_2$ and/or NO for therapeutic and other uses are described in U.S. Pat. Nos. 8,404,631 and 8,404,632; WO 2007/139791, WO 2007/139767 and WO 2014/107171; and U.S. patent application Ser. No. 14/530,569, the contents of each is incorporated by reference in its entirety.

All references cited herein, including patent applications and publications, are incorporated herein by reference in their entirety.

BRIEF SUMMARY OF THE INVENTION

The invention provides methods for modulating tumor immunity in an individual with a tumor comprising administering to the individual an effective amount of an $O_2$ carrier polypeptide. In some embodiments, the invention provides methods for enhancing an immune response to the tumor. In some embodiments, the invention provides methods for increasing lymphocyte infiltration to a tumor in an individual comprising administering to the individual an effective amount of an $O_2$ carrier polypeptide. In some embodiments, the increase in lymphocyte infiltration to the tumor comprises an increase in infiltration of one or more of CD4 cells, CD8 cells, or NK cells. In some embodiments, the increase in lymphocyte infiltration to the tumor is accompanied by inhibition of one or more of Treg cells, tumor associated macrophages or myeloid derived suppressor cells in the tumor. In some embodiments, the increase in lymphocyte infiltration to the tumor is accompanied by an increase in MHC1 expression on the tumor cells. In some embodiments, the modulating of tumor immunity comprises increasing antigen processing. In some embodiments, the modulating of tumor immunity comprises increasing the presentation capabilities of dendritic cells (DC).

In some embodiments, the invention provides methods for decreasing expression of hypoxia inducible factor 1α (HIF-1α) and/or hypoxia inducible factor 2α (HIF-2α) in a tumor in an individual comprising administering to the individual an effective amount of an $O_2$ carrier polypeptide. In some embodiments, the invention provides methods for decreasing expression of programmed death ligand-1 (PD-L1) in a tumor in an individual comprising administering to the individual an effective amount of an $O_2$ carrier polypeptide. In some embodiments, the invention provides methods for decreasing expression of A2A adenosine receptor (A2AR) in a tumor in an individual comprising administering to the individual an effective amount of an $O_2$ carrier polypeptide.

In some embodiments of the above embodiments, the tumor is a brain tumor, a glioblastoma, a bone tumor, a pancreatic tumor, a skin tumor, a tumor of the head or neck, a melanoma, a lung tumor, a uterine tumor, an ovarian tumor, a colorectal tumor, a liver tumor, a hepatocellular carcinoma, a stomach tumor, a testicular tumor, an endometrial tumor, a cervical tumor, a vaginal tumor, a Hodgkin's lymphoma, a non-Hodgkin's lymphoma, an esophageal tumor, an intestinal tumor, a thyroid tumor, an adrenal tumor, a bladder tumor, a kidney tumor, breast tumor, a multiple myeloma tumor, a sarcoma, or a squamous cell tumor.

In some aspects, the invention provides methods for treating cancer in an individual comprising administering to the individual an effective amount of an $O_2$ carrier polypeptide. In some embodiments, the cancer is brain cancer, glioblastoma, bone cancer, pancreatic cancer, skin cancer, cancer of the head or neck, melanoma, lung cancer, uterine cancer, ovarian cancer, colorectal cancer, anal cancer, liver cancer, hepatocellular carcinoma, stomach cancer, testicular cancer, endometrial cancer, cervical cancer, Hodgkin's Disease, non-Hodgkin's lymphoma, esophageal cancer, intestinal cancer, thyroid cancer, adrenal cancer, bladder cancer, kidney cancer, breast cancer, multiple myeloma, sarcoma, anal cancer or squamous cell cancer.

In some embodiments of the above aspects and embodiments, the individual is a mammal. In further embodiments, the mammal is a human (e.g., a human patient). In other embodiments, the mammal is a pet, a laboratory research animal, or a farm animal. In some embodiments, the pet, research animal or farm animal is a dog, a cat, a horse, a monkey, a rabbit, a rat, a mouse, a guinea pig, a hamster, a pig, or a cow.

In some embodiments of the above aspects and embodiments, the $O_2$ carrier polypeptide is administered by intravenous, intra-arterial, intratumoral, intravesicular, inhalation, intraperitoneal, intrapulmonary, intramuscular, subcutaneous, intra-tracheal, transmucosal, intraocular, intrathecal, or transdermal administration. In some embodiments, administration of the $O_2$ carrier polypeptide is repeated. In some embodiments, administration of the $O_2$ carrier polypeptide is repeated daily or twice a day from about 4 weeks to about 8 weeks. In some embodiments, the $O_2$ carrier polypeptide is administered every four, every 8, every 12 or every 24 hours for a period of about one to about 10 days. In some embodiments, the $O_2$ carrier polypeptide is administered as a bolus. In other embodiments, the $O_2$ carrier polypeptide is administered by infusion. In some embodiments, the $O_2$ carrier polypeptide is infused in the individual for about 15 minutes, about 30 minutes, about 1 hour, about 2 hours, about 3 hours, about 6 hours, about 12 hours, about 24 hours or more than 24 hours.

In some embodiments, the invention provides methods to modulate tumor immunity or to treat cancer in an individual wherein an $O_2$ carrier polypeptide is administered in combination with radiation therapy. In some embodiments, the radiation therapy is administered to the individual 1, 2, 3, 4, 5, 6, 8, 10, 12, 14, 16, 18, 20 or 24 hours after the $O_2$ carrier polypeptide is administered. In some embodiments, the radiation is X-radiation. In some embodiments, the X-radiation is administered at about 0.5 gray to about 75 gray. In some embodiments, the administration of the $O_2$ carrier polypeptide and/or the administration of the radiation is repeated. In some embodiments, the administration is repeated more than about any of two, three, four times, five times, ten times, 15 times, 20 times, 25 times or 30 times. In some embodiments, the administration is repeated after one week, two weeks, three weeks, or four weeks.

In some embodiments, the invention provides methods to modulate tumor immunity or to treat cancer in an individual wherein an $O_2$ carrier polypeptide is administered in combination with chemotherapy or immunotherapy. In some embodiments, the chemotherapy comprises a cytotoxin. In some embodiments, the administration of the $O_2$ carrier polypeptide and/or the administration of the chemotherapy is repeated. In some embodiments, the immunotherapy is one or more of an anticancer vaccine, an adoptive immune cell therapy or an agent that targets an immune checkpoint regulator. In some embodiments, the immunotherapy targets one or more of CTLA-4, PD1, PD-L1, or an immune checkpoint regulator. In some embodiments, the adoptive immune therapy is a chimeric antigen receptor expressing T cell or an engineered TCR-T cell. In some embodiments, the immune therapy is an oncolytic virus or a Bispecific T cell Engager (BiTE). In some embodiments, the administration of the $O_2$ carrier polypeptide and/or the administration of the immunotherapy is repeated.

In some embodiments of the above embodiments, the $O_2$ carrier polypeptide is in a pharmaceutical composition. In some embodiments, the pharmaceutical composition further comprises a pharmaceutically acceptable carrier. In some embodiments of any of the above embodiments, the $O_2$ carrier polypeptide is an H-NOX protein.

In some aspects, the invention provides methods for modulating tumor immunity in an individual with a tumor comprising administering to the individual an effective amount of an H-NOX protein. In some embodiments, the invention provides methods for enhancing an immune response to the tumor. In some embodiments, the invention provides methods for increasing leucocyte infiltration to a tumor in an individual comprising administering to the individual an effective amount of an H-NOX protein. In some embodiments, the invention provides methods for increasing lymphocyte infiltration to a tumor in an individual comprising administering to the individual an effective amount of an H-NOX protein. In some embodiments, the increase in lymphocyte infiltration to the tumor comprises an increase in infiltration of one or more of CD4 cells, CD8 cells, or NK cells. In some embodiments, the increase in lymphocyte infiltration to the tumor is accompanied by inhibition of one or more of Treg cells, tumor associated macrophages or myeloid derived suppressor cells in the tumor. In some embodiments, the increase in lymphocyte infiltration to the tumor is accompanied by an increase in MHC1 expression on the tumor cells. In some embodiments, the modulating of tumor immunity comprises increasing antigen processing. In some embodiments, the modulating of tumor immunity comprises increasing lymphocyte activation. In some embodiments, the modulating of tumor immunity comprises increasing the presentation capabilities of dendritic cells (DC).

In some embodiments, the invention provides methods for decreasing expression of hypoxia inducible factor 1α (HIF-1α) and/or hypoxia inducible factor 2α (HIF-2α) in a tumor in an individual comprising administering to the individual an effective amount of an H-NOX protein. In some embodiments, the invention provides methods for decreasing expression of programmed death ligand-1 (PD-L1) in a tumor in an individual comprising administering to the individual an effective amount of an H-NOX protein. In some embodiments, the invention provides methods for decreasing expression of A2A adenosine receptor (A2AR) in a tumor in an individual comprising administering to the individual an effective amount of an H-NOX protein.

In some embodiments of the above embodiments, the tumor is a brain tumor, a glioblastoma, a bone tumor, a pancreatic tumor, a skin tumor, a tumor of the head or neck, a melanoma, a lung tumor, a uterine tumor, an ovarian tumor, a colorectal tumor, an anal tumor, a liver tumor, a hepatocellular carcinoma, a stomach tumor, a testicular tumor, an endometrial tumor, a cervical tumor, a vaginal tumor, a Hodgkin's lymphoma, a non-Hodgkin's lymphoma, an esophageal tumor, an intestinal tumor, a thyroid tumor, an adrenal tumor, a bladder tumor, a kidney tumor, breast tumor, a multiple myeloma tumor, a sarcoma, or a squamous cell tumor.

In some aspects, the invention provides methods for treating cancer in an individual comprising administering to the individual an effective amount of an H-NOX protein. In some embodiments, the cancer is brain cancer, glioblastoma, bone cancer, pancreatic cancer, skin cancer, cancer of the head or neck, melanoma, lung cancer, uterine cancer, ovarian cancer, colorectal cancer, anal cancer, liver cancer, hepatocellular carcinoma, stomach cancer, testicular cancer, endometrial cancer, cervical cancer, Hodgkin's Disease, non-Hodgkin's lymphoma, esophageal cancer, intestinal cancer, thyroid cancer, adrenal cancer, bladder cancer, kidney cancer, breast cancer, multiple myeloma, sarcoma or squamous cell cancer.

In some embodiments of the above aspects and embodiments, the individual is a mammal. In further embodiments, the mammal is a human (e.g., a human patient). In other embodiments, the mammal is a pet, a laboratory research animal, or a farm animal. In some embodiments, the pet, research animal or farm animal is a dog, a cat, a horse, a monkey, a rabbit, a rat, a mouse, a guinea pig, a hamster, a pig, or a cow.

In some embodiments of the above aspects and embodiments, the H-NOX protein is administered by intravenous, intra-arterial, intratumoral, intravesicular, inhalation, intraperitoneal, intrapulmonary, intramuscular, subcutaneous, intra-tracheal, transmucosal, intraocular, intrathecal, or transdermal administration. In some embodiments, administration of the H-NOX protein is repeated. In some embodiments, administration of the H-NOX protein is repeated daily or twice a day from about 4 weeks to about 8 weeks. In some embodiments, the H-NOX protein is administered every four, every 8, every 12, every 24 hours, or every 48 hours for a period of about one to about 10 days. In some embodiments, the H-NOX protein is administered as a bolus. In other embodiments, the H-NOX protein is administered by infusion. In some embodiments, the H-NOX protein is infused in the individual for about 15 minutes, about 30 minutes, about 1 hour, about 2 hours, about 3 hours, about 6 hours, about 12 hours, about 24 hours or more than 24 hours.

In some embodiments, the invention provides methods to modulate tumor immunity or to treat cancer in an individual wherein an H-NOX protein is administered in combination with radiation therapy. In some embodiments, the radiation therapy is administered to the individual 1, 2, 3, 4, 5, 6, 8, 10, 12, 14, 16, 18, 20 or 24 hours after the H-NOX protein is administered. In some embodiments, the radiation is X-radiation. In some embodiments, the X-radiation is administered at about 0.5 gray to about 75 gray. In some embodiments, the administration of the H-NOX protein and/or the administration of the radiation is repeated. In some embodiments, the administration is repeated more than about any of two, three, four times, five times, ten times, 15 times, 20 times, 25 times, 30 times or 40 times. In some embodiments, the administration is repeated after one week, two weeks, three weeks, or four weeks or more.

In some embodiments, the invention provides methods to modulate tumor immunity or to treat cancer in an individual wherein an H-NOX protein is administered in combination with chemotherapy or immunotherapy. In some embodiments, the chemotherapy comprises a cytotoxin. In some embodiments, the administration of the H-NOX protein and/or the administration of the chemotherapy is repeated. In some embodiments, the immunotherapy is one or more of an anticancer vaccine, an adoptive immune cell therapy or an agent that targets an immune checkpoint regulator. In some embodiments, the immunotherapy targets one or more of CTLA-4, PD1, PD-L1, or an immune checkpoint regulator. In some embodiments, the adoptive immune therapy is a chimeric antigen receptor expressing T cell or an engineered TCR-T cell. In some embodiments, the immune therapy is an oncolytic virus or a Bispecific T cell Engager (BiTE). In some embodiments, the administration of the H-NOX protein and/or the administration of the immunotherapy is repeated.

In some embodiments of the above aspects and embodiments, the H-NOX protein is a *T. tengcongensis* H-NOX, a L. pneumophilia 2 H-NOX, a H. sapiens β1, a R. norvegicus β1, a C. lupus H-NOX, a D. melangaster β1, a D. melangaster CG14885-PA, a C. elegans GCY-35, a N. punctiforme H-NOX, C. crescentus H-NOX, a S. oneidensis H-NOX, or C. acetobutylicum H-NOX. In some embodiments, the H-NOX protein comprises a H-NOX domain corresponding to the H-NOX domain of T. tengcongensis set forth in SEQ ID NO:2.

In some embodiments, the H-NOX comprises one or more distal pocket mutations. In some embodiments, the distal pocket mutation is an amino acid substitution at a site corresponding to L144 of T. tengcongensis H-NOX. In some embodiments, the H-NOX is a T. tengcongensis H-NOX comprising an amino acid substitution at position 144. In some embodiments, the amino acid substitution at position 144 is an L144F substitution.

In some embodiments, the H-NOX protein is a polymeric H-NOX protein. In some embodiments, the polymeric H-NOX protein comprises monomers, wherein the monomers comprise an H-NOX domain and a polymerization domain. In some embodiments, the H-NOX domain is covalently linked to the polymerization domain. In some embodiments, the polymeric H-NOX protein is a trimeric H-NOX protein. In some embodiments, the trimeric H-NOX protein comprises one or more trimerization domains. In some embodiments, the trimeric H-NOX protein comprises three monomers, wherein the monomers comprise an H-NOX domain and a trimerization domain, wherein the trimerization domain is a bacteriophage T4 trimerization domain. In some embodiments, the trimerization domain is a foldon domain. In some embodiments, the foldon domain comprises the amino acid sequence of SEQ ID NO:4.

In some embodiments, the H-NOX protein is fused to an Fc domain of an immunoglobulin. In some embodiments, the H-NOX protein is covalently bound to polyethylene glycol.

In some embodiments, the $O_2$ dissociation constant of the H-NOX protein is within 2 orders of magnitude of that of hemoglobin, and wherein the NO reactivity of the H-NOX protein is at least 10-fold lower than that of hemoglobin. In some embodiments, the $O_2$ dissociation constant of the polymeric H-NOX protein is between about 1 nM and about 1000 nM at 20° C. In some embodiments, the $O_2$ dissociation constant of the H-NOX protein is between about 1 µM and about 10 µM at 20° C. In some embodiments, the $O_2$ dissociation constant of the H-NOX protein is between about 10 µM and about 50 µM at 20° C. In some embodiments, the NO reactivity of the H-NOX protein is less than about 700 $s^{-1}$ at 20° C. In some embodiments, the NO reactivity of the H-NOX protein is at least 100-fold lower than that of hemoglobin. In some embodiments, the NO reactivity of the H-NOX protein is at least 1,000-fold lower than that of hemoglobin. In some embodiments, the $k_{off}$ for oxygen of the H-NOX protein is less than or equal to about 0.65 $s^{-1}$ at 20° C. In some embodiments, the $k_{off}$ for oxygen of the H-NOX protein is between about 0.21 $s^{-1}$ and about 0.65 $s^{-1}$ at 20° C. In some embodiments, the $k_{off}$ for oxygen of the H-NOX protein is between about 1.35 $s^{-1}$ and about 2.9 $s^{-1}$ at 20° C. In some embodiments, the rate of heme autoxidation of the H-NOX protein is less than about 1 $h^{-1}$ at 37° C.

In some embodiments of the above embodiments, the H-NOX protein is in a pharmaceutical composition. In some embodiments, the pharmaceutical composition further comprises a pharmaceutically acceptable carrier.

In some aspects the invention provides the use of an $O_2$ carrier protein for modulating tumor immunity in an individual. In some embodiments, the modulating tumor immunity comprises enhancing an immune response to the tumor. In some embodiments, the invention provides the use of an $O_2$ carrier polypeptide for increasing leucocyte infiltration to a tumor in an individual. In some embodiments, the invention provides the use of an $O_2$ carrier polypeptide for increasing lymphocyte infiltration to a tumor in an individual. In some embodiments, the increase in lymphocyte infiltration to the tumor comprises an increase in infiltration of one or more of CD4 cells, CD8 cells, or NK cells. In some embodiments, the increase in lymphocyte infiltration to the tumor is accompanied by inhibition of one or more of Treg cells, tumor associated macrophages or myeloid derived suppressor cells in the tumor. In some embodiments, the increase in leucocyte infiltration to the tumor is accompanied by an increase in MHC1 expression on the tumor cells. In some embodiments, the increase in lymphocyte infiltration to the tumor is accompanied by an increase in MHC1 expression on the tumor cells.

In some embodiments, the invention provides the use of an $O_2$ carrier polypeptide for decreasing expression of HIF-1α and/or HIF-2α in a tumor in an individual. In some embodiments, the invention provides the use of an $O_2$ carrier polypeptide for decreasing expression of PD-L1 in a tumor in an individual. In some embodiments, the invention provides the use of an $O_2$ carrier polypeptide for decreasing expression of A2AR in a tumor in an individual.

In some embodiments of the above uses, the tumor is a brain tumor, a glioblastoma, a bone tumor, a pancreatic tumor, a skin tumor, a tumor of the head or neck, a melanoma, a lung tumor, a uterine tumor, an ovarian tumor, a colorectal tumor, an anal tumor, a liver tumor, a hepatocellular carcinoma, a stomach tumor, a testicular tumor, an endometrial tumor, a cervical tumor, a vaginal tumor, a Hodgkin's lymphoma, a non-Hodgkin's lymphoma, an esophageal tumor, an intestinal tumor, a thyroid tumor, an adrenal tumor, a bladder tumor, a kidney tumor, a breast tumor, a multiple myeloma tumor, a sarcoma, or a squamous cell tumor.

In some embodiments, the invention provides the use of an $O_2$ carrier protein for treating cancer in an individual. In some embodiments, the cancer is brain cancer, glioblastoma, bone cancer, pancreatic cancer, skin cancer, cancer of the head or neck, melanoma, lung cancer, uterine cancer, ovarian cancer, colorectal cancer, anal cancer, liver cancer, hepatocellular carcinoma, stomach cancer, testicular cancer, endometrial cancer, cervical cancer, Hodgkin's Disease, non-Hodgkin's lymphoma, esophageal cancer, intestinal cancer, thyroid cancer, adrenal cancer, bladder cancer, kidney cancer, breast cancer, multiple myeloma, sarcoma, or squamous cell cancer.

In some embodiments of the above uses, the individual is a mammal. In some embodiments, the mammal is a human.

In some embodiments of the above uses, the $O_2$ carrier polypeptide is an H-NOX protein. In some embodiments, the H-NOX protein is a T. tengcongensis H-NOX, a L. pneumophilia 2 H-NOX, a H. sapiens B1, a R. norvegicus B1, a C. lupus H-NOX, a D. melangaster B1, a D. melangaster CG14885-PA, a C. elegans GCY-35, a N. punctiforme H-NOX, C. crescentus H-NOX, a S. oneidensis H-NOX, or C. acetobutylicum H-NOX. In some embodiments, the H-NOX protein comprises a H-NOX domain corresponding to the H-NOX domain of T. tengcongensis set forth in SEQ ID NO:2. In some embodiments, the H-NOX comprises one or more distal pocket mutations. In some embodiments, the distal pocket mutation is an amino acid substitution at a site corresponding to L144 of T. tengcongensis H-NOX. In some embodiments, the H-NOX is a *T. tengcongensis* H-NOX comprising an amino acid substitution at position 144. In some embodiments, the amino acid substitution at position 144 is an L144F substitution.

In some embodiments, the H-NOX protein is a polymeric H-NOX protein. In some embodiments, the polymeric H-NOX protein comprises monomers, wherein the monomers comprise an H-NOX domain and a polymerization domain. In some embodiments, the H-NOX domain is covalently linked to the polymerization domain. In some embodiments, the polymeric H-NOX protein is a trimeric H-NOX protein. In some embodiments, the trimeric H-NOX protein comprises one or more trimerization domains. In some embodiments, the trimeric H-NOX protein comprises three monomers, wherein the monomers comprise an H-NOX domain and a trimerization domain, wherein the trimerization domain is a bacteriophage T4 trimerization domain. In some embodiments, the trimerization domain is a foldon domain. In some embodiments, the foldon domain comprises the amino acid sequence of SEQ ID NO:4.

In some embodiments, the H-NOX protein is fused to an Fc domain of an immunoglobulin. In some embodiments, the H-NOX protein is covalently bound to polyethylene glycol.

In some aspects, the invention provides kits for modulating tumor immunity in an individual comprising an $O_2$ carrier protein for use in the methods described herein. In some embodiments, the kit further comprises one or more of a vial, a vessel, an ampule, a bottle, a jars, or flexible packaging. In some embodiments, the kit further comprises one or more buffer. In some embodiments, the kit further comprises instructions for use.

BRIEF DESCRIPTION OF THE DRAWINGS

FIGS. 2A-2C show tumor oxygenation after single bolus dose of PEGylated trimer Tt H-NOX L144F assessed by pimonidazole and HIF-1 ELISA. FIG. 2A shows pimonidazole levels measured by competitive ELISA. FIG. 2B shows HIF-1α levels measured by sandwich ELISA. Graphs show quantification of pimonidazole and HIF-1α signals after PEGylated trimer Tt H-NOX L144F administration. Mean values+/−SEM. *p<0.001, p<0.01 by One way ANOVA and Bonferroni's post-hoc tests. FIG. 2C shows assessment of tumors for the accumulation of PEGylated trimer Tt H-NOX L144F by sandwich H-NOX ELISA and results expressed per gram of tumor tissue.

FIGS. 3A-3D show direct measurements of tumor tissue oxygenation following PEGylated trimer Tt H-NOX L144F administration. Tumors were treated either with PEGylated trimer Tt H-NOX L144F (FIG. 3A), non-functional control Tt H-NOX protein (FIG. 3C), or with 100% oxygen starting at $pO_2$=0.44 mmHg (FIG. 3B) with 100% oxygen starting at $pO_2$=5 mmHg (FIG. 3D).

FIGS. 5A-5C show PEGylated trimer Tt H-NOX L144F downregulates HIF-1α targets involved in immunosuppression. Mice bearing H460 subcutaneous xenograft tumors (150-300 mm³) were either pre-treated with PEGylated trimer Tt H-NOX L144 For treated with vehicle alone, and harvested for qRT-PCR analysis. FIG. 5A shows expression of VEGF. FIG. 5B shows expression of GLUT1. FIG. 5C shows expression of PD-L1.

FIG. 6A shows the nucleic acid (SEQ ID NO:5) and amino acid sequence (SEQ ID NO: 6) of the foldon domain of bacteriophage T4 fibritin fused to the C-terminus of a *Thermoanaerobacter tengcongensis* L144F H-NOX sequence and including the His6 tag.

FIG. 6B shows the nucleic acid (SEQ ID NO:7) and amino acid sequence (SEQ ID NO:8) of the L144F H-NOX-foldon monomer without a His6 tag.

FIGS. 7A-7C show representative images of tumor hypoxia and T cell infiltration is B16F10 subcutaneous tumors (FIG. 7A), CT26 subcutaneous tumors (FIG. 7B) and GL261 intracranial tumors (FIG. 7C). Hypoxia (top panels) and T cell infiltration (middle panels) is shown by immunohistochemistry. Bottom panels show results of quantitative analysis of multiple tumor sections. Significantly fewer CD4 and CD8 T cells infiltrate the hypoxic regions of tumors.

FIGS. 12A-12K show that larger tumor size correlates with enhanced hypoxia and reduced lymphocyte infiltration in subcutaneous 4T1-Luc syngeneic mouse tumors. FIG. 12A shows tumor volumes on day 10 and day 14 post-implant. FIG. 12B shows fraction of lymphocytes within the viable cell population. FIG. 12C shows the absolute lymphocyte cell numbers within the viable population. FIG. 12D shows a negative correlation between tumor volume and percentage lymphocytes. FIG. 12E shows a positive correlation between tumor volume and percentage hypoxia. FIG. 12F shows a negative correlation between percentage hypoxia and percentage lymphocytes. FIG. 12G shows a negative correlation between tumor volume and percentage CD3-positive T cells. FIG. 12H shows a negative correlation between tumor volume and percentage CD4-positive T cells. FIG. 12I shows a negative correlation between tumor volume and percentage CD8-positive T cells. FIG. 12J shows a negative correlation between tumor volume and percentage CD3-CD4-double-positive T cells. FIG. 12K shows a negative correlation between tumor volume and percentage CD3-CD8-double-positive T cells.

FIGS. 13A-13F shows that hypoxic tumor regions are immunosuppressive and exhibit reduced T cell infiltration in subcutaneous 4T1-Luc syngeneic mouse tumors. Immunofluorescence staining of tumor region #1 for (FIG. 13A) pimonidazole-positive hypoxic areas and (FIG. 13B) CD8-positive T cells, counterstained with (FIG. 13C) DAPI to highlight nuclei. Immunofluorescence staining of tumor region #2 for (FIG. 13D) pimonidazole-positive hypoxic areas and (FIG. 13E) CD4-positive T cells, counterstained with (FIG. 13F) DAPI to highlight nuclei.

DETAILED DESCRIPTION OF THE INVENTION

Figure 1A:
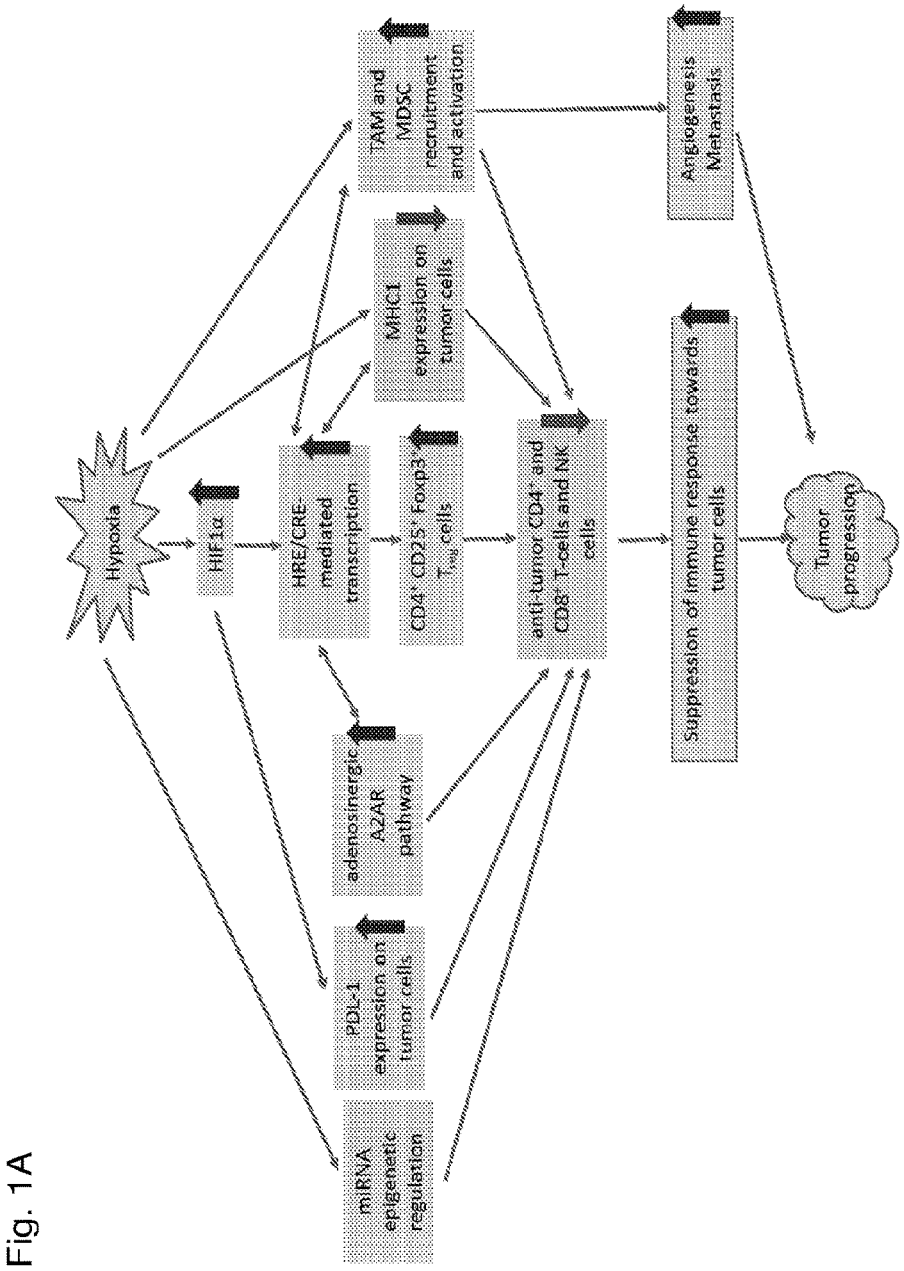
FIGS. 1A and 1B shows a model of the major immunosuppressive pathways promoted by hypoxia (FIG. 1A) and the points of therapeutic intervention that may be exerted by $O_2$ carrier polypeptide treatment (FIG. 1B).

The present invention provides methods for treating cancer in an individual comprising administering to the individual an effective amount of an $O_2$ carrier polypeptide such as an H-NOX protein. In certain aspects, the invention provides methods for modulating hypoxia-mediated tumor immunity in an individual comprising administering to the individual an effective amount of an $O_2$ carrier polypeptide, such as an H-NOX protein. The $O_2$ carrier polypeptide is delivered to the tumor where it enhances an immune response to the tumor. Enhancement of an immune response to the tumor may be mediated by targeting hypoxia inducible factor 1α (HIF-1α)-mediated pathways of tumor immunity and/or non-HIF-1α-mediated pathways of tumor immunity. In some aspects, the invention provides methods for increasing lymphocyte infiltration to a tumor in an individual comprising administering to the individual an effective amount of an $O_2$ carrier polypeptide. In some embodiments, the increase in lymphocyte infiltration to the tumor comprises an increase in infiltration of one or more of CD4 cells, CD8 cells, or NK cells. In some embodiments, the increase in lymphocyte infiltration to the tumor is accompanied by inhibition of one or more of Treg cells, tumor associated macrophages or myeloid derived suppressor cells in the tumor. In some embodiments, the increase in lymphocyte infiltration to the tumor is accompanied by an increase in MHC1 expression on the tumor cells. In some embodiments, the invention provides methods for decreasing expression of hypoxia inducible factor 1α (HIF-1α) in a tumor in an individual comprising administering to the individual an effective amount of an $O_2$ carrier polypeptide (e.g., an H-NOX protein). In some embodiments, the invention provides methods for decreasing expression of programmed death ligand-1 (PD-L1) in a tumor in an individual comprising administering to the individual an effective amount of an $O_2$ carrier polypeptide (e.g., an H-NOX protein). In some embodiments, the invention provides methods for decreasing expression of A2A adenosine receptor (A2AR) in a tumor in an individual comprising administering to the individual an effective amount of an $O_2$ carrier polypeptide (e.g., an H-NOX protein).

Definitions

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

For use herein, unless clearly indicated otherwise, use of the terms "a", "an," and the like refers to one or more.

In this application, the use of "or" means "and/or" unless expressly stated or understood by one skilled in the art. In the context of a multiple dependent claim, the use of "or" refers back to more than one preceding independent or dependent claim.

Reference to "about" a value or parameter herein includes (and describes) embodiments that are directed to that value or parameter per se. For example, description referring to "about X" includes description of "X."

It is understood that aspect and embodiments of the invention described herein include "comprising," "consisting," and "consisting essentially of" aspects and embodiments.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and polymers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification. As used herein, a protein may include two or more subunits, covalently or non-covalently associated; for example, a protein may include two or more associated monomers.

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

As used herein, the term "hypoxia inducible factor" or "HIF" refers to a family of transcription factor that respond to decreases in oxygen, or hypoxia, in the cellular environment. Members of the human HIF family include HIF-1α, HIF-1β, HIF-2α, HIF-2β, HIF3α, HIF3β. HIF-1 functions as a master regulator of homeostatic responses to hypoxia by activating transcription of many genes, including those involved in energy metabolism, angiogenesis, apoptosis, and other genes whose protein products increase oxygen delivery or facilitate metabolic adaptation to hypoxia. HIF-1 plays a role in embryonic vascularization, tumor angiogenesis and pathophysiology of ischemic disease. Human hypoxia-inducible factor 1, alpha subunit or human HIF-1α interacts with a number of polypeptides including but not limited to ARNTL, ARNT, CREBB, EP300, HIF-1AN, Mdm2, NR4A, p53, PSMA7, STAT3, UBC, VH and pVHL. Human HIF-1α is encoded by the HIF-1A gene. The amino acid sequence of human HIF-1α is provided by GenBank Accession no. NP_001230013 and the nucleotide sequence of human HIF-1α mRNA is provided by GenBank Accession No. NM_001243084. The amino acid sequence of mouse HIF-1α is provided by GenBank Accession no. NP_010431 and the nucleotide sequence of mouse HIF-1α mRNA is provided by GenBank Accession No. NM_034561.

As used herein, "programmed death-ligand 1" or "PD-L1" refers to a transmembrane protein that is part of an immune checkpoint pathway that plays a role in suppressing the immune system. Interaction of PDL1 with the PD1 receptor or the B7.1 receptor inhibits T cell receptor-mediated activation of IL-2 and T cell proliferation. Human PD-L1 is encoded by the CD274 gene. The amino acid sequence of human PD-L1 is provided by GenBank Accession no. NP_001254635 and the nucleotide sequence of human PD-L1 mRNA is provided by GenBank Accession No. NM_001267706. The amino acid sequence of mouse PD-L1 is provided by GenBank Accession no. NP_021893 and the nucleotide sequence of mouse PD-L1 mRNA is provided by GenBank Accession No. NM_068693.

As used herein, an "adenosine A2A receptor" or "A2AR" refers to a receptor of the G protein-coupled receptor superfamily. A2AR is a receptor for adenosine that plays a role in oxygen consumption and is thought to play a role in suppressing overreactive immune cells by way or increased levels of cAMP. Human A2AR is encoded by ADORA2A the gene. The amino acid sequence of human A2AR is provided by GenBank Accession no. NP_000666 and the nucleotide sequence of human A2AR mRNA is provided by GenBank Accession No. NM_000675. The amino acid sequence of mouse A2AR is provided by GenBank Accession no. NP_033760 and the nucleotide sequence of mouse A2AR mRNA is provided by GenBank Accession No. NM_09630.

As used herein, an "H-NOX protein" means a protein that has an H-NOX domain (named for Heme-Nitric oxide and OXygen binding domain). An H-NOX protein may or may not contain one or more other domains in addition to the H-NOX domain. In some examples, an H-NOX protein does not comprise a guanylyl cyclase domain. An H-NOX protein may or may not comprise a polymerization domain.

As used herein, a "polymeric H-NOX protein" is an H-NOX protein comprising two or more H-NOX domains. The H-NOX domains may be covalently or non-covalently associated.

As used herein, an "H-NOX domain" is all or a portion of a protein that binds nitric oxide and/or oxygen by way of heme. The H-NOX domain may comprise heme or may be found as an apoproprotein that is capable of binding heme. In some examples, an H-NOX domain includes six alpha-helices, followed by two beta-strands, followed by one alpha-helix, followed by two beta strands. In some examples, an H-NOX domain corresponds to the H-NOX domain of *Thermoanaerobacter tengcongensis* H-NOX set forth in SEQ ID NO:2. For example, the H-NOX domain may be at least about 10%, 15%, 20%, 25%, 30%, 40%, 50%, 60%, 70%, 80%, 90%, 95%, or 99% identical to the H-NOX domain of *Thermoanaerobacter tengcongensis* H-NOX set forth in SEQ ID NO:2. In some embodiments, the H-NOX domain may be 10%-20%, 20%-30%, 30%-40%, 40%-50%, 50%-60%, 60%-70%, 70%-80%, 80%-90%, 90%-95%, 95%-99% or 100% identical to the H-NOX domain of *Thermoanaerobacter tengcongensis* H-NOX set forth in SEQ ID NO:2.

As used herein, a "polymerization domain" is a domain (e.g. a polypeptide domain) that promotes the association of monomeric moieties to form a polymeric structure. For example, a polymerization domain may promote the association of monomeric H-NOX domains to generate a polymeric H-NOX protein. An exemplary polymerization domain is the foldon domain of T4 bacteriophage, which promotes the formation of trimeric polypeptides. Other examples of polymerization domains include, but are not limited to, Arc, POZ, coiled coil domains (including GCN4, leucine zippers, Velcro), uteroglobin, collagen, 3-stranded coiled colis (matrilin-1), thrombosporins, TRPV1-C, P53, Mnt, avadin, streptavidin, Bcr-Abl, COMP, verotoxin subunit B, CamKII, RCK, and domains from N ethylmaleimide-sensitive fusion protein, STM3548, KaiC, TyrR, Hcp1, CcmK4, GP41, anthrax protective antigen, aerolysin, a-hemolysin, C4b-binding protein, Mi-CK, arylsurfatase A, and viral capsid proteins.

As used herein, an "amino acid linker sequence" or an "amino acid spacer sequence" is a short polypeptide sequence that may be used to link two domains of a protein. In some embodiments, the amino acid linker sequence is one, two, three, four, five, six, seven, eight, nine, ten or more than ten amino acids in length. Exemplary amino acid linker sequences include but are not limited to a Gly-Ser-Gly sequence and an Arg-Gly-Ser sequence.

As used herein, a "His$_6$ tag" refers to a peptide comprising six His residues attached to a polypeptide. A His$_6$ tag may be used to facilitate protein purification; for example, using chromatography specific for the His$_6$ tag. Following purification, the His$_6$ tag may be cleaved using an exopeptidase.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially reduced," or "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, or 90%. In some embodiment, the two substantially different numeric values differ by about any one of 10%-20%, 20%-30%, 30%-40%, 40%-50%, 50%-60%, 60%-70%, 70%-80%, 80%-90%, 90%-95%, 95%-99% or 100%.

A "native sequence" polypeptide comprises a polypeptide having the same amino acid sequence as a polypeptide found in nature. Thus, a native sequence polypeptide can have the amino acid sequence of naturally occurring polypeptide from any organism. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about any one of 80%, 90% or 95% amino acid sequence identity with the native sequence polypeptide. In some embodiments, a variant will have about any one of 80%-90%, 90%-95% or 95%-99% amino acid sequence identity with the native sequence polypeptide.

As used herein, a "mutant protein" means a protein with one or more mutations compared to a protein occurring in nature. In one embodiment, the mutant protein has a sequence that differs from that of all proteins occurring in nature. In various embodiments, the amino acid sequence of the mutant protein is at least about any of 10, 15, 20, 25, 30, 40, 50, 60, 70, 80, 90, 95, 97, 98, 99, or 99.5% identical to that of the corresponding region of a protein occurring in nature. In some embodiments, the amino acid sequence of the mutant protein is at least about any of 10%-20%, 20%-30%, 30%-40%, 40%-50%, 50%-60%, 60%-70%, 70%-80%, 80%-90%, 90%-95%, 95%-99% or 100% identical to that of the corresponding region of a protein occurring in nature. In some embodiments, the mutant protein is a protein fragment that contains at least about any of 25, 50, 75, 100, 150, 200, 300, or 400 contiguous amino acids from a full-length protein. In some embodiments, the mutant protein is a protein fragment that contains about any of 25-50, 50-75, 75-100, 100-150, 150-200, 200-300, or 300-400 contiguous amino acids from a full-length protein. Sequence identity can be measured, for example, using sequence analysis software with the default parameters specified therein (e.g., Sequence Analysis Software Package of the Genetics Computer Group, University of Wisconsin Biotechnology Center, 1710 University Avenue, Madison, WI 53705). This software program matches similar sequences by assigning degrees of homology to various amino acids replacements, deletions, and other modifications.

As used herein, a "mutation" means an alteration in a reference nucleic acid or amino acid sequence occurring in nature. Exemplary nucleic acid mutations include an insertion, deletion, frameshift mutation, silent mutation, nonsense mutation, or missense mutation. In some embodiments, the nucleic acid mutation is not a silent mutation. Exemplary protein mutations include the insertion of one or more amino acids (e.g., the insertion of 2, 3, 4, 5, 6, 7, 8, 9, or 10 amino acids), the deletion of one or more amino acids (e.g., a deletion of N-terminal, C-terminal, and/or internal residues, such as the deletion of at least about any of 5, 10, 15, 25, 50, 75, 100, 150, 200, 300, or more amino acids or a deletion of about any of 5-10, 10-15, 15-25, 25-50, 50-75, 75-100, 100-150, 150-200, 200-300, or 300-400 amino acids), the replacement of one or more amino acids (e.g., the replacement of 1, 2, 3, 4, 5, 6, 7, 8, 9, or 10 amino acids), or combinations of two or more of the foregoing. The nomenclature used in referring to a particular amino acid mutation first identifies the wild-type amino acid, followed by the residue number and finally the substitute amino acid.

For example, Y140L means that tyrosine has been replaced by a leucine at residue number 140. Likewise, a variant H-NOX protein may be referred to by the amino acid variations of the H-NOX protein. For example, a *T. tengcongensis* Y140L H-NOX protein refers to a *T. tengcongensis* H-NOX protein in which the tyrosine residue at position number 140 has been replaced by a leucine residue and a *T. tengcongensis* W9F/Y140L H-NOX protein refers to a *T. tengcongensis* H-NOX protein in which the tryptophan residue at position 9 has been replaced by a phenylalanine residue and the tyrosine residue at position number 140 has been replaced by a leucine residue.

An "evolutionary conserved mutation" is the replacement of an amino acid in one protein by an amino acid in the corresponding position of another protein in the same protein family.

As used herein, "derived from" refers to the source of the protein into which one or more mutations is introduced. For example, a protein that is "derived from a mammalian protein" refers to protein of interest that results from introducing one or more mutations into the sequence of a wild-type (i.e., a sequence occurring in nature) mammalian protein.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

As used herein, a "$k_{off}$" refers to a dissociation rate, such as the rate of release of $O_2$ or NO from a protein. A lower numerical lower $k_{off}$ indicates a slower rate of dissociation.

As used herein, "$k_{on}$" refers to an association rate, such as the rate of binding of $O_2$ or NO to a protein. A lower numerical lower $k_{on}$ indicates a slower rate of association.

As used herein, "dissociation constant" refers to a "kinetic dissociation constant" or a "calculated dissociation constant." A "kinetic dissociation constant" or "$K_D$" is a ratio of kinetic off-rate ($k_{off}$) to kinetic on-rate ($k_{on}$), such as a $K_D$ value determined as an absolute value using standard methods (e.g., standard spectroscopic, stopped-flow, or flash-photolysis methods) including methods known to the skilled artisan and/or described herein. "Calculated dissociation constant" or "calculated $K_D$" refers to an approximation of the kinetic dissociation constant based on a measured $k_{off}$. A value for the $k_{on}$ is derived via the correlation between kinetic $K_D$ and $k_{off}$ as described herein.

As used herein, "oxygen affinity" is a qualitative term that refers to the strength of oxygen binding to the heme moiety of a protein. This affinity is affected by both the $k_{off}$ and $k_{on}$ for oxygen. A numerically lower oxygen $K_D$ value means a higher affinity.

As used herein, "NO affinity" is a qualitative term that refers to the strength of NO binding to a protein (such as binding to a heme group or to an oxygen bound to a heme group associated with a protein). This affinity is affected by both the $k_{off}$ and $k_{on}$ for NO. A numerically lower NO $K_D$ value means a higher affinity.

As used herein, "NO stability" refers to the stability or resistance of a protein to oxidation by NO in the presence of oxygen. For example, the ability of the protein to not be oxidized when bound to NO in the presence of oxygen is indicative of the protein's NO stability. In some embodiments, less than about any of 50, 40, 30, 10, or 5% of an H-NOX protein is oxidized after incubation for about any of 1, 2, 4, 6, 8, 10, 15, or 20 hours at 20° C.

As used herein, "NO reactivity" refers to the rate at which iron in the heme of a heme-binding protein is oxidized by NO in the presence of oxygen. A lower numerical value for NO reactivity in units of $s^{-1}$ indicates a lower NO reactivity As used herein, an "autoxidation rate" refers to the rate at which iron in the heme of a heme-binding protein is autoxidized. A lower numerical autoxidation rate in units of $s^{-1}$ indicates a lower autoxidation rate.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Exemplary prokaryotic cells include bacterial cells; for example, *E. coli* cells.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder.

A "disease" or "disorder" as used herein refers to a condition where treatment is needed.

The term "cancer" refers to a malignant proliferative disorder associated with uncontrolled cell proliferation, unrestrained cell growth, and decreased cell death via apoptosis.

The term "tumor" is used herein to refer to a group of cells that exhibit abnormally high levels of proliferation and growth. A tumor may be benign, pre-malignant, or malignant; malignant tumor cells are cancerous. Tumor cells may be solid tumor cells or leukemic tumor cells. The term "tumor growth" is used herein to refer to proliferation or growth by a cell or cells that comprise a tumor that leads to a corresponding increase in the size of the tumor.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment. Also encompassed by "treatment" is a reduction of pathological consequence of a proliferative disease. The methods of the invention contemplate any one or more of these aspects of treatment.

In the context of cancer, the term "treating" includes any or all of: inhibiting growth of tumor cells or cancer cells, inhibiting replication of tumor cells or cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or 99%.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

"Preventing," as used herein, includes providing prophylaxis with respect to the occurrence or recurrence of a disease in a subject that may be predisposed to the disease but has not yet been diagnosed with the disease.

An "effective amount" of an agent refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile and essentially free of endotoxins.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

H-NOX Proteins

Overview of H-NOX Protein Family

Unless otherwise indicated, any wild-type or mutant H-NOX protein can be used in the compositions, kits, and methods as described herein. As used herein, an "H-NOX protein" means a protein that has an H-NOX domain (named for Heme-Nitric oxide and OXygen binding domain). An H-NOX protein may or may not contain one or more other domains in addition to the H-NOX domain. H-NOX proteins are members of a highly-conserved, well-characterized family of hemoproteins (Iyer, L. M. et al. (Feb. 3, 2003). *BMC Genomics* 4 (1): 5; Karow, D. S. et al. (Aug. 10, 2004). *Biochemistry* 43 (31): 10203-10211; Boon, E. M. et al. (2005). *Nature Chem. Biol.* 1:53-59; Boon, E. M. et al. (October 2005). *Curr. Opin. Chem. Biol.* 9 (5): 441-446; Boon, E. M. et al. (2005). *J. Inorg. Biochem.* 99 (4): 892-902). H-NOX proteins are also referred to as Pfam 07700 proteins or HNOB proteins (Pfam-A database of protein domain family alignments and Hidden Markov Models, Copyright (C) 1996-2006 The Pfam Consortium; GNU LGPL Free Software Foundation, Inc., 59 Temple Place-Suite 330, Boston, MA 02111-1307, USA). In some embodiments, an H-NOX protein has, or is predicted to have, a secondary structure that includes six alpha-helices, followed by two beta-strands, followed by one alpha-helix, followed by two beta-strands. An H-NOX protein can be an apoprotein that is capable of binding heme or a holoprotein with heme bound. An H-NOX protein can covalently or non-covalently bind a heme group. Some H-NOX proteins bind NO but not $O_2$, and others bind both NO and $O_2$. H-NOX domains from facultative aerobes that have been isolated bind NO but not $O_2$. H-NOX proteins from obligate aerobic prokaryotes, *C. elegans*, and *D. melanogaster* bind NO and $O_2$. Mammals have two H-NOX proteins: β1 and β2. An alignment of mouse, rat, cow, and human H-NOX sequences shows that these species share >99% identity. In some embodiments, the H-NOX domain of an H-NOX protein or the entire H-NOX protein is at least about any of 10, 15, 20, 25, 30, 40, 50, 60, 70, 80, 90, 95, 97, 98, 99, or 99.5% identical to that of the corresponding region of a naturally-occurring *Thermoanaerobacter tengcongensis* H-NOX protein (e.g. SEQ ID NO:2) or a naturally-occurring sGC protein (e.g., a naturally-occurring sGC β1 protein). In some embodiments, the H-NOX domain of an H-NOX protein or the entire H-NOX protein is at least about any of 10-20%, 20-30%, 30-40%, 40-50%, 50-60%, 60-70%, 70-80%, 80-90%, 90-95%, 95-99, or 99-99.9% identical to that of the corresponding region of a naturally-occurring *Thermoanaerobacter tengcongensis* H-NOX protein (e.g. SEQ ID NO: 2) or a naturally-occurring sGC protein (e.g., a naturally-occurring sGC β1 protein). As discussed further herein, an H-NOX protein may optionally contain one or more mutations relative to the corresponding naturally-occurring H-NOX protein. In some embodiments, the H-NOX protein includes one or more domains in addition to the H-NOX domain. In particular embodiments, the H-NOX protein includes one or more domains or the entire sequence from another protein. For example, the H-NOX protein may be a fusion protein that includes an H-NOX domain and part or all of another protein, such as albumin (e.g., human serum albumin). In some embodiments, only the H-NOX domain is present. In some embodiments, the H-NOX protein does not comprise a guanylyl cyclase domain. In some embodiments, the H-NOX protein comprises a tag; for example, a $His_6$ tag.

Polymeric H-NOX Proteins

In some aspects, the invention provides polymeric H-NOX proteins comprising two or more H-NOX domains. The two or more H-NOX domains may be covalently linked or noncovalently linked. In some embodiments, the polymeric H-NOX protein is in the form of a dimer, a trimer, a tetramer, a pentamer, a hexamer, a heptamer, an octomer, a nanomer, or a decamer. In some embodiments, the polymeric H-NOX protein comprises homologous H-NOX domains. In some embodiments, the polymeric H-NOX protein comprises heterologous H-NOX domains; for example, the H-NOX domains may comprises amino acid variants of a particular species of H-NOX domain or may comprise H-NOX domains from different species. In some embodiments, at least one of the H-NOX domains of a polymeric H-NOX protein comprises a mutation corresponding to an L144F mutation of *T. tengcongensis* H-NOX. In some embodiments, at least one of the H-NOX domains of a polymeric H-NOX protein comprises a mutation corresponding to a W9F/L144F mutation of *T. tengcongensis* H-NOX. In some embodiments, the polymeric H-NOX proteins comprise one or more polymerization domains. In some embodiments, the polymeric H-NOX protein is a trimeric H-NOX protein. In some embodiments, the polymeric H-NOX protein comprises at least one trimerization domain. In some embodiments, the trimeric H-NOX protein comprises three *T. tengcongensis* H-NOX domains. In some embodiments the trimeric H-NOX domain comprises three *T. tengcongensis* L144F H-NOX domains (trimeric Tt H-NOX L144F). In some embodiments the trimeric H-NOX domain comprises three *T. tengcongensis* W9F/L144F H-NOX domains In some aspects of the invention, the polymeric H-NOX protein comprises two or more associated monomers. The monomers may be covalently linked or noncovalently linked. In some embodiments, monomeric subunits of a polymeric H-NOX protein are produced where the monomeric subunits associate in vitro or in vivo to form the polymeric H-NOX protein. In some embodiments, the monomers comprise an H-NOX domain and a polymerization domain. In some embodiments, the polymerization domain is covalently linked to the H-NOX domain; for example, the C-terminus of the H-NOX domain is covalently linked to the N-terminus or the C-terminus of the polymerization domain. In other embodiments, the N-terminus of the H-NOX domain is covalently linked to the N-terminus or the C-terminus of the polymerization domain. In some embodiments, an amino acid spacer is covalently linked between the H-NOX domain and the polymerization domain. An "amino acid spacer" and an "amino acid linker" are used interchangeably herein. In some embodiments, at least one of the monomeric subunits of a polymeric H-NOX protein comprises a mutation corresponding to an L144F mutation of *T. tengcongensis* H-NOX. In some embodiments, at least one of the monomeric subunits of a polymeric H-NOX protein comprises a mutation corresponding to a W9F/L144F mutation of *T. tengcongensis* H-NOX. In some embodiments the polymeric H-NOX protein is a trimeric H-NOX protein. In some embodiments, the monomer of a trimeric H-NOX protein comprises an H-NOX domain and a foldon domain of T4 bacteriophage. In some embodiments, the monomer of a trimeric H-NOX protein comprises a *T. tengcongensis* H-NOX domain and a foldon domain. In some embodiments, the monomer of a trimeric H-NOX protein comprises a *T. tengcongensis* L144F H-NOX domain and a foldon domain. In some embodiments, the monomer of a trimeric H-NOX protein comprises a *T. tengcongensis* W9F/L144F H-NOX domain and a foldon domain. In some embodiments, the trimer H-NOX protein comprises three monomers, each monomer comprising a *T. tengcongensis* L144F H-NOX domain and a foldon domain. In some embodiments, the H-NOX domain is linked to the foldon domain with an amino acid linker; for example a Gly-Ser-Gly linker. In some embodiments, at least one H-NOX domain comprises a tag. In some embodiments, at least one H-NOX domain comprises a $His_6$ tag. In some embodiments, the $His_6$ tag is linked to the foldon domain with an amino acid linker; for example an Arg-Gly-Ser linker. In some embodiments, all of the H-NOX domains comprise a $His_6$ tag. In some embodiments, the trimeric H-NOX protein comprises the amino acid sequence set forth in SEQ ID NO:6 or SEQ ID NO:8.

The exemplary H-NOX domain from *T. tengcongensis* is approximately 26.7 kDal. In some embodiments, the polymeric H-NOX protein has an atomic mass greater than any of about 50 kDal, 75 kDal, 100 kDal, 125 kDal, to about 150 kDal.

The invention provides polymeric H-NOX proteins that show greater accumulation in one or more tissues in an individual compared to a corresponding monomeric H-NOX protein comprising a single H-NOX domain following administration of the H-NOX protein to the individual. A corresponding H-NOX protein refers to a monomeric form of the H-NOX protein comprising at least one of the H-NOX domains of the polymeric H-NOX protein. Tissues of preferential polymeric H-NOX accumulation include, but are not limited to tumors and tissue with damaged vasculature. In some embodiments the polymeric H-NOX protein persists in a mammal for at least about 1, 2, 3, 4, 6, 12 or 24 hours following administration of the H-NOX protein to the individual. In some embodiments the polymeric H-NOX protein persists in a mammal for about 1-2, 2-3, 3-4, 4-6, 6-12 or 12-24 hours following administration of the H-NOX protein to the individual In some embodiments, less than about 10% of the polymeric H-NOX is cleared from mammal by the kidneys within less than any of about 1 hour, 2 hours or 3 hours following administration of the H-NOX protein to the individual.

Sources of H-NOX Proteins and H-NOX Domains

H-NOX proteins and H-NOX domains from any genus or species can be used in the compositions, kits, and methods described herein. In various embodiments, the H-NOX protein or the H-NOX domains of a polymeric H-NOX protein is a protein or domain from a mammal (e.g., a primate (e.g., human, monkey, gorilla, ape, lemur, etc), a bovine, an equine, a porcine, a canine, or a feline), an insect, a yeast, or a bacteria or is derived from such a protein. Exemplary mammalian H-NOX proteins include wild-type human and rat soluble guanylate cyclase (such as the β1 subunit). Non-limiting examples of H-NOX proteins include wild-type mammalian H-NOX proteins, e.g. *H. sapiens, M.*

*musculus, C. familiaris, B. Taurus, C. lupus* and *R. norvegicus* and examples of prokaryotic wild-type H-NOX proteins include *T. tengcongensis, V. cholera, V. fischerii, N. punctiforme, D. desulfuricans, L. pneumophila* 1, *L. pneumophila* 2, and *C. acetobutylicum*. Examples of H-NOX proteins including their NCBI accession numbers may be found in U.S. Pat. Nos. 8,404,631 and 8,404,632, WO 2007/139791 and WO 2007/139767; the contents of each is incorporated herein by reference in its entirety.

Additional H-NOX proteins, H-NOX domains of polymeric H-NOX proteins, and nucleic acids, which may be suitable for use in the pharmaceutical compositions and methods described herein, can be identified using standard methods. For example, standard sequence alignment and/or structure prediction programs can be used to identify additional H-NOX proteins and nucleic acids based on the similarity of their primary and/or predicted protein secondary structure with that of known H-NOX proteins and nucleic acids. For example, the Pfam database uses defined alignment algorithms and Hidden Markov Models (such as Pfam 21.0) to categorize proteins into families, such as the H-NOX protein family (Pfam-A database of protein domain family alignments and Hidden Markov Models, Copyright (C) 1996-2006 The Pfam Consortium; GNU LGPL Free Software Foundation, Inc., 59 Temple Place-Suite 330, Boston, MA 02111-1307, USA). Standard databases such as the swissprot-trembl database (world-wide web at "expasy.org", Swiss Institute of Bioinformatics Swiss-Prot group CMU-1 rue Michel Servet CH-1211 Geneva 4, Switzerland) can also be used to identify members of the H-NOX protein family. The secondary and/or tertiary structure of an H-NOX protein can be predicted using the default settings of standard structure prediction programs, such as PredictProtein (630 West, 168 Street, BB217, New York, N.Y. 10032, USA). Alternatively, the actual secondary and/or tertiary structure of an H-NOX protein can be determined using standard methods.

In some embodiments, the H-NOX domain has the same amino acid in the corresponding position as any of following distal pocket residues in *T. tengcongensis* H-NOX: Thr4, Ile5, Thr8, Trp9, Trp67, Asn74, Ile75, Phe78, Phe82, Tyr140, Leu144, or any combination of two or more of the foregoing. In some embodiments, the H-NOX domain has a proline or an arginine in a position corresponding to that of Pro115 or Arg135 of *T. tengcongensis* H-NOX, respectively, based on sequence alignment of their amino acid sequences. In some embodiments, the H-NOX domain has a histidine that corresponds to His105 of *R. norvegicus* β1 H-NOX. In some embodiments, the H-NOX domain has or is predicted to have a secondary structure that includes six alpha-helices, followed by two beta-strands, followed by one alpha-helix, followed by two beta-strands. This secondary structure has been reported for H-NOX proteins.

If desired, a newly identified H-NOX protein or H-NOX domain can be tested to determine whether it binds heme using standard methods. The ability of an H-NOX domain to function as an $O_2$ carrier can be tested by determining whether the H-NOX domain binds $O_2$ using standard methods, such as those described herein. If desired, one or more of the mutations described herein can be introduced into the H-NOX domain to optimize its characteristics as an $O_2$ carrier. For example, one or more mutations can be introduced to alter its $O_2$ dissociation constant, $k_{off}$ for oxygen, rate of heme autoxidation, NO reactivity, NO stability or any combination of two or more of the foregoing. Standard techniques such as those described herein can be used to measure these parameters.

Mutant H-NOX Proteins

As discussed further herein, an H-NOX protein or an H-NOX domain of a polymeric H-NOX protein may contain one or more mutations, such as a mutation that alters the $O_2$ dissociation constant, the $k_{off}$ for oxygen, the rate of heme autoxidation, the NO reactivity, the NO stability, or any combination of two or more of the foregoing compared to that of the corresponding wild-type protein. In some embodiments, the invention provides a polymeric H-NOX protein comprising one or more H-NOX domains that may contain one or more mutations, such as a mutation that alters the $O_2$ dissociation constant, the $k_{off}$ for oxygen, the rate of heme autoxidation, the NO reactivity, the NO stability, or any combination of two or more of the foregoing compared to that of the corresponding wild-type protein. Panels of engineered H-NOX domains may be generated by random mutagenesis followed by empirical screening for requisite or desired dissociation constants, dissociation rates, NO-reactivity, stability, physio-compatibility, or any combination of two or more of the foregoing in view of the teaching provided herein using techniques as described herein and, additionally, as known by the skilled artisan. Alternatively, mutagenesis can be selectively targeted to particular regions or residues such as distal pocket residues apparent from the experimentally determined or predicted three-dimensional structure of an H-NOX protein (see, for example, Boon, E. M. et al. (2005). *Nature Chemical Biology* 1:53-59, which is hereby incorporated by reference in its entirety, particularly with respect to the sequences of wild-type and mutant H-NOX proteins) or evolutionarily conserved residues identified from sequence alignments (see, for example, Boon E. M. et al. (2005). *Nature Chemical Biology* 1:53-59, which is hereby incorporated by reference in its entirety, particularly with respect to the sequences of wild-type and mutant H-NOX proteins).

In some embodiments of the invention, the mutant H-NOX protein or mutant H-NOX domain of a polymeric H-NOX protein has a sequence that differs from that of all H-NOX proteins or domains occurring in nature. In various embodiments, the amino acid sequence of the mutant protein is at least about any of 10, 15, 20, 25, 30, 40, 50, 60, 70, 80, 90, 95, 97, 98, 99, or 99.5% identical to that of the corresponding region of an H-NOX protein occurring in nature. In various embodiments, the amino acid sequence of the mutant protein is about 10-20%, 20-30%, 30-40%, 40-50%, 50-60%, 60-70%, 70-80%, 80-90%, 90-95%, 95-99%, or 99.5% identical to that of the corresponding region of an H-NOX protein occurring in nature. In some embodiments, the mutant protein is a protein fragment that contains at least about any of 25, 50, 75, 100, 150, 200, 300, or 400 contiguous amino acids from a full-length protein. In some embodiments, the mutant protein is a protein fragment that contains 25-50, 50-75, 75-100, 100-150, 150-200, 200-300, or 300-400 contiguous amino acids from a full-length protein. Sequence identity can be measured, for example, using sequence analysis software with the default parameters specified therein (e.g., Sequence Analysis Software Package of the Genetics Computer Group, University of Wisconsin Biotechnology Center, 1710 University Avenue, Madison, WI 53705). This software program matches similar sequences by assigning degrees of homology to various amino acids replacements, deletions, and other modifications.

In some embodiments of the invention, the mutant H-NOX protein or mutant H-NOX domain of a polymeric H-NOX protein comprises the insertion of one or more amino acids (e.g., the insertion of 2, 3, 4, 5, 6, 7, 8, 9, or 10 amino acids). In some embodiments of the invention, the mutant H-NOX protein or mutant H-NOX domain comprises the deletion of one or more amino acids (e.g., a deletion of N-terminal, C-terminal, and/or internal residues, such as the deletion of at least about any of 5, 10, 15, 25, 50, 75, 100, 150, 200, 300, or more amino acids or a deletion of 5-10, 10-15, 15-25, 25-50, 50-75, 75-100, 100-150, 150-200, 200-300, or 300-400 amino acids). In some embodiments of the invention, the mutant H-NOX protein or mutant H-NOX domain comprises the replacement of one or more amino acids (e.g., the replacement of 1, 2, 3, 4, 5, 6, 7, 8, 9, or 10 amino acids), or combinations of two or more of the foregoing. In some embodiments, a mutant protein has at least one amino acid alteration compared to a protein occurring in nature. In some embodiments, a mutant nucleic acid sequence encodes a protein that has at least one amino acid alteration compared to a protein occurring in nature. In some embodiments, the nucleic acid is not a degenerate version of a nucleic acid occurring in nature that encodes a protein with an amino acid sequence identical to a protein occurring in nature.

In some embodiments the mutation in the H-NOX protein or H-NOX domain of a polymeric H-NOX protein is an evolutionary conserved mutations (also denoted class I mutations). Examples of class I mutations are listed in Table 1A. In Table 1A, mutations are numbered/annotated according to the sequence of human β1 H-NOX, but are analogous for all H-NOX sequences. Thus, the corresponding position in any other H-NOX protein can be mutated to the indicated residue. For example, Phe4 of human β1 H-NOX can be mutated to a tyrosine since other H-NOX proteins have a tyrosine in this position. The corresponding phenylalanine residue can be mutated to a tyrosine in any other H-NOX protein. In particular embodiments, the one or more mutations are confined to evolutionarily conserved residues. In some embodiments, the one or more mutations may include at least one evolutionarily conserved mutation and at least one non-evolutionarily conserved mutation. If desired, these mutant H-NOX proteins are subjected to empirical screening for NO/$O_2$ dissociation constants, NO-reactivity, stability, and physio-compatibility in view of the teaching provided herein.

TABLE 1A

Exemplary Class I H-NOX mutations
targeting evolutionary conserved residues

| F4Y | Q30G | I145Y |
| F4L | E33PI145H | |
| H7G | N61G | K151E |
| A8E | C78H | I157F |
| L9W | A109F | E183F |

In some embodiments, the mutation is a distal pocket mutation, such as mutation of a residue in alpha-helix A, D, E, or G (Pellicena, P. et al. (Aug. 31, 2004). *Proc Natl. Acad Sci USA* 101 (35): 12854-12859). Exemplary distal pocket mutations (also denoted class II mutations) are listed in Table 1B. In Table 1B, mutations are numbered/annotated according to the sequence of human B1 H-NOX, but are analogous for all H-NOX sequences. Because several substitutions provide viable mutations at each recited residue, the residue at each indicated position can be changed to any other naturally or non-naturally-occurring amino acid (denoted "X"). Such mutations can produce H-NOX proteins with a variety of desired affinity, stability, and reactivity characteristics.

TABLE 1B

Exemplary Class II H-NOX
mutations targeting distal pocket residues

| V8X | M73X | I145X |
| L9X | F77X | I149X |
| F70X | C78X | |

In particular embodiments, the mutation is a heme distal pocket mutation. As described herein, a crucial molecular determinant that prevents $O_2$ binding in NO-binding members of the H-NOX family is the lack of a H-bond donor in the distal pocket of the heme. Accordingly, in some embodiments, the mutation alters H-bonding between the H-NOX domain and the ligand within the distal pocket. In some embodiments, the mutation disrupts an H-bond donor of the distal pocket and/or imparts reduced $O_2$ ligand-binding relative to the corresponding wild-type H-NOX domain. Exemplary distal pocket residues include Thr4, Ile5, Thr8, Trp9, Trp67, Asn74, Ile75, Phe78, Phe82, Tyr140, and Leu144 of *T. tengcongensis* H-NOX and the corresponding residues in any other H-NOX protein. In some embodiments, the H-NOX protein or H-NOX domain of a polymeric H-NOX protein comprises one or more distal pocket mutations. In some embodiments, the H-NOX protein or H-NOX domain of a polymeric H-NOX protein comprises one, two, three, four, five, six, seven, eight, nine, ten or more than ten distal pocket mutations. In some embodiments, the distal pocket mutation corresponds to a L144F mutation of *T. tengcongensis* H-NOX. In some embodiments, the distal pocket mutation is a L144F mutation of *T. tengcongensis* H-NOX. In some embodiments, H-NOX protein or the H-NOX domain of a polymeric H-NOX protein comprises two distal pocket mutations. In some embodiments, the H-NOX protein or H-NOX domain of a polymeric H-NOX protein corresponds to a W9F/L144F mutation of *T. tengcongensis* H-NOX. In some embodiments, the H-NOX protein or H-NOX domain of a polymeric H-NOX protein is a W9F/L144F mutation of *T. tengcongensis* H-NOX.

Residues that are not in the distal pocket can also affect the three-dimensional structure of the heme group; this structure in turn affects the binding of $O_2$ and NO to iron in the heme group. Accordingly, in some embodiments, the H-NOX protein or H-NOX domain of a polymeric H-NOX protein has one or more mutations outside of the distal pocket. Examples of residues that can be mutated but are not in the distal pocket include Pro115 and Arg135 of *T. tengcongensis* H-NOX. In some embodiments, the mutation is in the proximal pocket which includes His105 as a residue that ligates to the heme iron.

In some embodiments when two or more mutations are present; at least one mutation is in the distal pocket, and at least one mutation is outside of the distal pocket (e.g., a mutation in the proximal pocket). In some embodiments, all the mutations are in the distal pocket.

To reduce the immunogenicity of H-NOX protein or H-NOX domains derived from sources other than humans, amino acids in an H-NOX protein or H-NOX domain can be mutated to the corresponding amino acids in a human H-NOX. For example, one or more amino acids on the surface of the tertiary structure of a non-human H-NOX protein or H-NOX domain can be mutated to the corresponding amino acid in a human H-NOX protein or H-NOX domain. In some variations, mutation of one or more surface amino acids may be combined with mutation of two or more distal pocket residues, mutation of one or more residues outside of the distal pocket (e.g., a mutation in the proximal pocket), or combinations of two or more of the foregoing.

The invention also relates to any combination of mutation described herein, such as double, triple, or higher multiple mutations. For example, combinations of any of the mutations described herein can be made in the same H-NOX protein. Note that mutations in equivalent positions in other mammalian or non-mammalian H-NOX proteins are also encompassed by this invention. Exemplary mutant H-NOX proteins or mutant H-NOX domains comprise one or more mutations that impart altered $O_2$ or NO ligand-binding relative to the corresponding wild-type H-NOX domain and are operative as a physiologically compatible mammalian $O_2$ blood gas carrier.

The residue number for a mutation indicates the position in the sequence of the particular H-NOX protein being described. For example, *T. tengcongensis* I5A refers to the replacement of isoleucine by alanine at the fifth position in *T. tengcongensis* H-NOX. The same isoleucine to alanine mutation can be made in the corresponding residue in any other H-NOX protein or H-NOX domain (this residue may or may not be the fifth residue in the sequence of other H-NOX proteins). Since the amino acid sequences of mammalian β1 H-NOX domains differ by at most two amino acids, mutations that produce desirable mutant H-NOX proteins or H-NOX domains when introduced into wild-type rat B1 H-NOX proteins are also expected to produce desirable mutant H-NOX proteins or H-NOX domains when introduced into wild-type B1 H-NOX proteins or H-NOX domains from other mammals, such as humans.

In some embodiments, the H-NOX protein is a trimer comprising three *T. tengcongensis* L144F H-NOX domains and three foldon domains. In some embodiments, the H-NOX protein is a trimer comprising three *T. tengcongensis* W9F/L144F H-NOX domains and three foldon domains. In some embodiments, the H-NOX protein is a trimer comprising three *T. tengcongensis* wildtype H-NOX domains and three foldon domains.

Modifications to H-NOX Proteins

Any of the wild-type or mutant H-NOX proteins, including polymeric H-NOX proteins, can be modified and/or formulated using standard methods to enhance therapeutic or industrial applications. For example, and particularly as applied to heterologous engineered H-NOX proteins, a variety of methods are known in the art for insulating such agents from immune surveillance, including crosslinking, PEGylation, carbohydrate decoration, etc. (e.g., Rohlfs, R. J. et al. (May 15, 1998). *J. Biol. Chem.* 273 (20): 12128-12134; Migita, R. et al. (June 1997). *J. Appl. Physiol.* 82 (6): 1995-2002; Vandegriff, K. D. et al. (Aug. 15, 2004). *Biochem J.* 382 (Pt 1): 183-189, which are each hereby incorporated by reference in their entireties, particularly with respect to the modification of proteins) as well as other techniques known to the skilled artisan. Fusing an H-NOX protein, including a polymeric H-NOX protein, with a human protein such as human serum albumin can increase the serum half-life, viscosity, and colloidal oncotic pressure. In some embodiments, an H-NOX protein is modified during or after its synthesis to decrease its immunogenicity and/or to increase its plasma retention time. H-NOX proteins can also be encapsulated (such as encapsulation within liposomes or nanoparticles).

In some embodiments, the H-NOX protein comprises one of more tags; e.g. to assist in purification of the H-NOX protein. Examples of tags include, but are not limited to $His_6$, FLAG, GST, and MBP. In some embodiments, the H-NOX protein comprises one of more $His_6$ tags. The one or more $His_6$ tags may be removed prior to use of the polymeric H-NOX protein; e.g. by treatment with an exopeptidase. In some embodiments, the H-NOX protein is a trimer comprising three *T. tengcongensis* L144F H-NOX domains, three foldon domains, and three $His_6$ tags. In some embodiments, the H-NOX protein is a trimer comprising three *T. tengcongensis* W9F/L144F H-NOX domains, three foldon domains, and three $His_6$ tags. In some embodiments, the H-NOX protein is a trimer comprising three *T. tengcongensis* wildtype H-NOX domains, three foldon domains, and three $His_6$ tags.

In some embodiments, the H-NOX protein comprises one or more polyethylene glycol (PEG) molecules (i.e., is PEGylated). In some embodiments, the H-NOX protein is a trimer comprising three *T. tengcongensis* L144F H-NOX domains, three foldon domains, and one or more polyethylene glycol molecules (PEGylated trimer Tt H-NOX L144F). In some embodiments, the H-NOX protein is a trimer comprising three *T. tengcongensis* W9F/L144F H-NOX domains, three foldon domains, and one or more polyethylene glycol molecules. In some embodiments, the H-NOX protein is a trimer comprising three *T. tengcongensis* wildtype H-NOX domains, three foldon domains, and one or more polyethylene glycol molecules. In some embodiments, the molecular weight of the PEG is between about 1 kDa and about 50 kDa. In some emobodiments, the molecular weight of the PED is between about any of 1 kDa and 50 kDa, 1 kDa and 40 kDa, 1 kDa and 30 kDa, 1 kDa and 25 kDa, 1 kDa and 20 kDa, 1 kDa and 15 kDa, 1 kDa and 10 kDa, 1 kDa and 5 kDa, 5 kDa and 50 kDa, 5 kDa and 40 kDa, 5 kDa and 30 kDa, 5 kDa and 25 kDa, 5 kDa and 20 kDa, 5 kDa and 15 kDa, 5 kDa and 10 kDa, 10 kDa and 50 kDa, 10 kDa and 40 kDa, 10 kDa and 30 kDa, 10 kDa and 25 kDa, 10 kDa and 20 kDa, 10 kDa and 15 kDa, 15 kDa and 50 kDa, 15 kDa and 40 kDa, 15 kDa and 35 kDa, 15 kDa and 30 kDa, 15 kDa and 25 kDa, 15 kDa and 20 kDa, 20 kDa and 50 kDa, 20 kDa and 40 kDa, 20 kDa and 30 kDa, 20 kDa and 25 kDa, 25 kDa and 50 kDa, 25 kDa and 40 kDa, 25 kDa and 30 kDa, 30 kDa and 50 kDa, 30 kDa and 40 kDa, or 40 kDa and 50 kDa. In some embodiments, the H-NOX protein comprises any one of more than about 1, 2, 3, 4, 5, 6, 7, 8, 9, 10, 15, 20, 25, 30, 35, 40, 45, or 50 PEG molecules per H-NOX monomer or any number therebetween. In some embodiments, the H-NOX protein comprises an average of 1, 2, 3, 4, 5, 6, 7, 8, 9, 10, 15, 20, 25, 30, 35, 40, 45, or 50 PEG molecules per H-NOX monomer or any number therebetween.

Polymerization Domains

In some aspects, the invention provides polymeric H-NOX proteins comprising two or more H-NOX domains and one or more polymerization domains. Polymerization domains are used to link two or more H-NOX domains to form a polymeric H-NOX protein. One or more polymerization domains may be used to produce dimers, trimers, tetramers, pentamers, etc. of H-NOX proteins. Polymerization domains are known in the art, such as: the foldon of T4 bacteriophage fibritin, Arc, POZ, coiled coil domains (including GCN4, leucine zippers, Velcro), uteroglobin, collagen, 3-stranded coiled colis (matrilin-1), thrombosporins, TRPV1-C, P53, Mnt, avadin, streptavidin, Bcr-Abl, COMP, verotoxin subunit B, CamKII, RCK, and domains from N ethylmaleimide-sensitive fusion protein, STM3548, KaiC, TyrR, Hcp1, CcmK4, GP41, anthrax protective antigen, aerolysin, a-hemolysin, C4b-binding protein, Mi-CK, arylsurfatase A, and viral capsid proteins. The polymerization domains may be covalently or non-covalently linked to the H-NOX domains. In some embodiments, a polymerization domain is linked to an H-NOX domain to form a monomer subunit such that the polymerization domains from a plurality of monomer subunits associate to form a polymeric H-NOX domain. In some embodiments, the C-terminus of an H-NOX domain is linked to the N-terminus of a polymerization domain. In other embodiments, the N-terminus of an H-NOX domain is linked to the N-terminus of a polymerization domain. In yet other embodiments, the C-terminus of an H-NOX domain is linked to the C-terminus of a polymerization domain. In some embodiments, the N-terminus of an H-NOX domain is linked to the C-terminus of a polymerization domain.

Linkers may be used to join a polymerization domain to an H-NOX domain; for example, for example, amino acid linkers. In some embodiments, a linker comprising any one of one, two, three, four, five, six, seven, eight, nine, ten or more than ten amino acids may be placed between the polymerization domain and the H-NOX domain. Exemplary linkers include but are not limited to Gly-Ser-Gly and Arg-Gly-Ser linkers.

Bacteriophage T4 Fibritin Trimerization Domain

Figure 1B:
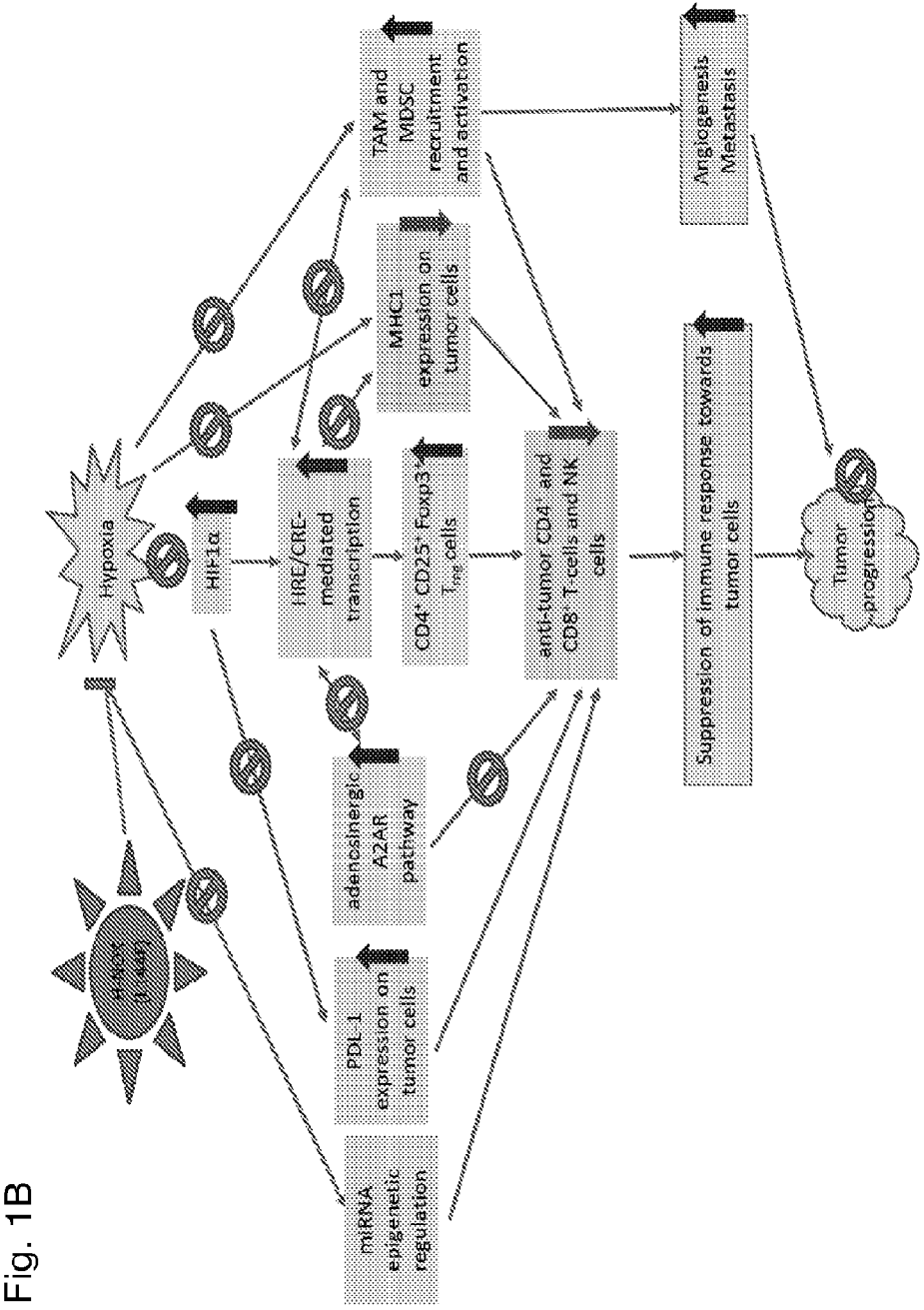

An exemplary polymerization domain is the foldon domain of bacteriophage T4. The wac gene from the bacteriophage T4 encodes the fibritin protein, a 486 amino acid protein with a C-terminal trimerization domain (residues 457-483) (Efimov, V. P. et al. (1994) *J Mol Biol* 242:470-486). The domain is able to trimerize fibritin both in vitro and in vivo (Boudko, S. P. et al. (2002) *Eur J Biochem* 269:833-841; Letarov, A. V., et al., (1999) *Biochemistry (Mosc)* 64:817-823; Tao, Y., et al., (1997) *Structure* 5:789-798). The isolated 27 residue trimerization domain, often referred to as the "foldon domain," has been used to construct chimeric trimers in a number of different proteins (including HIV envelope glycoproteins (Yang, X. et al., (2002) *J Virol* 76:4634-4642), adenoviral adhesins (Papanikolopoulou, K., et al., (2004) *J Biol Chem* 279:8991-8998; Papanikolopoulou, K. et al. (2004) *J Mol Biol* 342:219-227), collagen (Zhang, C., et al. (2009) *Biotechnol Prog* 25:1660-1668), phage P22 gp26 (Bhardwaj, A., et al. (2008) *Protein Sci* 17:1475-1485), and rabies virus glycoprotein (Sissoeff, L., et al. (2005) *J Gen Virol* 86:2543-2552). An exemplary sequence of the foldon domain is shown in FIG. 1 and provided by SEQ ID NO:4.

The isolated foldon domain folds into a single β-hairpin structure and trimerizes into a β-propeller structure involving three hairpins (Guthe, S. et al. (2004) *J Mol Biol* 337:905-915). The structure of the foldon domain alone has been determined by NMR (Guthe, S. et al. (2004) *J Mol Biol* 337:905-915) and the structures of several proteins trimerized with the foldon domain have been solved by X-ray crystallography (Papanikolopoulou, K., et al., (2004) *J Biol Chem* 279:8991-8998; Stetefeld, J. et al. (2003) *Structure* 11:339-346; Yokoi, N. et al. (2010) *Small* 6:1873-1879). The domain folds and trimerizes rapidly reducing the opportunity for misfolding intermediates or off-pathway oligomerization products (Guthe, S. et al. (2004) *J Mol Biol* 337: 905-915). The foldon domain is very stable, able to maintain tertiary structure and oligomerization in >10% SDS, 6.0M guanidine hydrochloride, or 80° C. (Bhardwaj, A., et al. (2008) *Protein Sci* 17:1475-1485; Bhardwaj, A., et al. (2007) *J Mol Biol* 371:374-387) and can improve the stability of sequences fused to the foldon domain (Du, C. et al. (2008) *Appl Microbiol Biotechnol* 79:195-202.

In some embodiments, the C-terminus of an H-NOX domain is linked to the N-terminus of a foldon domain. In other embodiments, the N-terminus of an H-NOX domain is linked to the N-terminus of a foldon domain. In yet other embodiments, the C-terminus of an H-NOX domain is linked to the C-terminus of a foldon domain. In some embodiments, the N-terminus of an H-NOX domain is linked to the C-terminus of a foldon domain.

In some embodiments, linkers are be used to join a foldon domain to an H-NOX domain. In some embodiments, a linker comprising any one of one, two, three, four, five, six, seven, eight, nine, ten or more than ten amino acids may be placed between the polymerization domain and the H-NOX domain. Exemplary linkers include but are not limited to Gly-Ser-Gly and Arg-Gly-Ser linkers. In some embodiments, the invention provides a trimeric H-NOX protein comprising from N-terminus to C-terminus: a *T. tengcongensis* H-NOX domain, a Gly-Ser-Gly amino acid linker, and a foldon domain. In some embodiments, the invention provides a trimeric H-NOX protein comprising from N-terminus to C-terminus: a *T. tengcongensis* H-NOX domain, a Gly-Ser-Gly amino acid linker, a foldon domain, an Arg-Gly-Ser amino acid linker, and a His$_6$ tag. In some embodiments, the *T. tengcongensis* H-NOX domain comprises an L144F mutation. In some embodiments, the *T. tengcongensis* H-NOX domain comprises a W9F mutation and a L144F mutation. In some embodiments, the *T. tengcongensis* H-NOX domain is a wild-type H-NOX domain.

Monomeric H-NOX Domain Subunits

In one aspect, the invention provides recombinant monomeric H-NOX proteins (i.e. monomeric H-NOX subunits of polymeric H-NOX proteins) that can associate to form polymeric H-NOX proteins. In some embodiments, the invention provides recombinant H-NOX proteins comprising an H-NOX domain as described herein and a polymerization domain. The H-NOX domain and the polymerization domain may be covalently linked or noncovalently linked. In some embodiments, the C-terminus of an H-NOX domain of the recombinant monomeric H-NOX protein is linked to the N-terminus of a polymerization domain. In other embodiments, the N-terminus of an H-NOX domain of the recombinant monomeric H-NOX protein is linked to the N-terminus of a polymerization domain. In yet other embodiments, the C-terminus of an H-NOX domain of the recombinant monomeric H-NOX protein is linked to the C-terminus of a polymerization domain. In some embodiments, the N-terminus of an H-NOX domain of the recombinant monomeric H-NOX protein is linked to the C-terminus of a polymerization domain. In some embodiments, the recombinant monomeric H-NOX protein does not comprise a guanylyl cyclase domain.

In some embodiments, the monomeric H-NOX protein comprises a wild-type H-NOX domain. In some embodiments of the invention, the monomeric H-NOX protein comprises one of more mutations in the H-NOX domain. In some embodiments, the one or more mutations alter the $O_2$ dissociation constant, the $k_{off}$ for oxygen, the rate of heme autooxidation, the NO reactivity, the NO stability or any combination of two or more of the foregoing compared to that of the corresponding wild-type H-NOX domain. In some embodiments, the mutation is a distal pocket mutation. In some embodiments, the mutation comprises a mutation that is not in the distal pocket. In some embodiments, the distal pocket mutation corresponds to a L144 mutation of *T. tengcongensis* (e.g. a L144F mutation). In some embodiments, the recombinant monomeric H-NOX protein comprises two distal pocket mutations corresponding to a W9 and a L144 mutation of *T. tengcongensis* (e.g. a W9F/L144F mutation).

In some aspects, the invention provides recombinant monomeric H-NOX proteins that associate to form trimeric H-NOX proteins. In some embodiments, the recombinant H-NOX protein comprises an H-NOX domain and a trimerization domain. In some embodiments, the trimerization domain is a foldon domain as discussed herein. In some embodiments, the H-NOX domain is a *T. tengcongensis* H-NOX domain. In some embodiments the C-terminus of the *T. tengcongensis* H-NOX domain is covalently linked to the N-terminus of the foldon domain. In some embodiments the C-terminus of the *T. tengcongensis* H-NOX domain is covalently linked to the C-terminus of the foldon domain. In some embodiments, the *T. tengcongensis* domain is an L144F H-NOX domain. In some embodiments, the *T. tengcongensis* domain is a W9F/L144F H-NOX domain. In some embodiments, the *T. tengcongensis* domain is a wild-type H-NOX domain.

In some embodiments, the H-NOX domain is covalently linked to the polymerization domain using an amino acid linker sequence. In some embodiments, the amino acid linker sequence is one, two, three, four, five, six, seven, eight, nine, ten or more than ten amino acids in length. Exemplary amino acid linker sequences include but are not limited to a Gly-Ser-Gly sequence and an Arg-Gly-Ser sequence. In some embodiments, the polymeric H-NOX protein is a trimeric H-NOX protein comprising three H-NOX domains and three trimerization sequences wherein the H-NOX domain is covalently linked to the trimerization domain via an amino acid linker sequence. In some embodiments, the monomeric H-NOX protein comprises the following from the N-terminus to the C-terminus: an L144F *T. tengcongensis* H-NOX domain, a Gly-Ser-Gly amino acid linker sequence, and a foldon domain. In some embodiments, the monomeric H-NOX protein comprises the following from the N-terminus to the C-terminus: a W9F/L144F *T. tengcongensis* H-NOX domain, a Gly-Ser-Gly amino acid linker sequence, and a foldon domain. In some embodiments, the monomeric H-NOX protein comprises the following from the N-terminus to the C-terminus: a wild-type *T. tengcongensis* H-NOX domain, a Gly-Ser-Gly amino acid linker sequence, and a foldon domain.

In some embodiments, the recombinant monomeric H-NOX protein comprises a tag; e.g., a $His_6$, a FLAG® tag, a GST, or an MBP tag. In some embodiments, the recombinant monomeric H-NOX protein comprises a $His_6$ tag. In some embodiments, the recombinant monomeric H-NOX protein does not comprise a tag. In some embodiments, the tag (e.g. a $His_6$ tag) is covalently linked to the polymerization domain using an amino acid spacer sequence. In some embodiments, the amino acid linker sequence is one, two, three, four, five, six, seven, eight, nine, ten or more than ten amino acids in length. Exemplary amino acid linker sequences include but are not limited to a Gly-Ser-Gly sequence and an Arg-Gly-Ser sequence. In some embodiments, the polymeric H-NOX protein is a trimeric H-NOX protein comprising three H-NOX domains, three trimerization sequences, and three $His_6$ tags, wherein the H-NOX domain is covalently linked to the trimerization domain via an amino acid linker sequence and the trimerization domain is covalently linked to the $His_6$ tag via an amino acid linker sequence. In some embodiments, the monomeric H-NOX protein comprises the following from the N-terminus to the C-terminus: an L144F *T. tengcongensis* H-NOX domain, a Gly-Ser-Gly amino acid linker sequence, a Cordon domain, an Arg-Gly-Ser linker sequence, and a $His_6$ tag. In some embodiments, the monomeric H-NOX protein comprises the following from the N-terminus to the C-terminus: a W9F/L144F *T. tengcongensis* H-NOX domain, a Gly-Ser-Gly amino acid linker sequence, a foldon domain, an Arg-Gly-Ser linker sequence, and a $His_6$ tag. In some embodiments, the monomeric H-NOX protein comprises the following from the N-terminus to the C-terminus: a wild-type *T. tengcongensis* H-NOX domain, a Gly-Ser-Gly amino acid linker sequence, a foldon domain, an Arg-Gly-Ser linker sequence, and a $His_6$ tag.

In some embodiments the recombinant monomeric H-NOX protein comprises the amino acid sequence of SEQ ID NO:6 or SEQ ID NO:8.

Characteristics of Wild-Type and Mutant H-NOX Proteins

The present invention provides the use of $O_2$ carrier polypeptides for use in enhancing tumor immunogenicity; for example, by inhibiting the immune suppressive activities associated with tumor hypoxia. A non-limiting exemplary family of $O_2$ carrier polypeptides is the H-NOX family of $O_2$ carrier polypeptides. As described herein, a large number of diverse H-NOX mutant proteins, including polymeric H-NOX proteins, providing ranges of NO and $O_2$ dissociation constants, $O_2$ $k_{off}$, NO reactivity, and stability have been generated. To provide operative blood gas carriers, the H-NOX proteins may be used to functionally replace or supplement endogenous $O_2$ carriers, such as hemoglobin. In some embodiments, H-NOX proteins such as polymeric H-NOX proteins, are used to deliver $O_2$ to hypoxic tumor tissue (e.g. a glioblastoma) as an adjuvant to radiation therapy or chemotherapy. Accordingly, in some embodiments, an H-NOX protein has a similar or improved $O_2$ association rate, $O_2$ dissociation rate, dissociation constant for $O_2$ binding, NO stability, NO reactivity, autoxidation rate, plasma retention time, or any combination of two or more of the foregoing compared to an endogenous $O_2$ carrier, such as hemoglobin. In some embodiments, the H-NOX protein is a polymeric H-NOX protein. In some embodiments, the polymeric H-NOX protein is a trimeric H-NOX protein comprising three monomers, each monomer comprising a *T. tengcongensis* L144F H-NOX domain and a foldon domain. In some embodiments, the polymeric H-NOX protein is a trimeric H-NOX protein comprising three monomers, each monomer comprising a *T. tengcongensis* W9F/L144F H-NOX domain and a foldon domain. In some embodiments, the polymeric H-NOX protein is a trimeric H-NOX protein comprising three monomers, each monomer comprising a *T. tengcongensis* L144F H-NOX domain and a foldon domain.

In various embodiments, the $k_{off}$ for $O_2$ for an H-NOX protein, including a polymeric H-NOX protein, is between about 0.01 to about 200 $s^{-1}$ at 20° C., such as about 0.1 to about 200 $s^{-1}$, about 0.1 to 100 $s^{-1}$, about 1.0 to about 16.0 $s^{-1}$, about 1.35 to about 23.4 $s^{-1}$, about 1.34 to about 18 $s^{-1}$, about 1.35 to about 14.5 $s^{-1}$, about 0.21 to about 23.4 $s^{-1}$, about 1.35 to about 2.9 $s^{-1}$, about 2 to about 3 $s^{-1}$, about 5 to about 15 $s^{-1}$, or about 0.1 to about 1 $s^{-1}$. In some embodiments, the H-NOX protein has a $k_{off}$ for oxygen that is less than or equal to about 0.65 $s^{-1}$ at 20° C. (such as between about 0.21 $s^{-1}$ to about 0.65 $s^{-1}$ at 20° C.).

In various embodiments, the $k_{on}$ for $O_2$ for an H-NOX protein, including a polymeric H-NOX protein, is between about 0.14 to about 60 $\mu M^{-1}$ $s^{-1}$ at 20° C., such as about 6 to about 60 $\mu M^{-1}$ $s^{-1}$, about 6 to 12 $\mu M^{-1}$ $s^{-1}$, about 15 to about 60 $\mu M^{-1}$ $s^{-1}$, about 5 to about 18 $\mu M^{-1}$ $s^{-1}$, or about 6 to about 15 $\mu M^{-1}$ $s^{-1}$.

In various embodiments, the kinetic or calculated $K_D$ for $O_2$ binding by an H-NOX protein, including a polymeric H-NOX protein, is between about 1 nM to 1 mM, about 1 $\mu$M to about 10 $\mu$M, or about 10 $\mu$M to about 50 $\mu$M. In some embodiments the calculated $K_D$ for $O_2$ binding is any one of about 2 nM to about 2 $\mu$M, about 2 $\mu$M to about 1 mM, about 100 nM to about 1 $\mu$M, about 9 $\mu$M to about 50 $\mu$M, about 100 µM to about 1 mM, about 50 nM to about 10 µM, about 2 nM to about 50 µM, about 100 nM to about 1.9 µM, about 150 nM to about 1 µM, or about 100 nM to about 255 nM, about 20 nM to about 2 µM, 20 nM to about 75 nM, about 1 µM to about 2 µM, about 2 µM to about 10 µM, about 2 µM to about 9 µM, or about 100 nM to 500 nM at 20° C. In some embodiments, the kinetic or calculated $K_D$ for $O_2$ binding is less than about any of 100 nM, 80 nM, 50 nM, 30 nM, 25 nM, 20 nM, or 10 nM at 20° C.

In various embodiments, the kinetic or calculated $K_D$ for $O_2$ binding by an H-NOX protein, including a polymeric H-NOX protein, is within about 0.01 to about 100-fold of that of hemoglobin under the same conditions (such as at 20° C.), such as between about 0.1 to about 10-fold or between about 0.5 to about 2-fold of that of hemoglobin under the same conditions (such as at 20° C.). In various embodiments, the kinetic or calculated $K_D$ for NO binding by an H-NOX protein is within about 0.01 to about 100-fold of that of hemoglobin under the same conditions (such as at 20° C.), such as between about 0.1 to about 10-fold or between about 0.5 to about 2-fold of that of hemoglobin under the same conditions (such as at 20° C.).

In some embodiments, less than about any of 50, 40, 30, 10, or 5% of an H-NOX protein, including a polymeric H-NOX protein, is oxidized after incubation for about any of 1, 2, 4, 6, 8, 10, 15, or 20 hours at 20° C.

In various embodiments, the NO reactivity of an H-NOX protein, including a polymeric H-NOX protein, is less than about 700 s$^{-1}$ at 20° C., such as less than about 600 s$^{-1}$, 500 s$^{-1}$, 400 s$^{-1}$, 300 s$^{-1}$, 200 s$^{-1}$, 100 s$^{-1}$, 75 s$^{-1}$, 50 s$^{-1}$, 25 s$^{-1}$, 20 s$^{-1}$, 10 s$^{-1}$, 50 s$^{-1}$, 3 s$^{-1}$, 2 s$^{-1}$, 1.8 s$^{-1}$, 1.5 s$^{-1}$, 1.2 s$^{-1}$, 1.0 s$^{-1}$, 0.8 s$^{-1}$, 0.7 s$^{-1}$, or 0.6 s$^{-1}$ at 20° C. In various embodiments, the NO reactivity of an H-NOX protein is between about 0.1 to about 600 s$^{-1}$ at 20° C., such as between about 0.5 to about 400 s$^{-1}$, about 0.5 to about 100 s$^{-1}$, about 0.5 to about 50 s$^{-1}$, about 0.5 to about 10 s$^{-1}$, about 1 to about 5 s$^{-1}$, or about 0.5 to about 2.1 s$^{-1}$ at 20° C. In various embodiments, the reactivity of an H-NOX protein is at least about 10, 100, 1,000, or 10,000 fold lower than that of hemoglobin under the same conditions, such as at 20° C.

In various embodiments, the rate of heme autoxidation of an H-NOX protein, including a polymeric H-NOX protein, is less than about 1.0 h$^{-1}$ at 37° C., such as less than about any of 0.9 h$^{-1}$, 0.8 h$^{-1}$, 0.7 h$^{-1}$, 0.6 h$^{-1}$, 0.5 h$^{-1}$, 0.4 h$^{-1}$, 0.3 h$^{-1}$, 0.2 h$^{-1}$, 0.1 h$^{-1}$, or 0.05 h$^{-1}$ at 37C. In various embodiments, the rate of heme autoxidation of an H-NOX protein is between about 0.006 to about 5.0 h$^{-1}$ at 37° C., such as about 0.006 to about 1.0 h$^{-1}$, 0.006 to about 0.9 h$^{-1}$, or about 0.06 to about 0.5 h$^{-1}$ at 37° C.

In various embodiments, a mutant H-NOX protein, including a polymeric H-NOX protein, has (a) an $O_2$ or NO dissociation constant, association rate ($k_{on}$ for $O_2$ or NO), or dissociation rate ($k_{off}$ for $O_2$ or NO) within 2 orders of magnitude of that of hemoglobin, (b) has an NO affinity weaker (e.g., at least about 10-fold, 100-fold, or 1000-fold weaker) than that of sGC β1, respectively, (c) an NO reactivity with bound $O_2$ at least 1000-fold less than hemoglobin, (d) an in vivo plasma retention time at least 2, 10, 100, or 1000-fold higher than that of hemoglobin, or (e) any combination of two or more of the foregoing.

Exemplary suitable $O_2$ carriers provide dissociation constants within two orders of magnitude of that of hemoglobin, i.e. between about 0.01 and 100-fold, such as between about 0.1 and 10-fold, or between about 0.5 and 2-fold of that of hemoglobin. A variety of established techniques may be used to quantify dissociation constants, such as the techniques described herein (Boon, E. M. et al. (2005). *Nature Chem. Biol.* 1:53-59; Boon, E. M. et al. (October 2005). *Curr. Opin. Chem. Biol.* 9 (5): 441-446; Boon, E. M. et al. (2005). *J. Inorg. Biochem.* 99 (4): 892-902), Vandegriff, K. D. et al. (Aug. 15, 2004). *Biochem J.* 382 (Pt 1): 183-189, which are each hereby incorporated by reference in their entireties, particularly with respect to the measurement of dissociation constants), as well as those known to the skilled artisan. Exemplary $O_2$ carriers provide low or minimized NO reactivity of the H-NOX protein with bound $O_2$, such as an NO reactivity lower than that of hemoglobin. In some embodiments, the NO reactivity is much lower, such as at least about 10, 100, 1,000, or 10,000-fold lower than that of hemoglobin. A variety of established techniques may be used to quantify NO reactivity (Boon, E. M. et al. (2005). *Nature Chem. Biol.* 1:53-59; Boon, E. M. et al. (October 2005). *Curr. Opin. Chem. Biol.* 9 (5): 441-446; Boon, E. M. et al. (2005). *J. Inorg. Biochem.* 99 (4): 892-902), Vandegriff, K. D. et al. (Aug. 15, 2004). *Biochem J.* 382 (Pt 1): 183-189, which are each hereby incorporated by reference in their entireties, particularly with respect to the measurement of NO reactivity) as well as those known to the skilled artisan. Because wild-type *T. tengcongensis* H-NOX has such a low NO reactivity, other wild-type H-NOX proteins and mutant H-NOX proteins may have a similar low NO reactivity. For example, *T. tengcongensis* H-NOX Y140H has an NO reactivity similar to that of wild-type *T. tengcongensis* H-NOX.

In addition, suitable $O_2$ carriers provide high or maximized stability, particularly in vivo stability. A variety of stability metrics may be used, such as oxidative stability (e.g., stability to autoxidation or oxidation by NO), temperature stability, and in vivo stability. A variety of established techniques may be used to quantify stability, such as the techniques described herein (Boon, E. M. et al. (2005). *Nature Chem. Biol.* 1:53-59; Boon, E. M. et al. (October 2005). *Curr. Opin. Chem. Biol.* 9 (5): 441-446; Boon, E. M. et al. (2005). *J. Inorg. Biochem.* 99 (4): 892-902), as well as those known to the skilled artisan. For in vivo stability in plasma, blood, or tissue, exemplary metrics of stability include retention time, rate of clearance, and half-life. H-NOX proteins from thermophilic organisms are expected to be stable at high temperatures. In various embodiments, the plasma retention times are at least about 2-, 10-, 100-, or 1000-fold greater than that of hemoglobin (e.g. Bobofchak, K. M. et al. (August 2003). *Am. J. Physiol. Heart Circ. Physiol.* 285 (2): H549-H561). As will be appreciated by the skilled artisan, hemoglobin-based blood substitutes are limited by the rapid clearance of cell-free hemoglobin from plasma due the presence of receptors for hemoglobin that remove cell-free hemoglobin from plasma. Since there are no receptors for H-NOX proteins in plasma, wild-type and mutant H-NOX proteins are expected to have a longer plasma retention time than that of hemoglobin. If desired, the plasma retention time can be increased by PEGylating or crosslinking an H-NOX protein or fusing an H-NOX protein with another protein using standard methods (such as those described herein and those known to the skilled artisan).

In various embodiments, the H-NOX protein, including a polymeric H-NOX protein, has an $O_2$ dissociation constant between about 1 nM to about 1 mM at 20° C. and a NO reactivity at least about 10-fold lower than that of hemoglobin under the same conditions, such as at 20° C. In some embodiments, the H-NOX protein has an $O_2$ dissociation constant between about 1 nM to about 1 mM at 20° C. and a NO reactivity less than about 700 s$^{-1}$ at 20° C. (e.g., less than about 600 s$^{-1}$, 500 s$^{-1}$, 100 s$^{-1}$, 20 s$^{-1}$, or 1.8 s$^{-1}$ at 20°

C.). In some embodiments, the H-NOX protein has an $O_2$ dissociation constant within 2 orders of magnitude of that of hemoglobin and a NO reactivity at least about 10-fold lower than that of hemoglobin under the same conditions, such as at 20° C. In some embodiments, the H-NOX protein has a $k_{off}$ for oxygen between about 0.01 to about 200 $s^{-1}$ at 20° C. and an NO reactivity at least about 10-fold lower than that of hemoglobin under the same conditions, such as at 20° C. In some embodiments, the H-NOX protein has a $k_{off}$ for oxygen that is less than about 0.65 $s^{-1}$ at 20° C. (such as between about 0.21 $s^{-1}$ to about 0.64 $s^{-1}$ at 20° C.) and a NO reactivity at least about 10-fold lower than that of hemoglobin under the same conditions, such as at 20° C. In some embodiments of the invention, the $O_2$ dissociation constant of the H-NOX protein is between about 1 nM to about 1 µM (1000 nM), about 1 µM to about 10 µM, or about 10 µM to about 50 µM. In particular embodiments, the $O_2$ dissociation constant of the H-NOX protein is between about 2 nM to about 50 µM, about 50 nM to about 10 µM, about 100 nM to about 1.9 µM, about 150 nM to about 1 µM, or about 100 nM to about 255 nM at 20° C. In various embodiments, the $O_2$ dissociation constant of the H-NOX protein is less than about 80 nM at 20° C., such as between about 20 nM to about 75 nM at 20° C. In some embodiments, the NO reactivity of the H-NOX protein is at least about 100-fold lower or about 1,000 fold lower than that of hemoglobin, under the same conditions, such as at 20° C. In some embodiments, the NO reactivity of the H-NOX protein is less than about 700 $s^{-1}$ at 20° C., such as less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$, 2 $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$, or 0.6 $s^{-1}$ at 20° C. In some embodiments, the $k_{off}$ for oxygen of the H-NOX protein is between 0.01 to 200 $s^{-1}$ at 20° C., such as about 0.1 to about 200 $s^{-1}$, about 0.1 to 100 $s^{-1}$, about 1.35 to about 23.4 $s^{-1}$, about 1.34 to about 18 $s^{-1}$, about 1.35 to about 14.5 $s^{-1}$, about 0.21 to about 23.4 $s^{-1}$, about 2 to about 3 $s^{-1}$, about 5 to about 15 $s^{-1}$, or about 0.1 to about 1 $s^{-1}$. In some embodiments, the $O_2$ dissociation constant of the H-NOX protein is between about 100 nM to about 1.9 µM at 20° C., and the $k_{off}$ for oxygen of the H-NOX protein is between about 1.35 $s^{-1}$ to about 14.5 $s^{-1}$ at 20° C. In some embodiments, the rate of heme autoxidation of the H-NOX protein is less than about 1 $h^{-1}$ at 37° C., such as less than about any of 0.9 $h^{-1}$, 0.8 $h^{-1}$, 0.7 $h^{-1}$, 0.6 $h^{-1}$, 0.5 $h^{-1}$, 0.4 $h^{-1}$, 0.3 $h^{-1}$, 0.2 $h^{-1}$, or 0.1 $h^{-1}$. In some embodiments, the $k_{off}$ for oxygen of the H-NOX protein is between about 1.35 $s^{-1}$ to about 14.5 $s^{-1}$ at 20° C., and the rate of heme autoxidation of the H-NOX protein is less than about 1 $h^{-1}$ at 37° C. In some embodiments, the $k_{off}$ for oxygen of the H-NOX protein is between about 1.35 $s^{-1}$ to about 14.5 $s^{-1}$ at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the rate of heme autoxidation of the H-NOX protein is less than about 1 $h^{-1}$ at 37° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.).

In some embodiments, the viscosity of the H-NOX protein solution, including a polymeric H-NOX protein solution, is between 1 and 4 centipoise (cP). In some embodiments, the colloid oncotic pressure of the H-NOX protein solution is between 20 and 50 mm Hg.

Measurement of $O_2$ and/or NO Binding

One skilled in the art can readily determine the oxygen and nitric oxide binding characteristics of any H-NOX protein including a polymeric H-NOX protein such as a trimeric H-NOX protein by methods known in the art and by the non-limiting exemplary methods described below.

Kinetic $K_D$: Ratio of $k_{off}$ to $k_{on}$

The kinetic $K_D$ value is determined for wild-type and mutant H-NOX proteins, including polymeric H-NOS proteins, essentially as described by Boon, E. M. et al. (2005). Nature Chemical Biology 1:53-59, which is hereby incorporated by reference in its entirety, particularly with respect to the measurement of $O_2$ association rates, $O_2$ dissociation rates, dissociation constants for $O_2$ binding, autoxidation rates, and NO dissociation rates.

$k_{on}$ ($O_2$ Association Rate)

$O_2$ association to the heme is measured using flash photolysis at 20° C. It is not possible to flash off the $Fe^{II}$ $O_2$ complex as a result of the very fast geminate recombination kinetics; thus, the $Fe^{II}$ CO complex is subjected to flash photolysis with laser light at 560 nm (Hewlett-Packard, Palo Alto, CA), producing the 5-coordinate $Fe^{II}$ intermediate, to which the binding of molecular $O_2$ is followed at various wavelengths. Protein samples are made by anaerobic reduction with 10 mM dithionite, followed by desalting on a PD-10 column (Millipore, Inc., Billerica, MA). The samples are then diluted to 20 µM heme in 50 mM TEA, 50 mM NaCl, pH 7.5 buffer in a controlled-atmosphere quartz cuvette, with a size of 100 µL to 1 mL and a path-length of 1-cm. CO gas is flowed over the headspace of this cuvette for 10 minutes to form the $Fe^{II}$-CO complex, the formation of which is verified by UV-visible spectroscopy (Soret maximum 423 nm). This sample is then either used to measure CO-rebinding kinetics after flash photolysis while still under 1 atmosphere of CO gas, or it is opened and stirred in air for 30 minutes to fully oxygenate the buffer before flash photolysis to watch $O_2$-rebinding events. $O_2$ association to the heme is monitored at multiple wavelengths versus time. These traces are fit with a single exponential using Igor Pro software (Wavemetrics, Inc., Oswego, OR; latest 2005 version). This rate is independent of observation wavelength but dependent on $O_2$ concentration. UV-visible spectroscopy is used throughout to confirm all the complexes and intermediates (Cary 3K, Varian, Inc. Palo Alto, CA). Transient absorption data are collected using instruments described in Dmochowski, I. J. et al. (Aug. 31, 2000). J Inorg Biochem. 81 (3): 221-228, which is hereby incorporated by reference in its entirety, particularly with respect to instrumentation. The instrument has a response time of 20 ns, and the data are digitized at 200 megasamples $s^{-1}$.

$k_{off}$ ($O_2$ Dissociation Rate)

To measure the $k_{off}$, $Fe^{II}$-$O_2$ complexes of protein (5 µM heme), are diluted in anaerobic 50 mM TEA, 50 mM NaCl, pH 7.5 buffer, and are rapidly mixed with an equal volume of the same buffer (anaerobic) containing various concentrations of dithionite and/or saturating CO gas. Data are acquired on a HI-TECH Scientific SF-61 stopped-flow spectrophotometer equipped with a Neslab RTE-100 constant-temperature bath set to 20° C. (TGK Scientific LTD., Bradford On Avon, United Kingdom). The dissociation of $O_2$ from the heme is monitored as an increase in the absorbance at 437 nm, a maximum in the $Fe^{II}$-$Fe^{II}$-$O_2$ difference spectrum, or 425 nm, a maximum in the $Fe^{II}$-$Fe^{II}$-CO difference spectrum. The final traces are fit to a single exponential using the software that is part of the instrument. Each experiment is done a minimum of six times, and the resulting rates are averaged. The dissociation rates measured are independent of dithionite concentration and independent of saturating CO as a trap for the reduced species, both with and without 10 mM dithionite present.

Kinetic $K_D$

The kinetic $K_D$ is determined by calculating the ratio of $k_{off}$ to $k_{on}$ using the measurements of $k_{off}$ and $k_{on}$ described above.

Calculated $K_D$

To measure the calculated $K_D$, the values for the $k_{off}$ and kinetic $K_D$ that are obtained as described above are graphed. A linear relationship between $k_{off}$ and kinetic $K_D$ is defined by the equation (y=mx+b). $k_{off}$ values were then interpolated along the line to derive the calculated $K_D$ using Excel: MAC 2004 (Microsoft, Redmond, WA). In the absence of a measured $k_{on}$, this interpolation provides a way to relate $k_{off}$ to $K_D$.

Rate of Autoxidation

To measure the rate of autoxidation, the protein samples are anaerobically reduced, then diluted to 5 μM heme in aerobic 50 mM TEA, 50 mM NaCl, pH 7.5 buffer. These samples are then incubated in a Cary 3E spectrophotometer equipped with a Neslab RTE-100 constant-temperature bath set to 37° C. and scanned periodically (Cary 3E, Varian, Inc., Palo Alto, CA). The rate of autoxidation is determined from the difference between the maximum and minimum in the $Fe^{III}$-$Fe^{II}$ difference spectrum plotted versus time and fit with a single exponential using Excel: MAC 2004 (Microsoft, Redmond, WA).

Rate of Reaction with NO

NO reactivity is measured using purified proteins (H-NOX, polymeric H-NOX, *Homo sapiens* hemoglobin (Hs Hb) etc.) prepared at 2 μM in buffer A and NO prepared at 200 μM in Buffer A (Buffer A: 50 mM Hepes, pH 7.5, 50 mM NaCl). Data are acquired on a HI-TECH Scientific SF-61 stopped-flow spectrophotometer equipped with a Neslab RTE-100 constant-temperature bath set to 20° C. (TGK Scientific LTD., Bradford On Avon, United Kingdom). The protein is rapidly mixed with NO in a 1:1 ratio with an integration time of 0.00125 sec. The wavelengths of maximum change are fit to a single exponential using the software that is part of the spectrometer, essentially measuring the rate-limiting step of oxidation by NO. The end products of the reaction are ferric-NO for the HNOX proteins and ferric-aquo for Hs Hb.

p50 Measurements

If desired, the p50 value for mutant or wild-type H-NOX proteins can be measured as described by Guarnone, R. et al. (September/October 1995). *Haematologica* 80 (5): 426-430, which is hereby incorporated by reference in its entirety, particularly with respect to the measurement of p50 values. The p50 value is determined using a HemOx analyzer. The measurement chamber starts at 0% oxygen and slowly is raised, incrementally, towards 100% oxygen. An oxygen probe in the chamber measures the oxygen saturation %. A second probe (UV-Vis light) measures two wavelengths of absorption, tuned to the alpha and beta peaks of the hemoprotein's (e.g., a protein such as H-NOX complexed with heme) UV-Vis spectra. These absorption peaks increase linearly as hemoprotein binds oxygen. The percent change from unbound to 100% bound is then plotted against the % oxygen values to generate a curve. The p50 is the point on the curve where 50% of the hemoprotein is bound to oxygen.

Specifically, the Hemox-Analyzer (TCS Scientific Corporation, New Hope, PA) determines the oxyhemoprotein dissociation curve (ODC) by exposing 50 μL of blood or hemoprotein to an increasing partial pressure of oxygen and deoxygenating it with nitrogen gas. A Clark oxygen electrode detects the change in oxygen tension, which is recorded on the x-axis of an x-y recorder. The resulting increase in oxyhemoprotein fraction is simultaneously monitored by dual-wavelength spectrophotometry at 560 nm and 576 nm and displayed on the y-axis. Blood samples are taken from the antemedial vein, anticoagulated with heparin, and kept at 4° C. on wet ice until the assay. Fifty μL of whole blood are diluted in 5 μL of Hemox-solution, a manufacturer-provided buffer that keeps the pH of the solution at a value of 7.4±0.01. The sample-buffer is drawn into a cuvette that is part of the Hemox-Analyzer and the temperature of the mixture is equilibrated and brought to 37° C.; the sample is then oxygenated to 100% with air. After adjustment of the $pO_2$ value the sample is deoxygenated with nitrogen; during the deoxygenation process the curve is recorded on graph paper. The P50 value is extrapolated on the x-axis as the point at which $O_2$ saturation is 50% using the software that is part of the Hemox-Analyzer. The time required for a complete recording is approximately 30 minutes.

H-NOX Nucleic Acids

The invention also features nucleic acids encoding any of the mutant H-NOX proteins, polymeric H-NOX, or recombinant monomer H-NOX protein subunits as described herein.

In particular embodiments, the nucleic acid includes a segment of or the entire nucleic acid sequence of any of nucleic acids encoding an H-NOX protein or an H-NOX domain. In some embodiments, the nucleic acid includes at least about 50, 100, 150, 200, 300, 400, 500, 600, 700, 800, or more contiguous nucleotides from a H-NOX nucleic acid and contains one or more mutations (e.g., 1, 2, 3, 4, 5, 6, 7, 8, 9, or 10 mutations) compared to the H-NOX nucleic acid from which it was derived. In various embodiments, a mutant H-NOX nucleic acid contains less than about 20, 15, 12, 10, 9, 8, 7, 6, 5, 4, 3, or 2 mutations compared to the H-NOX nucleic acid from which it was derived. The invention also features degenerate variants of any nucleic acid encoding a mutant H-NOX protein.

In some embodiments, the nucleic acid includes nucleic acids encoding two or more H-NOX domains. In some embodiments, the nucleic acids including two or more H-NOX domains are linked such that a polymeric H-NOX protein is expressed from the nucleic acid. In further embodiments, the nucleic acid includes nucleic acids encoding one or more polymerization domains. In some embodiments, the nucleic acids including the two or more H-NOX domains and the one or more polymerization domains are linked such that a polymeric H-NOX protein is expressed from the nucleic acid.

In some embodiments, the nucleic acid includes a segment or the entire nucleic acid sequence of any nucleic acid encoding a polymerization domain. In some embodiments the nucleic acid comprises a nucleic acid encoding an H-NOX domain and a polymerization domain. In some embodiments, the nucleic acid encoding an H-NOX domain and the nucleic acid encoding a polymerization domain a linked such that the produced polypeptide is a fusion protein comprising an H-NOX domain and a polymerization domain.

In some embodiments, the nucleic acid comprises nucleic acid encoding one or more $His_6$ tags. In some embodiments the nucleic acid further comprised nucleic acids encoding linker sequences positioned between nucleic acids encoding the H-NOX domain, the polymerization domain and/or a $His_6$ tag.

In some embodiments, the invention provides a nucleic acid encoding an H-NOX domain and a foldon domain. In some embodiments, the H-NOX domain is a *T. thermoanaerobacter* H-NOX domain. In some embodiments, the H-NOX domain is a wild-type *T. thermoanaerobacter*

H-NOX domain. In some embodiments, the H-NOX domain is a *T. thermoanaerobacter* L144F H-NOX domain. In some embodiments, the H-NOX domain is a *T. thermoanaerobacter* W9F/L144F H-NOX domain.

In some embodiments, the invention provides nucleic acids encoding the following 5' to 3': a L144F *T. tengcongensis* H-NOX domain, a Gly-Ser-Gly amino acid linker sequence, and a foldon domain. In some embodiments, the invention provides nucleic acids encoding the following 5' to 3': a W9F/L144F *T. tengcongensis* H-NOX domain, a Gly-Ser-Gly amino acid linker sequence, and a foldon domain. In some embodiments, the invention provides nucleic acids encoding the following 5' to 3': a wild-type *T. tengcongensis* H-NOX domain, a Gly-Ser-Gly amino acid linker sequence, and a foldon domain.

In some embodiments, the invention provides nucleic acids encoding the following 5' to 3': a L144F *T. tengcongensis* H-NOX domain, a Gly-Ser-Gly amino acid linker sequence, a foldon domain, an Arg-Gly-Ser linker sequence, and a $His_6$ tag. In some embodiments, the invention provides nucleic acids encoding the following 5' to 3': a W9F/L144F *T. tengcongensis* H-NOX domain, a Gly-Ser-Gly amino acid linker sequence, a foldon domain, an Arg-Gly-Ser linker sequence, and a $His_6$ tag. In some embodiments, the invention provides nucleic acids encoding the following 5' to 3': a wild-type *T. tengcongensis* H-NOX domain, a Gly-Ser-Gly amino acid linker sequence, a foldon domain, an Arg-Gly-Ser linker sequence, and a $His_6$ tag.

In some embodiments, the nucleic acid comprises the nucleic acid sequence set forth in SEQ ID NO:5 or SEQ ID NO:7.

The invention also includes a cell or population of cells containing at least one nucleic acid encoding a mutant H-NOX protein described herein. Exemplary cells include insect, plant, yeast, bacterial, and mammalian cells. These cells are useful for the production of mutant H-NOX proteins using standard methods, such as those described herein.

In some embodiments, the invention provides a cell comprising a nucleic acid encoding an H-NOX domain and a foldon domain. In some embodiments, the H-NOX domain is a *T. thermoanaerobacter* H-NOX domain. In some embodiments, the H-NOX domain is a wild-type *T. thermoanaerobacter* H-NOX domain. In some embodiments, the H-NOX domain is a *T. thermoanaerobacter* L144F H-NOX domain. In some embodiments, the H-NOX domain is a *T. thermoanaerobacter* W9F/L144F H-NOX domain. In some embodiments, the invention provides a cell comprising a nucleic acid comprising the nucleic acid sequence set forth in SEQ ID NO: 5 or SEQ ID NO:7.

Formulations of H-NOX Proteins

The present invention provides formulations of $O_2$ carrier polypeptides for use in enhancing tumor immunogenicity; for example, by inhibiting the immune suppressive activities associated with tumor hypoxia. A non-limiting exemplary family of $O_2$ carrier polypeptides is the H-NOX family of $O_2$ carrier polypeptides. Any wild-type or mutant H-NOX protein, including polymeric H-NOX proteins, described herein may be used for the formulation of pharmaceutical or non-pharmaceutical compositions. In some embodiments, the formulations comprise a monomeric H-NOX protein comprising an H-NOX domain and a polymerization domain such that the monomeric H-NOX proteins associate in vitro or in vivo to produce a polymeric H-NOX protein. As discussed further below, these formulations are useful in a variety of therapeutic and industrial applications.

In some embodiments, the pharmaceutical composition includes one or more wild-type or mutant H-NOX proteins described herein including polymeric H-NOX proteins and a pharmaceutically acceptable carrier or excipient. Examples of pharmaceutically acceptable carriers or excipients include, but are not limited to, any of the standard pharmaceutical carriers or excipients such as phosphate buffered saline solutions, water, emulsions such as oil/water emulsion, and various types of wetting agents. Exemplary diluents for aerosol or parenteral administration are phosphate buffered saline or normal (0.9%) saline. Compositions comprising such carriers are formulated by well-known conventional methods (see, for example, *Remington's Pharmaceutical Sciences*, 18th edition, A. Gennaro, ed., Mack Publishing Co., Easton, PA, 1990; and *Remington, The Science and Practice of Pharmacy* 20th Ed. Mack Publishing, 2000, which are each hereby incorporated by reference in their entireties, particularly with respect to formulations). In some embodiments, the formulations are sterile. In some embodiments, the formulations are essentially free of endotoxin.

While any suitable carrier known to those of ordinary skill in the art may be employed in the pharmaceutical compositions of this invention, the type of carrier will vary depending on the mode of administration. Compositions can be formulated for any appropriate manner of administration, including, for example, intravenous, intra-arterial, intravesicular, intratumoral, inhalation, intraperitoneal, intrapulmonary, intramuscular, subcutaneous, intra-tracheal, transmucosal, intraocular, intrathecal, or transdermal administration. For parenteral administration, such as subcutaneous injection, the carrier may include, e.g., water, saline, alcohol, a fat, a wax, or a buffer. For oral administration, any of the above carriers or a solid carrier, such as mannitol, lactose, starch, magnesium stearate, sodium saccharine, talcum, cellulose, glucose, sucrose, or magnesium carbonate, may be employed. Biodegradable microspheres (e.g., polylactate polyglycolate) may also be used as carriers.

In some embodiments, the pharmaceutical or non-pharmaceutical compositions include a buffer (e.g., neutral buffered saline, phosphate buffered saline, etc), a carbohydrate (e.g., glucose, mannose, sucrose, dextran, etc.), an antioxidant, a chelating agent (e.g., EDTA, glutathione, etc.), a preservative, another compound useful for binding and/or transporting oxygen, an inactive ingredient (e.g., a stabilizer, filler, etc.), or combinations of two or more of the foregoing. In some embodiments, the composition is formulated as a lyophilizate. H-NOX proteins may also be encapsulated within liposomes or nanoparticles using well known technology. Other exemplary formulations that can be used for H-NOX proteins are described by, e.g., U.S. Pat. Nos. 6,974,795, and 6,432,918, which are each hereby incorporated by reference in their entireties, particularly with respect to formulations of proteins.

The compositions described herein may be administered as part of a sustained release formulation (e.g., a formulation such as a capsule or sponge that produces a slow release of compound following administration). Such formulations may generally be prepared using well known technology and administered by, for example, oral, rectal or subcutaneous implantation, or by implantation at the desired target site. Sustained-release formulations may contain an H-NOX protein dispersed in a carrier matrix and/or contained within a reservoir surrounded by a rate controlling membrane. Carriers for use within such formulations are biocompatible, and may also be biodegradable. In some embodiments, the formulation provides a relatively constant level of H-NOX protein release. The amount of H-NOX protein contained within a sustained release formulation depends upon the site of implantation, the rate and expected duration of release, and the nature of the condition to be treated or prevented.

In some embodiments, the pharmaceutical composition contains an effective amount of a wild-type or mutant H-NOX protein. In some embodiments, the pharmaceutical composition contains an effective amount of a polymeric H-NOX protein comprising two or more wild-type or mutant H-NOX domains. In some embodiments, the pharmaceutical composition contains an effective amount of a recombinant monomeric H-NOX protein comprising a wild-type or mutant H-NOX domain and a polymerization domain as described herein. In some embodiments, the formulation comprises a trimeric H-NOX protein comprising three monomers, each monomer comprising a *T. tengcongensis* L144F H-NOX domain and a foldon domain. In some embodiments, the formulation comprises a trimeric H-NOX protein comprising three monomers, each monomer comprising a *T. tengcongensis* W9F/L144F H-NOX domain and a foldon domain. In some embodiments, the formulation comprises a trimeric H-NOX protein comprising three monomers, each monomer comprising a *T. tengcongensis* L144F H-NOX domain and a foldon domain. In some embodiments, the cells. In some embodiments, the modulating of tumor immunity comprises increasing antigen processing. In some embodiments, the modulating of tumor immunity comprises increasing the presentation capabilities of dendritic cells (DC). In some embodiments, the modulating of tumor immunity comprises one or more of increasing lymphocyte infiltration to the tumor, increasing antigen processing, or increasing DC presentation capability. In some embodiments, the modulating of tumor immunity comprises lymphocyte activation. In some embodiments, the modulating of tumor immunity comprises cytokine secretion. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments of the invention, the increase in lymphocyte infiltration to the tumor is accompanied by inhibition of one or more of Treg cells, tumor associated macrophages or myeloid derived suppressor cells in the tumor. In some embodiments, the increase in lymphocyte infiltration to the tumor is accompanied by an increase in MHC1 expression on the tumor cells.

In some embodiments, the invention provides methods for decreasing expression of HIF-1α in a tumor in an individual comprising administering to the individual an effective amount of an $O_2$ carrier polypeptide (e.g. an H-NOX protein). In some embodiments, administration of an effective amount of an $O_2$ carrier polypeptide (e.g., an H-NOX protein) to an individual results in a decrease in expression of HIF-1α. In some embodiments, the expression of HIF-1α is decreased by more than about any of 10%, 20%, 30%, 40%, 50%, 60%, 70%, 80%, 90% or 100% compared to expression of HIF-1α in the absence of treatment with an $O_2$ carrier polypeptide. In some embodiments, the expression of HIF-1α is reduced compared to expression of HIF-1α in the absence of treatment with an $O_2$ carrier protein for more than about any of 1 hr, 2 hr, 3 hr, 4 hr, 5 hr, 6 hr, 8 hr, 10 hr, 12 hr, 16 hr, 20 hr, 24 hr, 30 hr, 36, hr 42 hr or 48 hr. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments, the invention provides methods for decreasing expression of HIF-1α in a tumor in an individual comprising administering to the individual an effective amount of an $O_2$ carrier polypeptide (e.g. an H-NOX protein) wherein the decrease in expression of HIF-1α is measured as a decrease in expression of vascular epithelial cell growth factor (VEGF). In some embodiments, administration of an effective amount of an $O_2$ carrier polypeptide (e.g., an H-NOX protein) to an individual results in a decrease in expression of VEGF. In some embodiments, the expression of VEGF is decreased by more than about any of 10%, 20%, 30%, 40%, 50%, 60%, 70%, 80%, 90% or 100% compared to expression of VEGF in the absence of treatment with an $O_2$ carrier polypeptide. In some embodiments, the expression of VEGF is reduced compared to expression of VEGF in the absence of treatment with an $O_2$ carrier protein for more than about any of 1 hr, 2 hr, 3 hr, 4 hr, 5 hr, 6 hr, 8 hr, 10 hr, 12 hr, 16 hr, 20 hr, 24 hr, 30 hr, 36, hr 42 hr or 48 hr. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments, the invention provides methods for decreasing expression of HIF-1α in a tumor in an individual comprising administering to the individual an effective amount of an $O_2$ carrier polypeptide (e.g. an H-NOX protein) herein the decrease in expression of HIF-1α is measured as a decrease in expression of glucose transporter type 1 (Glut1). In some embodiments, administration of an effective amount of an $O_2$ carrier polypeptide (e.g., an H-NOX protein) to an individual results in a decrease in expression of Glut1. In some embodiments, the expression of Glut1 is decreased by more than about any of 10%, 20%, 30%, 40%, 50%, 60%, 70%, 80%, 90% or 100% compared to expression of Glut1 in the absence of treatment with an $O_2$ carrier polypeptide. In some embodiments, the expression of Glut1 is reduced compared to expression of Glut1 in the absence of treatment with an $O_2$ carrier protein for more than about any of 1 hr, 2 hr, 3 hr, 4 hr, 5 hr, 6 hr, 8 hr, 10 hr, 12 hr, 16 hr, 20 hr, 24 hr, 30 hr, 36, hr 42 hr or 48 hr. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments, the invention provides methods for decreasing expression of PD-L1 in a tumor in an individual comprising administering to the individual an effective amount of an $O_2$ carrier polypeptide (e.g. an H-NOX protein). In some embodiments, administration of an effective amount of an $O_2$ carrier polypeptide (e.g., an H-NOX protein) to an individual results in a decrease in expression of PD-L1. In some embodiments, the expression of PD-L1 is decreased by more than about any of 10%, 20%, 30%, 40%, 50%, 60%, 70%, 80%, 90% or 100% compared to expression of PD-L1 in the absence of treatment with an $O_2$ carrier polypeptide. In some embodiments, administration of an effective amount of an $O_2$ carrier polypeptide (e.g., an H-NOX protein) to an individual results in a decrease in the interaction of PD-L1 with PD-1. In some embodiments, the interaction of PD-L1 with PD1 is decreased by more than about any of 10%, 20%, 30%, 40%, 50%, 60%, 70%, 80%, 90% or 100% compared to interaction of PD-L1 with PD1 in the absence of treatment with an $O_2$ carrier polypeptide. In some embodiments, the expression of PD-L1 is reduced compared to expression of PD-L1 in the absence of treatment with an $O_2$ carrier protein for more than about any of 1 hr, 2 hr, 3 hr, 4 hr, 5 hr, 6 hr, 8 hr, 10 hr, 12 hr, 16 hr, 20 hr, 24 hr, 30 hr, 36, hr 42 hr or 48 hr. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments, the invention provides methods for decreasing expression of A2AR in a tumor in an individual comprising administering to the individual an effective amount of an $O_2$ carrier polypeptide (e.g. an H-NOX protein). In some embodiments, administration of an effective amount of an $O_2$ carrier polypeptide (e.g., an H-NOX protein) to an individual results in a decrease in expression of A2AR. In some embodiments, the expression of A2AR is decreased by more than about any of 10%, 20%, 30%, 40%, 50%, 60%, 70%, 80%, 90% or 100% compared to expression of A2AR in the absence of treatment with an $O_2$ carrier polypeptide. In some embodiments, administration of an effective amount of an $O_2$ carrier polypeptide (e.g., an H-NOX protein) to an individual results in a decrease in the interaction of A2AR with adenosine. In some embodiments, the interaction of A2AR with adenosine is decreased by more than about any of 10%, 20%, 30%, 40%, 50%, 60%, 70%, 80%, 90% or 100% compared to interaction of A2AR with adenosine in the absence of treatment with an $O_2$ carrier polypeptide. In some embodiments, the expression of A2AR is reduced compared to expression of A2AR in the absence of treatment with an $O_2$ carrier protein for more than about any of 1 hr, 2 hr, 3 hr, 4 hr, 5 hr, 6 hr, 8 hr, 10 hr, 12 hr, 16 hr, 20 hr, 24 hr, 30 hr, 36, hr 42 hr or 48 hr. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments, the invention provides methods for decreasing expression of HIF-2α in a tumor in an individual comprising administering to the individual an effective amount of an $O_2$ carrier polypeptide (e.g. an H-NOX protein). In some embodiments, administration of an effective amount of an $O_2$ carrier polypeptide (e.g., an H-NOX protein) to an individual results in a decrease in expression of HIF-2α. In some embodiments, the expression of HIF-2α is decreased by more than about any of 10%, 20%, 30%, 40%, 50%, 60%, 70%, 80%, 90% or 100% compared to expression of HIF-2α in the absence of treatment with an $O_2$ carrier polypeptide. In some embodiments, administration of an effective amount of an $O_2$ carrier polypeptide (e.g., an H-NOX protein) to an individual results in a decrease in the expression of HIF-2α. In some embodiments, the expression of HIF-2α is decreased by more than about any of 10%, 20%, 30%, 40%, 50%, 60%, 70%, 80%, 90% or 100% compared to expressoin of HIF-2α in the absence of treatment with an $O_2$ carrier polypeptide. In some embodiments, the expression of HIF-2α is reduced compared to expression of HIF-2α in the absence of treatment with an $O_2$ carrier protein for more than about any of 1 hr, 2 hr, 3 hr, 4 hr, 5 hr, 6 hr, 8 hr, 10 hr, 12 hr, 16 hr, 20 hr, 24 hr, 30 hr, 36, hr 42 hr or 48 hr. In some embodiments, the $O_2$ carrier polypeptide is a trimeric Tt H-NOX L144F polypeptide. In some embodiments, the $O_2$ carrier polypeptide is a PEGylated trimeric Tt H-NOX L144F polypeptide.

In some embodiments, the invention provides methods for modulating tumor immunity (e.g., enhancing an immune response to a tumor) in an individual by any of the methods described herein. Examples of tumors include but are not limited to a brain tumor, a glioblastoma, a bone tumor, a pancreatic tumor, a skin tumor, a tumor of the head or neck, a melanoma, a lung tumor, a uterine tumor, an ovarian tumor, a colorectal tumor, an anal tumor, a liver tumor, a hepatocellular carcinoma, a stomach tumor, a testicular tumor, an endometrial tumor, a cervical tumor, a vaginal tumor, a Hodgkin's lymphoma, a non-Hodgkin's lymphoma, an esophageal tumor, an intestinal tumor, a thyroid tumor, an adrenal tumor, a bladder tumor, a kidney tumor, a breast tumor, a multiple myeloma tumor, a sarcoma, or a squamous cell tumor.

In some embodiments, the invention provides methods for modulating tumor immunity (e.g., enhancing an immune response to a tumor) in an individual by any of the methods described herein thereby providing methods for treating cancer in an individual. Examples of cancers that may be treated by the methods of the invention include but are not limited to brain cancer, glioblastoma, bone cancer, pancreatic cancer, skin cancer, cancer of the head or neck, melanoma, lung cancer, uterine cancer, ovarian cancer, colorectal cancer, anal cancer, liver cancer, hepatocellular carcinoma, stomach cancer, testicular cancer, endometrial cancer, cervical cancer, Hodgkin's Disease, non-Hodgkin's lymphoma, esophageal cancer, intestinal cancer, thyroid cancer, adrenal cancer, bladder cancer, kidney cancer, breast cancer, multiple myeloma, sarcoma, or squamous cell cancer.

In some embodiments, the invention provides methods for modulating tumor immunity in an individual by any of the methods described herein. In some embodiments, the individual is a mammal; for example a human. In some embodiments, the mammal is a pet, a laboratory research animal, or a farm animal. Non-limiting examples of pets, research animals or farm animals include dogs, cats, horses, monkeys, rabbits, rats, mice, guinea pigs, hamsters, pigs and cows.

$O_2$ carrier polypeptides may be administered by any route including but not limited to intravenous, intra-arterial, intratumoral, intravesicular, inhalation, intraperitoneal, intrapulmonary, intramuscular, subcutaneous, intra-tracheal, transmucosal, intraocular, intrathecal, or transdermal administration.

In some aspects, sustained delivery of oxygen to a tumor is desired to inhibit hypoxia-mediated tumor immunity and to enhance an immune response to the tumor. In some embodiments of the invention, administration of the $O_2$ carrier polypeptide (e.g., H-NOX protein) is repeated. Administration of the $O_2$ carrier polypeptide may be repeated until a robust immune response to the tumor is established. In some embodiments, administration of the $O_2$ carrier polypeptide is repeated at least about any one of two times, three times, four times, five times, six times, seven times, eight times, nine times, ten times, twelve times, fourteen times, twenty times, thirty times, forty times, fifty times or one hundred times. In some embodiments, administration of the $O_2$ carrier polypeptide is repeated between about two times and about twenty times. In some embodiments, administration of the $O_2$ carrier polypeptide is repeated between any one of about twenty times and about forty times, any one of about forty times and about sixty times, any one of about sixty times and about eighty times, any one of about eighty times and about one hundred times, or any number of times therebetween. In some embodiments, administration of the $O_2$ carrier polypeptide is repeated daily or twice a day for about 42 to about 84 administrations.

Exemplary dosing frequencies include, but are not limited to, at least 1, 2, 3, 4, 5, 6, or 7 times (i.e., daily) a week. In some embodiments, the $O_2$ carrier polypeptide (e.g., H-NOX protein) is administered at least 2, 3, 4, or 6 times a day. In some embodiments, the $O_2$ carrier polypeptide is administered every four, every 8, every 12, every 24 hours, every 48 hours or two times a week or three times a week. In some embodiments, the $O_2$ carrier polypeptide is administered any one of between one hour and two hours, between two hours and four hours, between four hours and eight hours, between eight hours and twelve hours, or between twelve hours and 24 hours. In some embodiments, the $O_2$ carrier polypeptide is administered every four, every 8, every 12 or every 24 hours for a period of about one to about 10 days. In some embodiments, the $O_2$ carrier polypeptide can be administered, e.g., over a period of a few days or weeks. In some embodiments, the $O_2$ carrier polypeptide is administrated for a longer period, such as a few months or years. The dosing frequency of the composition may be adjusted over the course of the treatment based on the judgment of the administering physician.

In some embodiments, the $O_2$ carrier polypeptide (e.g., H-NOX protein) is administered as a bolus. In some embodiments, the volume of the bolus is greater than about any of 1 mL, 2 mL, 3 mL, 4 mL, 5 mL, 6 mL, 7 mL, 8 mL, 9 mL, 10 mL, 15 mL, 20 mL, 25 mL, 50 mL, 75 mL, or 100 mL. In some embodiments, administration of the bolus dose is repeated as above.

In some embodiments, the $O_2$ carrier polypeptide (e.g., H-NOX protein) is administered by infusion. In some embodiments, the infusions is for greater than about any of 15 minutes, 30 minutes, 1 hour, 2 hours, 3 hours, 4 hours, 5 hours, 6 hours, 7 hours, 8 hours, 9 hours, 10 hours, 12 hours, 16 hours, 20 hours or 24 hours. In some embodiments, the infusions is for between about any of 15 minutes and 30 minutes, 30 minutes and 1 hour, 1 hour and 2 hours, 2 hours and 3 hours, 3 hours and 4 hours, 4 hours and 5 hours, 5 hours and 6 hours, 6 hours and 7 hours, 7 hours and 8 hours, 8 hours and 9 hours, 9 hours and 10 hours, 10 hours and 12 hours, 12 hours and 16 hours, 16 hours and 20 hours or 20 hours and 24 hours. In some embodiments, the infusion rate is greater any of about 1 mL/hr, 2 mL/hr, 3 mL/hr, 4 mL/hr, 5 mL/hr, 6 mL/hr, 7 mL/hr, 8 mL/hr, 9 mL/hr, 10 mL/hr, 20 mL/hr, 30 mL/hr, 40 mL/hr, 50 mL/hr, 60 mL/hr, 70 mL/hr, 80 mL/hr, 90 mL/hr, 100 mL/hr, 200 mL/hr, 300 mL/hr, 400 mL/hr, 500 mL/hr, 600 mL/hr, 700 mL/hr, 800 mL/hr, 900 mL/hr, 1000 mL/hr, 2000 mL/hr, 3000 mL/hr, 4000 mL/hr, 5000 mL/hr, 6000 mL/hr, 7000 mL/hr, 8000 mL/hr, 9000 mL/hr, 10,000 mL/hr or any rate therebetween. In some embodiments, the infusion is repeated as above.

In some embodiments, the $O_2$ carrier polypeptide (e.g., H-NOX protein) is administered at a dose of greater than about any of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, or any dose therebetween. In some embodiments, the dose is provided as one or more bolus administrations. In some embodiments, the dose is provided as one or more infusions. In some embodiments the dose is provided in more than one administration (e.g., a dose of 100 mg/kg may be provided by two doses of 50 mg/kg).

In some embodiments of the invention, the $O_2$ carrier polypeptide (e.g. an H-NOX protein) is used in combination with radiation therapy. In some embodiments, the $O_2$ carrier polypeptide is administered to the individual any of at least 1, 2, 3, 4, 5, 6, 8, 10, 12, 14, 16, 18, 20, 22, or 24 hours before administration of the radiation. In some embodiments, the radiation is X irradiation. In some embodiments, the dose of X irradiation is any of about 0.5 Gy to about 75 Gy. In some embodiments, the cycle of $O_2$ carrier polypeptide administration and radiation administration is repeated any one of one, two, three, four, five or six times. In some embodiments, the cycle of $O_2$ carrier polypeptide administration and radiation administration is repeated after any one of about one week, two weeks, three weeks, four weeks, five weeks or six weeks. In some embodiments, the administration of the $O_2$ carrier polypeptide and radiation therapy is used in conjunction with another therapy; for example, a chemotherapy and/or immunotherapy.

In some embodiments of the invention, the $O_2$ carrier polypeptide (e.g. an H-NOX protein) is used in combination with chemotherapy. In some embodiments, the chemotherapy is a cytotoxin. Chemotherapeutic agents including cytotoxins are known in the art. In some embodiments, the cytotoxin is an alkylating agent. In some embodiments, the cytotoxin is cyclophosphamide or temozolomide. In some embodiments, the $O_2$ carrier polypeptide is administered before administration of the chemotherapy. In some embodiments, the $O_2$ carrier polypeptide is administered with administration of the chemotherapy. In some embodiments, the $O_2$ carrier polypeptide is administered after administration of the chemotherapy. In some embodiments, the $O_2$ carrier polypeptide is administered to the individual any of at least 1, 2, 3, 4, 5, 6, 7, 8, 10, 12, 14, 16, 18, 20, 22, or 24 hours or is administered daily or twice a day for 1, 2, 3, 4, 5, 6, or 7 days before administration of the chemotherapy. In some embodiments, the $O_2$ carrier polypeptide is administered to the individual any of at least 1, 2, 3, 4, 5, 6, 7, 8, 10, 12, or 24 hours after administration of the chemotherapy. In some embodiments, administration of the $O_2$ carrier polypeptide and/or administration of the chemotherapy is repeated any one of one, two, three, four, five, six, seven, eight, nine, ten times or more than ten times. In some embodiments, administration of the $O_2$ carrier polypeptide and/or administration of the chemotherapy is repeated after any one of about one week, two weeks, three weeks, four weeks, five weeks or six weeks. In some embodiments, administration of the $O_2$ carrier polypeptide and the chemotherapy are on the same dosing cycle. In some embodiments, administration of the $O_2$ carrier polypeptide and the chemotherapy are on different dosing cycles. In some embodiments, the admiration of H-NOX and radiation therapy is used in conjunction with another therapy; for example, radiation therapy and/or immunotherapy.

In some embodiments, the $O_2$ carrier polypeptide (e.g., an H-NOX protein) is administered to cancer patients prior to and/or in conjunction with an immunotherapy. In some embodiments, the immunotherapy is one or more of an anticancer vaccine, an adoptive immune cell therapy, an agent that targets an immune checkpoint regulator, an oncolytic virus or a BiTE. In some embodiments, the immunotherapy targets are one or more of CTLA-4, PD1, PD-L1, or an immune checkpoint regulator. In some embodiments, the immunotherapy is a dual PD1/CTLA-4 blockade therapy. In some embodiments, the immunotherapy is a PDL-1 treatment for patients with PDL1+ tumors or dual PD1/PD-L1 blockade. Nonlimiting examples include but are not limited to PD-1 and PDL-1 antagonists such as antibodies (e.g., Nivolumab). In some emobiments the checkpoint inhibitor is a CTLA4 antagonist such as an antibody (e.g., ipilumumab). In some embodiments, the immunotherapy is an adoptive T cell therapy including but not limited to chimeric antigen receptor T cells (e.g., CAR-T cells) or engineered TCR-T cells. In some embodiments, the immunotherapy is a Bispecific T cell Engagers (BiTE). In some embodiments, the immunotherapy includes one or more of anti-lymphocyte activation gene3 (LAG-3) therapy, anti-T cell immunoglobin mucin-3 (TIM-3) therapy, anti-killer immunoglobin-like receptos (KIR) thereapy, anti-4-1BB (CD137) agonizing/stimulatory therapy, or glucocorticoid-induced TNFR family related gene (GITR) agonizing/stimulatory therepy— each alone or in combinations with each other, and/or in combination with one or more of PD1, PDL-1, CTLA-4 or other therapies.

Nonlimiting examples of therapies that target checkpoint proteins other than PD-1/PDL-1 and CTLA4 negative regulators include both positive and negative (checkpoint inhibitors) regulators of immune response and can be antibodies or small molecules such as IDO (indoleamine-2.3 dioxygenase) pathway inhibitors such as direct IDO enzymatic activity inhibitors (e.g. NLG919), IDO effector pathway inhibitors (e.g. D-1-methyl-tryptophan, Indoximod, NLG8189), TDO (tryptophan 2,3-dioxygenase) inhibitors, or IDO-TDO dual inhibitors; Lymphocyte-activation gene 3 (LAG-3, CD223) antibody antagonists (e.g. IMP321, BMS-986016); Killer immunoglobulin-like receptors (KIRs) antagonists such as antibodies (e.g. lirilumab, IPH2101); T cell immunoglobulin mucin-3 (TIM-3) antagonists such as antibodies; B- and T cell attenuator (BTLA, CD272) antagonists such as antibodies; OX40 (CD134) agonists such as activating/stimulating antibodies; 4-1BB (CD137) agonists such as stimulatory antibodies (e.g. BMS-663513); Glucocorticoid-induced TNFR family related gene (GITR) agonists such as stimulatory antibodies (e.g. TRX518); and oncolytic viruses.

In some embodiments, the $O_2$ carrier polypeptide is administered before administration of the immunotherapy. In some embodiments, the $O_2$ carrier polypeptide is administered with administration of the immunotherapy. In some embodiments, the $O_2$ carrier polypeptide is administered after administration of the immunotherapy. In some embodiments, the $O_2$ carrier polypeptide is administered to the individual any of at least 1, 2, 3, 4, 5, 6, 7, 8, 10, 12, 24, or 48 hours before administration of the immunotherapy. In some embodiments, the $O_2$ carrier polypeptide is administered to the individual any of at least 3, 4, 5, 6, 7 or more days before administration of the immunotherapy. In some embodiments, the $O_2$ carrier polypeptide is administered to the individual any of at least 1, 2, 3, 4, 5, 6, 7, 8, 10, 12, 24 or 48 hours after administration of the immunotherapy. In some embodiments, the $O_2$ carrier polypeptide is administered to the individual any of at least 3, 4, 5, 6, 7 or more days after administration of the immunotherapy. In some embodiments, administration of the $O_2$ carrier polypeptide and/or administration of the immunotherapy is repeated any one of one, two, three, four, five, six, seven, eight, nine, ten times or more than ten times. In some embodiments, administration of the $O_2$ carrier polypeptide and/or administration of the immunotherapy is repeated after any one of about one week, two weeks, three weeks, four weeks, five weeks or six weeks. In some embodiments, administration of the $O_2$ carrier polypeptide and the immunotherapy are on the same dosing cycle. In some embodiments, administration of the $O_2$ carrier polypeptide and the immunotherapy are on different dosing cycles. In some embodiments, the admiration of H-NOX and radiation therapy is used in conjunction with another therapy; for example, radiation therapy and/or chemotherapy.

In some embodiments, the effectiveness of administration of the $O_2$ carrier polypeptide (e.g., H-NOX protein) is monitored; for example but not limited to tumor hypoxia, expression hypoxia-associated tumor suppressors and/or activators, presence of tumor-associated immune cells and/or immune cells directed against tumor cells and/or local (tumor biopsy, lymph node biopsy) or systemic (e.g. peripheral blood) cytokine and immune cell profiles. Methods to determine the level of tumor hypoxia are known in the art. Examples include but are not limited to measurement of any one of $^{18}F$-fluoromisonidazole (FMISO) tumor uptake, pimidazole uptake, $^{18}F$-fluoroazomycin arabinoside (FAZA) uptake, a nitroimidazole uptake, Copper (II)-diacetyl-bis (N4-methylthiosemicarbazone) (Cu-ATSM) uptake, hexafluorobenzene (C6F6) uptake by $^{19}F$ magnetic resonance imaging, hexamethyldisiloxane uptake by $^1H$ MRI, tumor HIF-1α expression, tumor HIF-2α expression, tumor HIF-3α expression, tumor Glut-1 expression, tumor pH (pH-weighted MRI) qBOLD, OE-MRI, MOBILE MRI tumor LDHA expression, tumor carbonic anhydrase IX (CA-9) expression, VEGF expression, or lactate and/or pyruvate levels. In some embodiments of the methods of monitoring, treating, and optimization of therapy described above, tumor hypoxia is measured by $^{18}F$-FMISO uptake. In some embodiments, $^{18}F$-FMISO uptake is measured by Positron emission tomography (PET) scan, computed tomography (CT) scan or computed axial tomography (CAT) scan. Methods to detect expression of genes such as HIF-1α, PD-L1 and A2AR are known in the art; for example, by immunoassay, by immunohistochemistry, by quantitative PCR, by hybridization (for example, on a gene chip), and the like.

Kits with H-NOX Proteins

Also provided are articles of manufacture and kits for the modulation of tumor immunity in an individual. In some embodiments, the article of manufacture or kit comprises any of the $O_2$ carrier polypeptides including any of the H-NOX proteins described herein including polymeric H-NOX proteins and PEGylated polymeric H-NOX proteins, and suitable packaging. In some embodiments, the invention includes a kit with (i) a H-NOX protein (such as a wild-type or mutant H-NOX protein described herein or formulations thereof as described herein) and (ii) instructions for using the kit to deliver $O_2$ to an individual.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of H-NOX proteins generally include information regarding dosage, dosing schedule, and route of administration for the intended treatment or industrial use. The kit may further comprise a description of selecting an individual suitable for treatment.

The containers may be unit doses, bulk packages (e.g., multi-dose packages) or sub-unit doses. For example, kits may also be provided that contain sufficient dosages of H-NOX proteins disclosed herein to provide effective treatment for an individual for an extended period, such as about any of a week, 2 weeks, 3 weeks, 4 weeks, 6 weeks, 8 weeks, 3 months, 4 months, 5 months, 6 months, 7 months, 8 months, 9 months, or more. Kits may also include multiple unit doses of H-NOX proteins and instructions for use and packaged in quantities sufficient for storage and use in pharmacies, for example, hospital pharmacies and compounding pharmacies. In some embodiments, the kit includes a dry (e.g., lyophilized) composition that can be reconstituted, resuspended, or rehydrated to form generally a stable aqueous suspension of H-NOX protein.

Exemplary Methods for Production of H-NOX Proteins

As noted above, the sequences of several wild-type H-NOX proteins and nucleic acids are known and can be used to generate mutant H-NOX domains and nucleic acids of the present invention. Techniques for the mutation, expression, and purification of recombinant H-NOX proteins have been described by, e.g., Boon, E. M. et al. (2005). *Nature Chemical Biology* 1:53-59 and Karow, D. S. et al. (Aug. 10, 2004). *Biochemistry* 43 (31): 10203-10211, U.S. Pat. Nos. 8,404,631 and 8,404,632, WO 2007/139791, and WO 2007/139767 which are hereby incorporated by reference in their entireties, particularly with respect to the mutation, expression, and purification of recombinant H-NOX proteins. These techniques or other standard techniques can be used to generate any mutant H-NOX protein.

A mutant H-NOX nucleic acid can be incorporated into a vector, such as an expression vector, using standard techniques. For example, restriction enzymes can be used to cleave the mutant H-NOX nucleic acid and the vector. Then, the compatible ends of the cleaved mutant H-NOX nucleic acid and the cleaved vector can be ligated. The resulting vector can be inserted into a cell (e.g., an insect cell, a plant cell, a yeast cell, or a bacterial cell) using standard techniques (e.g., electroporation) for expression of the encoded H-NOX protein.

In particular, heterologous proteins have been expressed in a number of biological expression systems, such as insect cells, plant cells, yeast cells, and bacterial cells. Thus, any suitable biological protein expression system can be utilized to produce large quantities of recombinant H-NOX protein. In some embodiments, the H-NOX protein (e.g., a mutant or wild-type H-NOX protein) is an isolated protein.

If desired, H-NOX proteins can be purified using standard techniques. In some embodiments, the protein is at least about 60%, by weight, free from other components that are present when the protein is produced. In various embodiments, the protein is at least about 75%, 90%, or 99%, by weight, pure. A purified protein can be obtained, for example, by purification (e.g., extraction) from a natural source, a recombinant expression system, or a reaction mixture for chemical synthesis. Exemplary methods of purification include immunoprecipitation, column chromatography such as immunoaffinity chromatography, magnetic bead immunoaffinity purification, and panning with a plate-bound antibody, as well as other techniques known to the skilled artisan. Purity can be assayed by any appropriate method, e.g., by column chromatography, polyacrylamide gel electrophoresis, or HPLC analysis. In some embodiments, the purified protein is incorporated into a pharmaceutical composition of the invention or used in a method of the invention. The pharmaceutical composition of the invention may have additives, carriers, or other components in addition to the purified protein.

In some embodiments, the polymeric H-NOX protein comprises one or more $His_6$ tags. An H-NOX protein comprising at least one $His_6$ tag may be purified using chromatography; for example, using $Ni^{2+}$-affinity chromatography. Following purification, the $His_6$ tag may be removed; for example, by using an exopeptidase. In some embodiments, the invention provides a purified polymeric H-NOX protein, wherein the polymeric H-NOX protein was purified through the use of a $His_6$ tag. In some embodiments, the purified H-NOX protein is treated with an exopeptidase to remove the $His_6$ tags.

In some embodiments, H-NOX protein comprises one or more molecules of polyethylene glycol (i.e., PEGylated). Methods to produce PEGylated proteins are known in the art.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Unless indicated otherwise, temperature is in degrees Centigrade and pressure is at or near atmospheric.

Figure 6A:
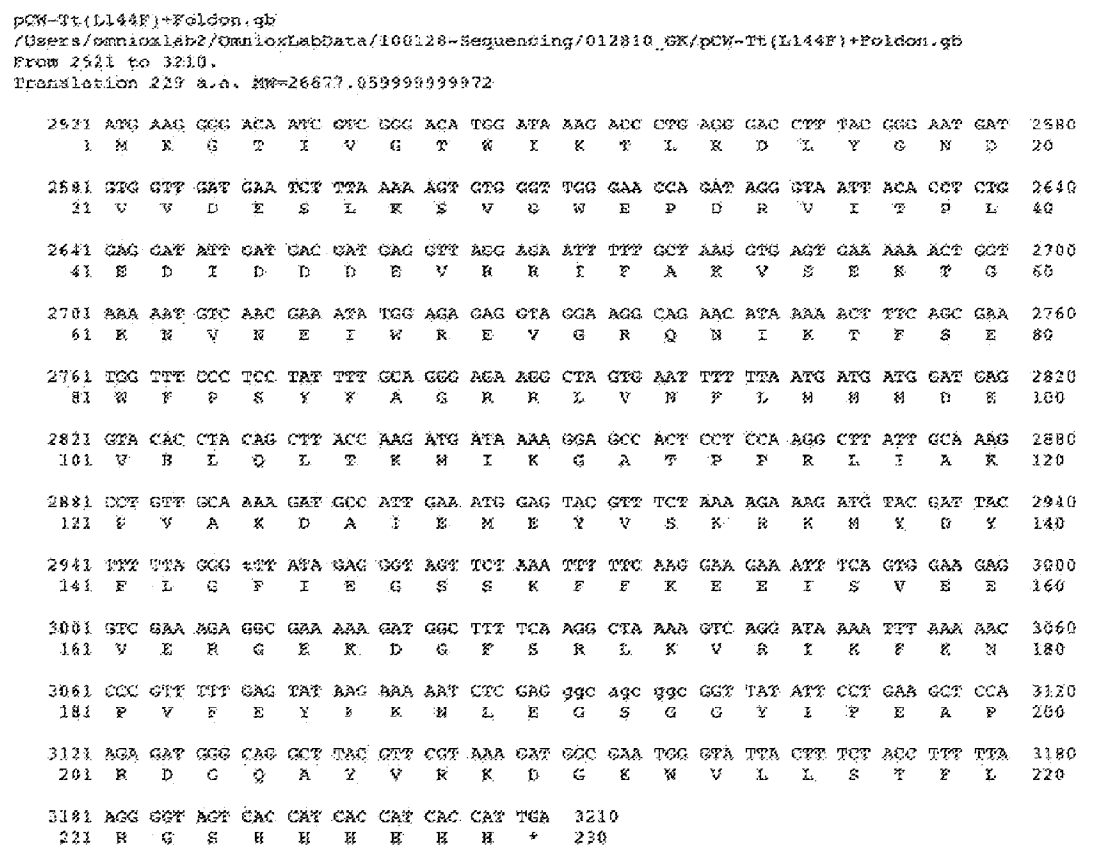
Figure 6B:
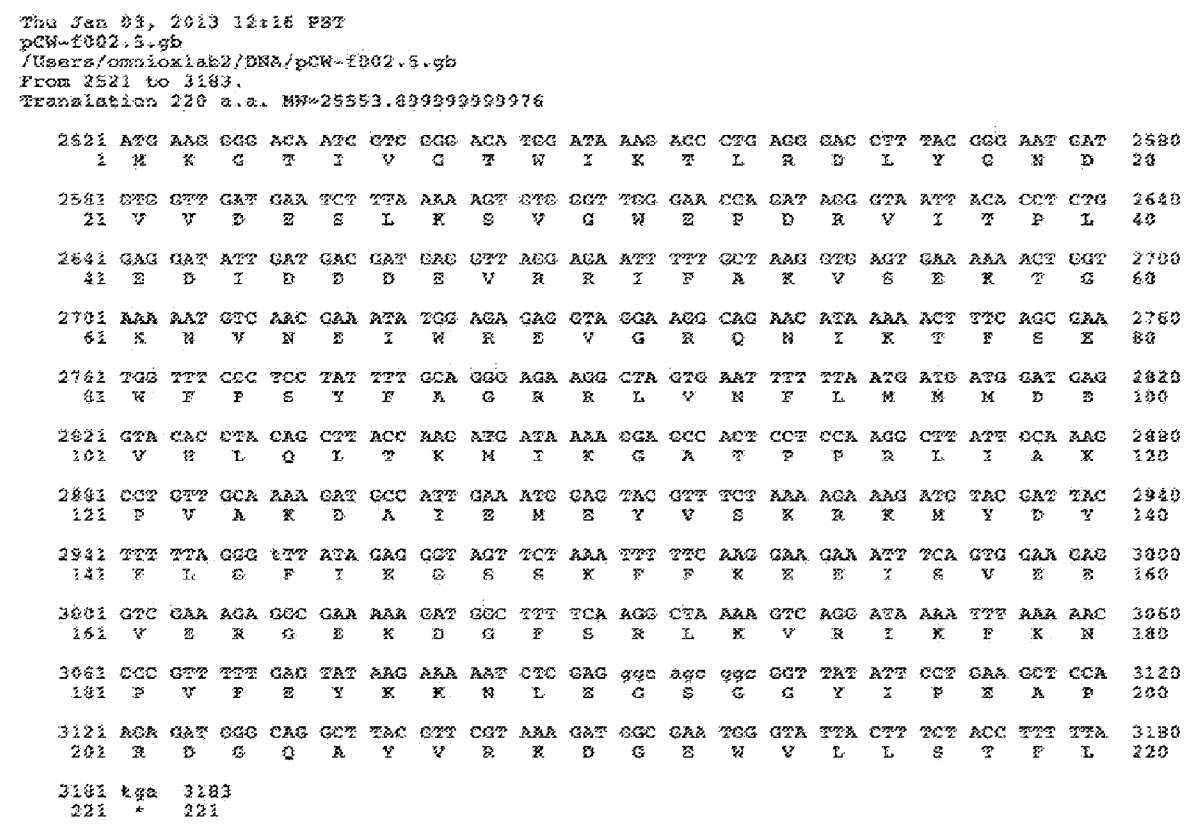

Example 1. H-NOX Enables Efficient Oxygenation of Hypoxic Tumor Microenvironments A PEGylated trimeric *Thermoanaerobacter tengcongensis* (Tt.) H-NOX bearing a L144F substitution in the distal pocket (FIG. 6B) was evaluated for the ability to oxygenate tumor microenvironments and increase radiation sensitivity. Administration of the PEGylated trimeric Tt H-NOX L144F to mice bearing hypoxic tumors induces rapid and sustained oxygenation of the tumors as directly measured by the external hypoxia marker, pimonidazole, hypoxia inducible transcription factor 1 alpha, HIF-1-α, and OxyLite oxygen-sensing nanofiber (FIGS. 2 and 3, respectively).

Mice bearing H460 subcutaneous xenograft tumors were injected i.v. with PEGylated trimer H-NOX (L144F) at 650 mg/kg when tumor volume reached ~300-350 $mm^3$ (~10-14 days after tumor cell subcutaneous implantation). Prior to euthanasia, mice were injected with the exogenous hypoxia marker pimonidazole at 60 mg/kg and tumors were harvested. Pimonidazole (FIG. 2A) (Hypoxyprobe-1) and HIF-1α (FIG. 2B) levels were measured by competitive (pimonidazole) and sandwich (HIF-1α, Abcam) ELISAs, respectively. Graphs show quantification of pimonidazole and HIF-1α signals after PEGylated H-NOX (L144F) administration. Vehicle, 1 h and 4 h: n=22, 7 h: n=18, 12 h: n=16, 24 h: n=6. Results from 4 independent experiments. Mean values+/−SEM. **$p<0.0001$, *$p<0.001$, **$p<0.01$, * $p<0.05$ by one-way ANOVA and Bonferroni's post-hoc tests. (FIG. 2C) Tumors were assessed for the accumulation of PEGylated H-NOX (L144F) by sandwich H-NOX ELISA at 1, 4, 7, 16 and 24 hours after injection and results expressed per gram of tumor tissue. Seven to eight week old Nu/Nu female mice were subcutaneously implanted with $3 \times 10^6$ of H460 human lung cancer cells and monitored until the tumors reached average size of ~300 $mm^3$ (10-14 days post-implantation of tumor cells). Mice bearing 200-350 $mm^3$ xenograft tumors were injected i.v. with bolus vehicle (formulation buffer: 50 mM succinate, 50 mM NaCl, 3.4 mM EDTA, and 10 mM reduced glutathione at pH 7) or formulation buffer containing 650 mg/kg of PEGylated trimer H-NOX (L144F). To measure tumor hypoxia, prior to euthanasia, mice were injected with the exogenous hypoxia marker pimonidazole at 60 mg/kg. Tumors were harvested and homogenized in an extraction buffer (Abcam kit #ab117996) supplemented with anti-proteases. Protein concentration was quantified in each tumor using a Bradford assay. Samples were assayed for pimonidazole (Hypoxyprobe-1) amount using a competitive ELISA assay developed by Omniox and for HIF-1α using the Abcam ELISA kit (ab117996).

In H460 lung carcinoma mouse model maximum oxygenation was achieved between 4 h and 8 h and it correlated with the peak of H-NOX (L144F) tumor accumulation as assessed by ELISA (FIG. 2C).

For assessment of the H-NOX (L144F) tumor accumulation, tumors were harvested at different timepoints after injection. Tumors were homogenized in an extraction buffer (Abcam kit #ab117996) supplemented with anti-proteases and protein concentration was quantified in each tumor using a Bradford assay. PEGylated H-NOX (L144F) concentration was quantified by a sandwich ELISA for H-NOX developed by Omniox and normalized to tumor weight.

While supplemental oxygenation of animals successfully increased oxygenation of mouse tumor tissue at 5-10 mmHg oxygen concentration, it had no effect on regions with lower oxygen levels (<5 mmHg). By contrast, PEGylated trimer Tt H-NOX L144F is capable of increasing oxygenation even in severely hypoxic tumor tissue (<5 mmHg). This is likely due to PEGylated trimer Tt H-NOX L144F's superior tissue penetration that enables oxygen delivery to areas beyond oxygen gradient diffusion limits. Moreover, while maximum supplemental oxygenation of mouse tumors is achieved with exposing animals continuously to 95%-100% breathing oxygen [increasing risk of hyperoxic and inflammatory damage to the normal tissues (Kallet & Matthay, 2013 Respir Care, 58 (1): 123-141; Thiel et al., 2005 PLOS Biol, 3 (6), e174)], single bolus i.v. dose of PEGylated trimer Tt H-NOX L144F can maintain tissue oxygenation for more than 7 hours without increasing oxygen levels in normal tissues. A control Tt H-NOX protein (wild type variant)—that is not capable of releasing oxygen at oxygen concentrations present in hypoxic tissues—did not have any effect on tumor oxygenation (FIG. 3C).

Seven to eight week old Nu/Nu female mice were subcutaneously implanted with $3 \times 10^6$ of H460 human lung cancer cells and monitored until the tumors reached average size of ~500 mm$^3$ (10-18 days post-implantation of tumor cells). Mice bearing H460 tumors were anesthetized with isoflurane mixed in 20% of oxygen and the OxyLite™ probe (Oxford Optronix, UK) was implanted into H460 subcutaneous xenograft tumors using a micromanipulator. The OxyLite™ consists of the ruthenium chloride dye held in a polymer matrix of 230 μm in diameter at the tip. After equilibration for ~20-30 minutes, pO$_2$ was measured using optical fluorescence sensors attached to a four-channel unit. A low starting pO$_2$ confirmed entry into hypoxic tissue away from neighbouring blood vessels (~0.2 mmHg; except in FIG. 3D where 5 mmHg). After probe implantation, probe was left for ~20-30 min in order for pO$_2$ measurements to stabilize, and mice were given to respire 100% O$_2$ (FIG. 3B, FIG. 3D) or were injected with PEGylated H-NOX (L144F in FIG. 3A, wt in FIG. 3C) and fluorescent quenching was recorded.

Figure 4:
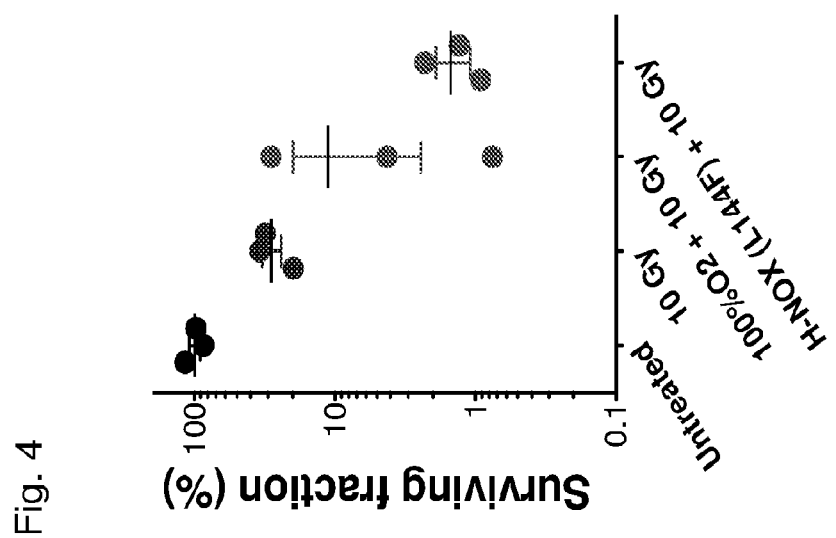
FIG. 4 shows enhancement of radiation efficacy following PEGylated trimer Tt H-NOX L144F treatment of mice bearing H460 tumors. Mice bearing H460 subcutaneous xenograft tumors (150-300 mm³) were either pre-treated with PEGylated trimer Tt H-NOX L144F or treated with 10 Gy alone, irradiated, tumors extracted and processed for clonogenic assay. Cell numbers were counted 7 days later in triplicate samples from each tumor. Each dot on the graph represents average surviving fraction for one tumor.

The superior ability of PEGylated trimer Tt H-NOX L144F to deliver oxygen to hypoxic tumor regions relative to the administration of the hyperoxic gas was further demonstrated by more efficient radiation tumor cell kill (FIG. 4).

Mice bearing H460 subcutaneous xenograft tumors (200-350 mm$^3$) were treated with 10 Gy alone or in combination with 650 mg/kg of PEGylated trimer H-NOX (L144F) injected i.v. 7 hours prior to irradiation. Tumors were extracted after irradiation and processed for clonogenic assay. Cell numbers were counted 10-14 days later in triplicate samples from each tumor. Each dot on the graph represents average surviving fraction for one tumor. Mean values+/−SEM (n=3 per experiment). Seven to eight week old Nu/Nu female mice were subcutaneously implanted with $3 \times 10^6$ of H460 human lung cancer cells and monitored until the tumors reached average size of ~300 mm$^3$ (10-14 days post-implantation of tumor cells). Mice bearing 200-350 mm$^3$ xenograft tumors were irradiated with 10 Gy alone or in combination with intravenous delivery of either a bolus vehicle (formulation buffer: 50 mM succinate, 50 mM NaCl, 3.4 mM EDTA, and 10 mM reduced glutathione at pH 7) or a formulation buffer containing 650 mg/kg of PEGylated H-NOX (L144F). Mice were sacrificed after irradiation and tumors were harvested and processed for an ex-vivo clonogenic assay. Briefly, tumors cells were minced into fine pieces with a scalpel and digested for ~30 minutes with an enzymatic cocktail containing a mix of collagenase (200 U/ml), hyaluronidase (200 U/ml) and DNAse (10 ml of cocktail/g of tumor). Extracted cells were then counted and seeded at 500/125/25 cells per well for untreated and 2000/500/100 cells per well for irradiated tumor samples in a 6 well plate in duplicate. After 10-12 days, cell colonies were fixed with PFA and stained with crystal violet. The number of clones (over 50 cells) was counted and the plating efficiency was calculated in untreated samples (number of cells counted in well÷number of cells plated×100). Surviving fraction was calculated in all samples (number of cells counted÷plating efficiency×100).

Following PEGylated trimer Tt H-NOX L144F administration, there was >15-fold increase in radiation treatment efficacy in all PEGylated trimer Tt H-NOX L144F-treated tumors that reduced the surviving fraction of tumor cells from 30% in the 10 Gy treatment alone group to <2% in the H-NOX (L144F)-pretreated tumor. In the same experiment, treatment of mice bearing tumors with 100% oxygen showed variable increase in radiation enhancement (~3 fold) probably resulting from unequal tumor oxygenation between individual tumors likely due to uneven vascular density between tumors.

Example 2. H-NOX Acts as an Immunoactivator Enhancing Host Anti-Tumor Responses

PEGylated trimer Tt H-NOX L144F-induced oxygenation inhibits the HIF-1α pathway (FIG. 2B) and relieves HIF-1α-dependent and HIF-1α-independent tumor immunosuppression. Mice bearing H460 subcutaneous xenograft tumors (200-350 mm$^3$) were either treated with vehicle alone or with PEGylated trimer H-NOX (L144F) and harvested 7, 16 or 24 hours after injection for qRT-PCR analysis. Mean values+/−SEM. N=5-6 per group, *p<0.05 by t-test. Treatment with a single dose of H-NOX resulted in significant downregulation of HIF-1α and its effectors including direct and indirect modulators of the host's immune response: PD/PDL-1 and VEGF signaling, metabolic and growth factor regulators (FIG. 5).

Seven to eight week old Nu/Nu female mice were subcutaneously implanted with $3 \times 10^6$ of H460 human lung cancer cells and monitored until the tumors reached average size of ~300 mm$^3$ (10-14 days post-implantation of tumor cells). Mice bearing 200-350 mm$^3$ xenograft tumors were injected with either a bolus vehicle (formulation buffer: 50 mM succinate, 50 mM NaCl, 3.4 mM EDTA, and 10 mM reduced glutathione at pH 7) or a formulation buffer containing 650 mg/kg of PEGylated trimer H-NOX (L144F). To prepare samples for qRT-PCR analysis, mice were sacrificed and tumors excised. Total RNA was extracted from tumor samples using the RNeasy kit (QIAGEN) according to the manufacturer instructions. Reverse transcription and real-time PCR (RT-PCR) on a StepOnePlus™ Real-Time PCR System (Applied Biosystems) were performed as described. 25 μL reaction was prepared using 2 μL of cDNA template, 12.5 μL of SYBR® Green PCR Master Mix (Applied Biosystems) and 1 μL of the following sense and antisense primers: VEGF: forward, 5'-CAATCGA-GACCCTGGTGGA ~3' (SEQ ID NO:23); reverse, 5'-GCACACACTCCAGGCCCT-3' (SEQ ID NO:24); Glut1: forward, 5'-CAACCAGACATGGGTCCAC-3' (SEQ ID NO:25); reverse, 5'-GTTAACGAAAAGGCC-CACAGA-3' (SEQ ID NO:26); PDL1: forward, 5'-GTTGTGGATCCAGTCACCTCT-3' (SEQ ID NO:27); reverse, 5'-GATTCTCAGTGTGCTGGTCAC-3' (SEQ ID NO:28); L7: forward, 5'-CAAGGAGGAAGCTTATCTAT-GAA-3' (SEQ ID NO:29); reverse, 5'-AT-TTGACGAAGGCGAAGAAGCT-3' (SEQ ID NO:30). Thermocycling conditions were as follows: initial step was 10 min at 95° C., then 40 cycles of 15 s denaturation at 95° C. followed by 1 min annealing and extension at 60° C. Results were analyzed with the StepOne Software v2.0 using the comparative CT method. Transcripts of gene of interest were normalized against the transcripts of the mouse ribosomal protein L7 housekeeping gene, and were presented as fold change relative to the L7 transcript content.

For example, PEGylated trimer Tt H-NOX L144F-mediated downregulation of the HIF-1α and A2AR adenosinergic signaling may result in activation and recruitment of effector T cells to the tumor tissue leading to increased lymphocyte tumor infiltration, decrease in metastatic tumor growth and tumor regression. Furthermore, H-NOX-induced oxygenation of tumors may reduce immunoevasion of tumor cells by inhibiting multiple hypoxia-dependent mechanisms including downregulation of MHC1 and upregulation of PDL-1 expression on tumor cell surface, and activation and recruitment of myeloid-derived suppressor cells (MDSC) including TAMs that directly suppress immune effector cells as well as promote angiogenesis and metastasis (see FIG. 1B). H-NOX treatment may inhibit recruitment of macrophages to TME by downregulating VEGF, CSF1 and other HIF-1-dependent cytokine signaling (Chaturvedi et al., 2014 Proc Natl Acad Sci USA, 111 (20): E2120-2129; Lewis & Hughes, 2007 Breast Cancer Res, 9 (3): 209) as well as HIF-1- and HIF-2-mediated macrophage activation (Fang et al., 2009 Blood, 114 (4): 844-859; Takeda et al., 2010 Genes Dev, 24 (5): 491-501).

Finally, in stimulating host's anti-tumor immune response, H-NOX may act as co-activator enhancing other targeted cancer immunotherapies such as, but not limited to, anti-PD1 (programmed cell death protein 1), anti-PDL-1 (programmed cell death protein ligand 1), anti-CTLA-4 or therapies targeting other immune checkpoints' regulators, anti-cancer vaccines, adoptive immune cell therapies or combinations thereof. For example, H-NOX may be administered to cancer patients prior to and in conjunction with dual PD1/CTLA-4 blockade therapy or in combination with PDL-1 treatment in patients with PDL1+ tumors. It may also act as an adjuvant to other cancer treatments including, but not limited to, chemotherapy, radiation therapy or other non-immune targeted or cell-based therapies that may benefit from active anti-tumor immune defenses. Indeed, H-NOX may synergize with radiation by simultaneously stimulating anti-tumor immune response towards radiation exposed tumor-specific antigens from damaged tumor tissue (Demaria et al., 2005 Int J Radiat Oncol Biol Phys, 63 (3), 655-666) and oxygen-dependent tumor cell killing (Brown, 2010 Int J Radiat Biol, 86 (11), 907-917). During radiotherapy, H-NOX may also act as normal tissue radioprotectant by ameliorating hypoxia resulting from radiation-induced vascular damage.

Example 3. Measurement of Hypoxia and T Cells in B16F10 and CT26 Subcutaneous Tumors and Intracranial GL261-Luciferase Tumors Generation of B16F10 and CT26 subcutaneous tumors and intracranial GL261-luciferase tumors. Six to eight week old C57BL/6J female mice were subcutaneously implanted with 1×10$^6$ B16F10 mouse melanoma cancer cells on the flank (FIG. 7A). Six to eight week old BALB/c female mice were subcutaneously implanted with 1×10$^6$ CT26 colon tumor cells on the flank (FIG. 7B). Male C57BL/6J weighing 20 g were injected with 3×10$^5$ GL261-luc cells intracranially into the right caudate nucleus (+0.5 mm A/P, +2.3 mm M/L and −3.2 mm D/V) (FIG. 7C). Intracranial tumors were allowed to grow for 21 days before sacrifice. Subcutaneous tumors were measured 3 times a week using calipers and tumor size was calculated based on the formula: (length×width$^2$)÷0.5. Once the tumors reached an average size of ~300 mm$^3$ (10-14 days post-implantation of tumor cells), treatment was initiated.

Treatment. Mice bearing 200-400 mm$^3$ subcutaneous tumors or day 21 intracranial tumors were injected with the exogenous hypoxia marker pimonidazole ip. (60 mg/kg, Hypoxyprobe, Burlington Massachusetts) 1-8 hours prior to sacrifice.

Immunohistochemistry. Rodents were euthanized and tumors resected for immunohistochemistry (IHC) assay. Tumors were frozen in OCT and sectioned at 12 μM for IHC processing. Sections were fixed with 4% PFA for 15 minutes at 4° C., then blocked and permeabilized with 5% BSA, 5% goat serum, and 0.1% Tween 20 for 1-2 hours at room temperature. Sections were then incubated with rabbit anti-pimonidazole (Hypoxyprobe, 1:100) (FIGS. 7A, 7B, 7C, top panels) and rat anti-CD3, rat anti-CD4 (Biolegend, 1:50) or rat anti-CD8 (Biolegend, 1:50) antibodies overnight at 4° C. (FIGS. 7A, 7B, 7C, middle panels), followed by anti-rabbit or anti-rat secondary antibodies (1:1000, Jackson Immunoresearch Laboratories, West Grove, PA, USA) for 2 hours at room temperature. The sections were mounted in Slow-Fade DAPI (Invitrogen). Sections were imaged with an HD AxioImager Zeiss microscope equipped with a CCD digital camera. Quantification. In each animal, the number of CD3+, CD4+ or CD8+ T cells was counted in pimonidazole-positive and pimonidazole-negative areas in 2-4 pictures per section in 5 tumor sections spanning 1-1.5 mm of the tumor thickness. The sum of CD4+ and CD8+ cells in each area was divided by the sum of pimonidazole-positive and pimonidazole-negative areas to obtain the total number of T cells per mm$^2$ of tumor tissue (FIGS. 7A, 7B, and 7C, bottom panels). Hypoxic regions of tumors (H) showed 2.5 to over 10-fold less T cells than normoxic regions (N).

Example 4. H-NOX Treatment of Hypoxic Tumors

Generation of B16F10 subcutaneous tumors. Six to eight week old C57BL/6J female mice were subcutaneously implanted with 1×10$^6$ of B16F10 mouse melanoma cancer cells on the flank. Tumors were measured 3 times a week using calipers and tumor size was calculated based on the formula: (length×width$^2$)÷0.5. Once the tumors reached an average size of ~300 mm$^3$ (10-14 days post-implantation of tumor cells), treatment was initiated.

Treatment. Mice bearing 200-400 mm$^3$ tumors were randomized in each treatment group based on tumor size and injected intratumorally with vehicle (formulation buffer: 50 mM succinate, 50 mM NaCl, 3.4 mM EDTA, and 10 mM reduced glutathione at pH 7) or 100 μl of formulation buffer containing 2 mg of PEGylated H-NOX (L144F). One hour prior to vehicle or H-NOX treatment, mice were injected with the exogenous hypoxia marker pimonidazole ip. (60 mg/kg, Hypoxyprobe, Burlington Massachusetts).

Figure 8:
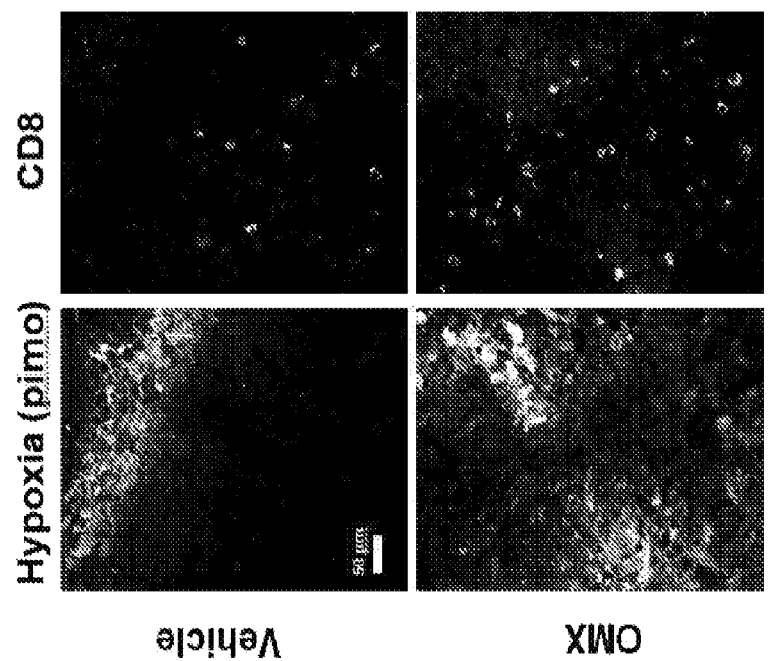
FIG. 8 shows quantification of CD8 T cells in hypoxic areas of tumors after H-NOX treatment (OMX) or vehicle control treatment (Veh). Representative images are shown. Hypoxic areas were labeled with pimondazole by immunohistochemical analysis. Following OMX treatment there is an increase in CD4 (data not shown) and CD8 T cell infiltration into regions of tumors that were hypoxic prior to OMX administration.
Figure 9A:
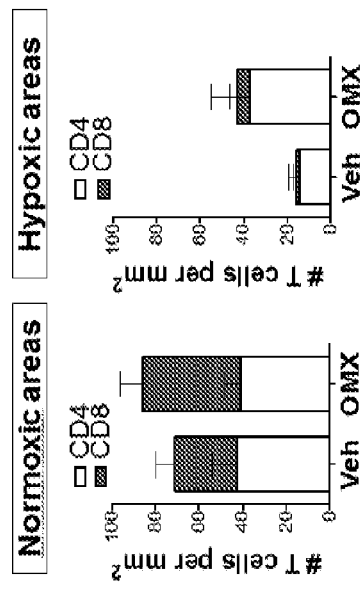
FIGS. 9A and 9B show quantification of T cells in normoxic and hypoxic areas of tumors after H-NOX treatment (OMX) or vehicle control treatment (Veh). Both CD4 and CD8 T cells were evaluated. Tumor areas evaluated included areas on the periphery of the tumor and in the tumor center. Results of quantitative image analysis of multiple sections are shown in FIG. 9A and representative images in FIG. 9B. Hypoxic areas were labelled using immunohistochemical analysis of carbonic anhydrase IX (CAIX) expression. Following OMX treatment, there is an increase in CD4 and CD8 T cell infiltration into regions of tumors that were hypoxic prior to OMX administration.
Figure 9B:
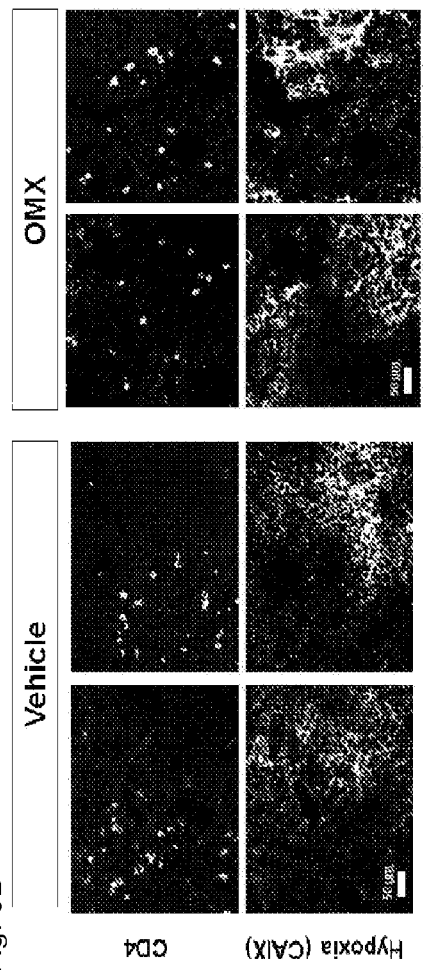

Immunohistochemistry. 6 hours after H-NOX injection, rodents were euthanized and tumors resected for immunohistochemistry (IHC) assay. Tumors were frozen in OCT and sectioned at 12 μM for IHC processing. Sections were fixed with 4% PFA for 15 minutes at 4° C., then blocked and permeabilized with 5% BSA, 5% goat serum, and 0.1% Tween 20 for 1-2 hours at room temperature. Sections were then incubated with rabbit anti-pimonidazole (Hypoxyprobe, 1:100) or rabbit anti-carbonic anhydrase IX (CAIX, Novus Biological 1:1000) and rat anti-CD4 (Biolegend, 1:50) or rat anti-CD8 (Biolegend, 1:50) antibodies overnight at 4° C., followed by anti-rabbit or anti-rat secondary antibodies (1:1000, Jackson Immunoresearch Laboratories, West Grove, PA, USA) for 2 hours at room temperature. The sections were mounted in SlowFade DAPI (Invitrogen). Sections were imaged with an HD AxioImager Zeiss microscope equipped with a CCD digital camera (FIGS. 8 and 9B).

Quantification. In each animal, the number of CD4+ and CD8+ T cells was counted in pimonidazole-positive, pimonidazole-negative, CAIX-positive and CAIX-negative areas in 4 pictures per section in 5 tumor sections spanning 1-1.5 mm of the tumor thickness. The sum of CD4+ and CD8+ cells in each area was divided by the sum of pimonidazole-positive, pimonidazole-negative, CAIX-positive and CAIX-negative areas to obtain the total number of T cell per mm$^2$ of tumor tissue. Results shown in FIGS. 8 and 9A demonstrate that OMX treatment as compared to the vehicle control (formulation buffer) enhances accumulation of CD4+ and CD8+ lymphocytes in previously pimondazole-negative (FIG. 8) ro CAIX-negative (FIG. 9B) labeled hypoxic regions of the tumors.

Example 5. Measurement of Tumor Hypoxia and Tumor Vessels

Generation of H460, B16F10 and CT26 subcutaneous tumors and intracranial GL261-luciferase tumors. Seven to eight week old Nu/Nu female mice were subcutaneously implanted with 3×10$^6$ of H460 human lung cancer cells in the hind limb. Six to eight week old C57BL/6J female mice were subcutaneously implanted with 1×10$^6$ B16F10 mouse melanoma cancer cells on the flank. Six to eight week old BALB/c female mice were subcutanously implanted with 1×10$^6$ CT26 colon tumor cells on the flank. Male C57BL/6J weighting 20 g were injected with 3×10$^5$ GL261-luc cells intracranially into the right caudate nucleus (+0.5 mm A/P, +2.3 mm M/L and −3.2 mm D/V). Intracranial tumors were allowed to grow for 21 days before sacrifice. Subcutaneous tumors were measured 3 times a week using calipers and tumor size was calculated based on the formula: (length×width$^2$)+0.5. Once the tumors reached an average size of ~300 mm$^3$ (10-14 days post-implantation of tumor cells), treatment was initiated. Treatment. Mice bearing 200-400 mm$^3$ subcutaneous tumors or day 21 intracranial tumors were injected with the exogenous hypoxia marker pimonidazole ip. (60 mg/kg, Hypoxyprobe, Burlington Massachusetts) 1-8 hours prior to sacrifice.

Figure 10:
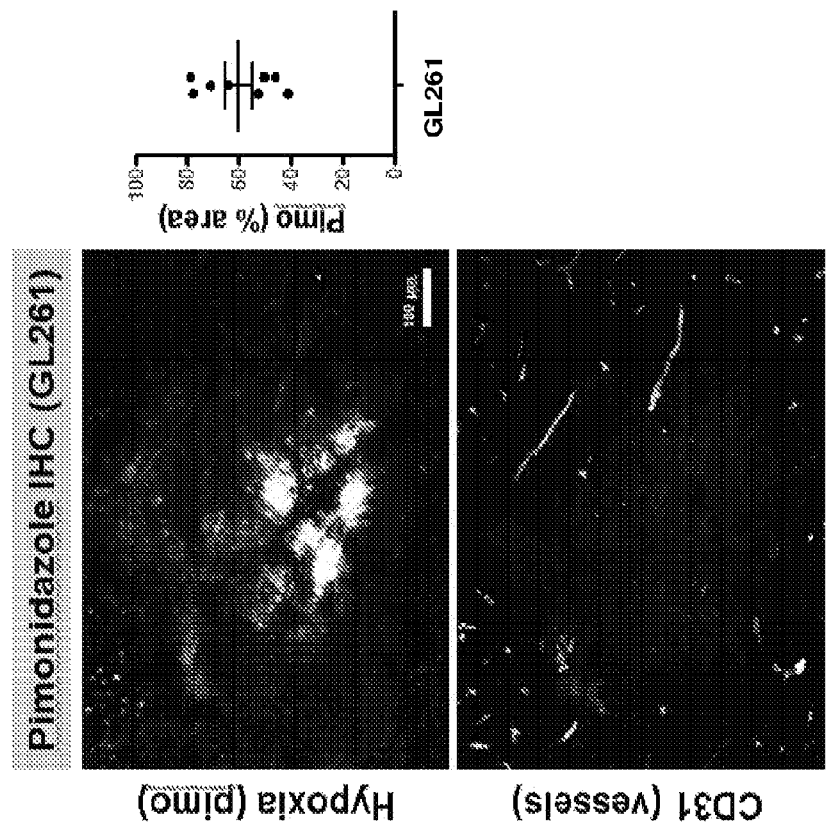
FIG. 10 shows the results of immunohistochemistry for hypoxia (pimondazole) and CD3 vessels is GL261 tumor model.

Immunohistochemistry and ELISA. Rodents were euthanized and tumors resected for immunohistochemistry (IHC) and ELISA assays. For ELISA, B16F10, CT26 and H460 tumors were homogenized in an extraction buffer (Abcam kit #ab117996) supplemented with anti-proteases. Protein concentration was quantified in each tumor using a Bradford assay and samples were assayed for hypoxia levels using a competitive Pimonidazole (Hypoxyprobe-1, Hypoxyprobe, Burlington Massachusetts) ELISA assay. For IHC, GL261 tumors were frozen in OCT and sectioned at 12 µM for IHC processing. Sections were fixed with 100% methanol for 20 minutes at −20° C., then blocked and permeabilized with 5% BSA, 5% goat serum, and 0.1% Tween 20 for 1-2 hours at room temperature. Sections were then incubated with rabbit anti-pimonidazole (Hypoxyprobe, 1:100) and rat anti-CD31 (BD Bioscience, 1:50) antibodies overnight at 4° C., followed by anti-rabbit or anti-rat secondary antibodies (1:1000, Jackson Immunoresearch Laboratories, West Grove, PA, USA) for 2 hours at room temperature. The sections were mounted in SlowFade DAPI (Invitrogen). Sections were imaged with an HD AxioImager Zeiss microscope equipped with a CCD digital camera (FIG. 10).

Quantification. For the pimonidazole ELISA, quantification of the IC$_{50}$ values ("Kd") were performed with a 5-parameter fit of the standard curve and values were normalized according to the protein concentration in each sample. For GL261 IHC, in each animal, the percent of pimonidazole+ area within the tumor tissue was determined using ImageJ (1-2 pictures per section in 5 tumor sections spanning 1 mm of the tumor thickness) (FIG. 10). These data show that while there is a range in the levels of hypoxia between individual animals and between tumor types, its presence is significant in a majority of the tumors of the examined sizes.

Example 6. Measurement of H-NOX Accumulation in Tumors

Generation of B16F10 and CT26 subcutaneous tumors and intracranial GL261-luciferase tumors. Six to eight week old C57BL/6J female mice were subcutaneously implanted with 1×10$^6$ B16F10 mouse melanoma cancer cells on the flank. Six to eight week old BALB/c female mice were subcutanously implanted with 1×10$^6$ CT26 colon tumor cells on the flank. Male C57BL/6J weighting 20 g were injected with 3×10$^5$ GL261-luc cells intracranially into the right caudate nucleus (+0.5 mm A/P, +2.3 mm M/L and −3.2 mm D/V). Intracranial tumors were allowed to grow for 21 days before sacrifice. Subcutaneous tumors were measured 3 times a week using calipers and tumor size was calculated based on the formula: (length×width$^2$)=0.5. Once the tumors reached an average size of ~300 mm$^3$ (10-14 days post-implantation of tumor cells), treatment was initiated.

Treatment. Mice bearing 200-400 mm$^3$ subcutaneous tumors were randomized in each treatment group based on tumor size and injected intravenously (650 mg/kg), subcutaneously (650 mg/kg), or intratumorally (2 mg, 100 µl) with vehicle (formulation buffer: 50 mM succinate, 50 mM NaCl, 3.4 mM EDTA, and 10 mM reduced glutathione at pH 7) or formulation buffer containing PEGylated H-NOX (L144F). Mice bearing day 21 intracranial tumors were randomized in each treatment group based on bioluminescent signal measured with the Xenogen IVIS spectrum and injected intravenously with formulation buffer alone or containing 750 mg/kg of H-NOX (L144F).

Measurement of PEGylated H-NOX (L144F) accumulation in subcutaneous tumor tissue. Tumors were harvested 6 h (B16F10) or 8 h (CT26) after H-NOX or vehicle injection. Tumors were homogenized in an extraction buffer (Abcam kit #ab117996) supplemented with anti-proteases and protein concentration was quantified in each tumor using a Bradford assay. PEGylated H-NOX (L144F) concentration was quantified by a sandwich ELISA ELISA (detection sensitivity at 1 ng/ml) for H-NOX and normalized to tumor weight to express H-NOX amount in µg/g tumor tissue. Quantification of H-NOX levels in tumor lysates was determined by 5-parameter fit of the standard curve.

Biodistribution of H-NOX (L144F) in GL261 by IHC. 2 h after H-NOX injection, rodents were euthanized and tumors resected for immunohistochemistry (IHC) assay. Tumors were frozen in OCT and sectioned at 12 µM for IHC processing. Sections were fixed with 100% methanol for 20 minutes at −20° C., then blocked and permeabilized with 5% BSA, 5% goat serum, and 0.1% Tween 20 for 1-2 hours at room temperature. Sections were then incubated with rabbit anti-H-NOX (1:500, custom-made rabbit polyclonal produced by AnaSpec Inc, Fremont, CA) and rat anti-CD31 (BD Bioscience, 1:50) antibodies overnight at 4° C., followed by anti-rabbit or anti-rat secondary antibodies (1:1000, Jackson Immunoresearch Laboratories, West Grove, PA, USA) for 2 hours at room temperature. The sections were mounted in SlowFade DAPI (Invitrogen). Sections were imaged with an HD AxioImager Zeiss microscope equipped with a CCD digital camera. In each animal, the percent of H-NOX-positive area within the tumor tissue was determined using ImageJ (1-2 pictures per section in 5 tumor sections spanning 1 mm of the tumor thickness).

Example 7. Measurement of Hypoxia and T Cells in Canine Oral Melanoma Tumors

Canine oral melanoma. Pet dogs with oral melanoma tumors were recruited for the study with owners' consent and injected intravenously (slow infusion) with PEGylated H-NOX (L144F) 4 h prior to surgery. Tissue extracted from surgery was analyzed by IHC.

Figure 11:
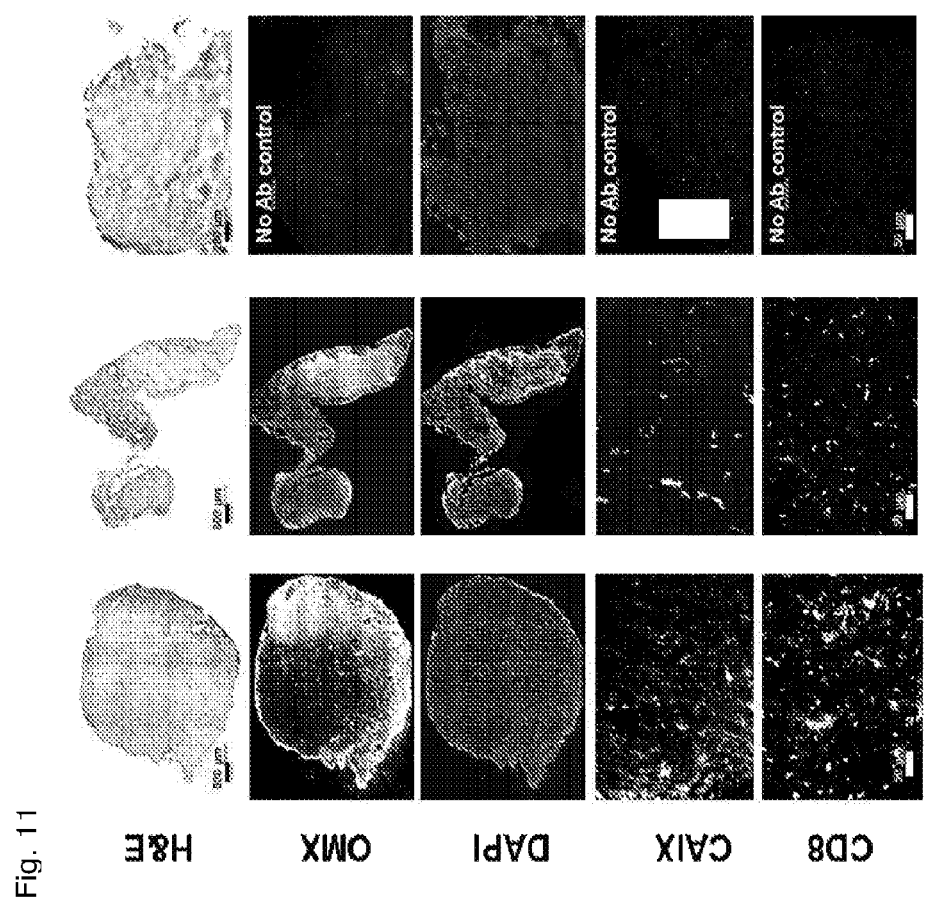
FIG. 11 shows immunohistochemical analysis of H-NOX tumor penetration, tumor hypoxia and CD8 T cell localization in canine oral melanoma tumors. Tissues were stained with hematoxylin and eosin (H&E), DNA interchelating dye (DAPI) and with anti-H-NOX (OMX), -carbonic anhydrase IX (CAIX) and -CD8 antibodies to assess CD8 lymphocyte localization in tumor regions that were hypoxic prior to H-NOX (OMX) treatment. Images reveal CD8 positive T cells localized throughout regions of the tumor that were hypoxic prior to H-NOX (OMX) treatment (CAIX positive).

Immunohistochemistry. 4 hours after H-NOX injection, tumors were resected, frozen in OCT and sectioned at 12 μM for IHC processing. Sections were fixed with 4% PFA for 15 minutes at 4° C., then blocked and permeabilized with 5% BSA, 5% goat serum, and 0.1% Tween 20 for 1-2 hours at room temperature. Sections were then incubated with rabbit anti-carbonic anhydrase IX (CAIX, Novus Biological 1:1000) or rabbit anti-H-NOX (1:500, custom-made rabbit polyclonal produced by AnaSpec Inc, Fremont, CA) and rat anti-CD4 (Abd Serotech, 1:50) or rat anti-CD8 (Abd Serotech, 1:50) antibodies overnight at 4° C., followed by anti-rabbit or anti-rat secondary antibodies (1:1000, Jackson Immunoresearch Laboratories, West Grove, PA, USA) for 2 hours at room temperature. The sections were mounted in SlowFade DAPI (Invitrogen). Sections were imaged with an HD AxioImager Zeiss microscope equipped with a CCD digital camera (FIG. 11). Images revealed presence of high lymphocyte numbers in tumor regions that expressed hypoxia marker CAIX indicative of hypoxic state prior to OMX administration suggesting that OMX treatment relieved immunosuppressive microenvironment and allowed lymphocyte infiltration.

Example 8. Correlation of Tumor Volume, Tumor Hypoxia and Reduced T Cell Infiltration 4T1-Luc Tumor Model. 8 week-old female BALB/c mice were purchased from Charles River Labs. Luciferase-expressing 4T1 mouse breast tumor cells (4T1-Fluc-Neo; Imanis Life Sciences) were grown in RPMI medium supplemented with 10% fetal bovine serum, 1× penicillin/streptomycin, and 0.7 mg/ml G-418 (InvivoGen). Cells were trypsinized and resuspended in a 50:50 mixture of medium: Matrigel (Corning), and 2×10$^5$ cells in 100 μl volume was injected subcutaneously into mice. At day 10 and day 14 post-implantation, tumors were measured and volumes calculated (length× width×height×0.523), mice were injected simultaneously with 120 mg/kg pimonidazole i.p. (PIMO, Hypoxyprobe) and 30 mg/kg EF5 i.v. (Hypoxia Imaging Center), sacrificed 90 min post-PIMO/EF5 injection, and tumors were harvested. Harvested tumors were frozen in OCT for immunostaining, as well as dissociated into single cells using a gentleMACS dissociator followed by incubation with 0.75 mg/ml collagenase/dispase (Roche) at 37° C. with shaking for 45 min. Dissociated cells were passed through 70 μm filters.

Flow Cytometry. Unfixed dissociated cells were stained with antibodies for T cells (hamster anti-mouse CD3-AlexaFluor 488, clone 145-2C11, eBioscience; rat anti-mouse CD4-APC, clone RM4-5, BD Biosciences; rat anti-mouse CD8-PE, clone 53-6.7, BD Biosciences), and flow cytometry was performed using a FACSCalibur. Spleens were used as T cell positive controls for gating purposes. Also after filtration of dissociated cells through 70 μm filters, cells were stained with viability dye 570 (BD Biosciences), fixed with formalin and methanol, stained with antibodies for hypoxia markers (rabbit anti-pimonidazole, Hypoxyprobe, followed by donkey anti-rabbit AlexaFluor 647; mouse anti-EF5 conjugated to AlexaFluor 488, Hypoxia Imaging Center), and analyzed on a FACSCalibur. Flow cytometry data were analyzed using FlowJo.

Immunofluorescence Staining. Frozen sections were cut at 10 μm, fixed with 4% PFA, stained with primary antibodies (rat anti-mouse CD4, rat anti-mouse CD8, rabbit anti-PIMO), followed by secondary antibodies (donkey anti-rat AlexaFluor 594, donkey anti-PIMO AlexaFluor 488), and counterstained with DAPI.

As shown in FIGS. 13A-13K, larger tumor size correlates with enhanced hypoxia and reduced lymphocyte infiltration in subcutaneous 4T1-Luc syngeneic tumors. FIG. 12A shows tumor volumes on day 10 and day 14 post-implantation. FIG. 12B shows the fraction of lymphocytes within the viable cell population and FIG. 12C shows the absolute lymphocyte cell numbers within the viable population. Negative correlations between tumor volume and percentage lymphocytes (FIG. 12D) and between percentage hypoxia and percentage lymphocytes (FIG. 12F) were demonstrated whereas the relationship between tumor volume and percentage hypoxia showed a positive correlation (FIG. 12E). Negative correlations were also seen between tumor volume and percentage CD3-positive T cells (FIG. 12G), between tumor volume and percentage CD4-positive T cells (FIG. 12H), between tumor volume and percentage CD8-positive T cells (FIG. 12I), between tumor volume and percentage CD3-CD4-double-positive T cells (FIG. 12J), and between tumor volume and percentage CD3-CD8-double-positive T cells (FIG. 12K).

FIGS. 13A-13F show that hypoxic tumor regions are immunosuppressive and exhibit reduced T cell infiltration in subcutaneous 4T1-Luc syngeneic mouse tumors.

```
SEQUENCES
TT. WT
                                                   (SEQ ID NO: 1)
ATGAAGGGGACAATCGTCGGGACATGGATAAAGACCCTGAGGGACCTTTACGGGA

ATGATGTGGTTGATGAATCTTTAAAAAGTGTGGGTTGGGAACCAGATAGGGTAAT

TACACCTCTGGAGGATATTGATGACGATGAGGTTAGGAGAATTTTTGCTAAGGTG

AGTGAAAAAACTGGTAAAAATGTCAACGAAATATGGAGAGAGGTAGGAAGGCAGA

ACATAAAAACTTTCAGCGAATGGTTTCCCTCCTATTTTGCAGGGAGAAGGCTAGT
```

-continued

```
GAATTTTTTAATGATGATGGATGAGGTACACCTACAGCTTACCAAGATGATAAAA

GGAGCCACTCCTCCAAGGCTTATTGCAAAGCCTGTTGCAAAAGATGCCATTGAAA

TGAGTACGTTTCTAAAAGAAAGATGTACGATTACTTTTTAGGGCTTATAGAGGGT

AGTTCTAAATTTTTCAAGGAAGAAATTTCAGTGGAAGAGGTCGAAAGAGGCGAAA

AAGATGGCTTTTCAAGGCTAALAGTCAGGATAAAATTTATTAAACCCCGTTTTTG

AGTGA
```

(SEQ ID NO: 2)
```
MKGTIVGTWIKTLRDLYGNDVVDESLKSVGWEPDRVITPLEDIDDDEVRRIFAKV

SEKTGKNVNEIWREVGRQNIKTFSEWFPSYFAGRRLVNFLMMMDEVHLQLTKMIK

GATPPRLIAKPVAKDAIEMEYVSKRKMYDRYFLGLIEGSSKFFKEEISVEEVERG

EKDGFSRLKVRIKFKNPVFE
``` foldon domain (SEQ ID NO: 3)
```
GGTTATATTCCTGAAGCTCCAAC4AGATGCAAGCTTACGTTCGTAAAGATGGCGA

ATGGGTATTACTTTCTACCTTTTTA
```

(SEQ. ID NO: 4)
```
GYIPEAPRDGQAYVRKDGEWVLLSTFL
```

L2 WT (SEQ ID NO: 9)
```
ATGATGTCTATGAAAGGAATCATATTCAACGAATTTCTCAATTTTGTAGAAAAAA

GTGAATCCTACACCCTGGTAGATCAAATTATTATGGATAGTCATTTGAAGTCCCA

TGGTGCCTACACGTCTATCGGTACATACTCTGCCAAAGAATTATTTCAATTGGTT

AAAGCGCTTGCTATGAAAAATGGCAAACCAACATCAGTGATTTTACAAGAATATG

GTGAGTATTTGTTTGAGGTTTTTGGAAAAAAATATCCTCAATTTTTCAGGGAAAA

AAAGTCGGTGTTTCAATTTTTGGAAGCGCTTGAAACACATATTCATTTCGAAGTG

AAAAAATTGTATGAGTATACTGAACTACCCCATTTTGAATGCCAATATCACAGTG

AAAATCAAATGGAAATGATTTACACTTCTTCGCGTCCTTTGGCCGATTTTGCGGA

AGGTTTAATAAAAGGTTGTATTAAATATCATAAAGAAAACATGACTATTGTTCGT

GAAAATCTGCCTGCAAAAACAGGCTTTAAGGTAAGATTTGTATTAACAAAAGGCG

ATCCTGATGAGTGA
```

(SEQ ID NO: 10)
```
MMSMKGIIFNEFLNFVEKSESYTLVDQIIMDSHLKSHGAYTSIGTYSPKELFQLVKA

LAMKNGKPTSVILQEYGEYLFEVFAKKYPQFFREKKSVFQFLEALETHIHFEVKKLY

DYTELPHFECQYHSQNQMEMIYTSSRPLADFAEGLIKGCIKYHKENMTIVRENLPAK

TGFKVRFVLTKGDPDE
```

L1 WT (SEQ ID NO: 11)
```
ATGAAAGCTATCGTTTTTACCTCCTTAAATGACATGATTATAGAACAATTTGGC

ATAGAAACCTGGGACCAACTCGTATCCTCACTAGACCCTCCAAGTGGCGGAAGT

TATACAGCAGGCGGCACTTACTGGGATACAGAATTTCAGCAATTGATTAAGGCC

ATTGCGAAGAGGACCAATCAGGACGCTTCTGTTTTTTTAGAGGCCTTTGGTGAA

TACATGTTTCCTATCTTATCGAGTAAGTGCGCAATTTTTTTAAAAAAGGACATG

ACATTAAAAGAATTTTTAAAAAGCATTGATGGAACAATTCATGTGGAAGTAGAA

AAGTTATACCCAGATGAAACATTACCTACCATTAGCTATGAAGAGCCTGCTGCA

AACCAALTTGTTATTGGTATCGATCGCATAGAAGACTCTGTCATTTTGCAATGG
```

```
GGCTECATCCAGGGAGCAGCGCAACATTTTAAAAAGAAAATTACCATTAAGCAG

ACTCACTGCATGTTAAAAAAGATGATCATTGTCGTTTGGAGATTACCTTTGAG

TGA
```

(SEQ ID NO: 12)
```
MKGIVFTSLNDMIIEQFGIETWDQLVSSLDLPSGGSYTAGGTYSDTEFQQLIKAIAKR

TNQHASVFLEAFGEYMFPILSSKCAIFLKKDMTLKEFLKSIDGTIHVEVEKLYPDETL

PTISYEEPAANQLVMVYRSHRRLCHFAMGLIQGAAQHFKKKITIKQTHCMLKKDDHCR

LEITFE
```

*Homo sapiens* WT (1-385)

(SEQ ID NO: 13)
```
ATGTACGGATTTGTGAATCACGCCCTGGAGTTGCTGGTGATCCGCAATTACGGC

CCCGAGGTGTGGGAAGACATCAAAAAAGAGGCACAGTTAGATGAAGAAGGACAG

TTTCTTGTCAGAATAATATATGATGACTCCAAAACTTATGATTTGGTTGCTGCA

AGCAAAGTCCTCAATCTCAATGCTGGAGAAATCCTCCAAATGTTTGGGAAGATG

TTTTTCGTCTTTTGCCAAGAATCTGGTTATGATACAATCTTGCGTGTCCTGGGC

TCTAATGTCAGAGAATTTCTACAGAACCTTGATGCTCTGCACGACCACCTTGCT

ACCATCTACCCAGGAATGCGTGCACCTTCCTTTAGGTGCACTGATGCAGAAAAG

GGCAAAGGACTCATTETGCACTACTACTCAGAGAGAGAAGGACTTCAGGATATT

GTCATTGGAATCATCAAAACAGTGGCACAACAAATCCATGGCACTGAAATAGAC

ATGAAGGTTATTCAGCAAAGAAATGAAGAATGTGATATACTCAATTTTTAATT

GAAGAAAAAGAGTCAAAAGAAGAGGATTTTTATGAAGATCTTGACAGATTTGAA

GAAAATGGTACCCAGGAATCACGCATCAGCCCATATACATTCTGCAAAGCTTTT

CCTTTTCATATAATATTTGACCGGGACCTAGTGGTCACTCAGTGTGGCAATGCT

ATATACAGAGTTCTCCCCCAGCTCCAGCCTGGGAATTGCAGCCTTCTGTCTGTC

TTCTCGCTGGTTCGTCCTCATATTGATATTAGTTTCCATGGGATCCTTTCTCAC

ATCAATACTGTTTTTGTATTGAGAAGCAAGGAAGGATTGTTGGATGTGGAGAAA

TTAGAATGTGAGGATGAACTGACTGGGACTGAGATCAGCTGCTTACGTCTCAAG

GGTCAAATGATCTACTTACCTGAAGCAGATAGCATACTTTTTCTATGTTCACCA

AGTGTCATGAACCTGGACGATTTGACAAGGAGAGGGCTGTATCTAAGTGACATC

CCTCTGCATGATGCCACGCGCGATCTTGTTCCTGAGAACAATTTAGAGAGGAAT

ACAAACTCACCCAAGAACTGGAAATCCTCACTGACAGGCTACAGCTCAGCTTAA

GAGCCCTGGAAGATTGA
```

(SEQ ID NO: 14)
```
MYGFVNHALELLVIRNYGPEVWEDIKKEAQLDEEGQFLVRIIYDDSKTYDLVAAAS

KVLNLNAGEILQMFGKMFFVFCQESGYDTILRVLGSNVREFLQNLDALHDHLATIY

PGMRAPSFRCTDAEKGKGLILHYYSEREGLQDIVIGIIKTVAQQIHGTEIDMKVIQ

QRNEECDHTQFLIEEKESKEEDFYEDLDRFEENGTQESRISPYTFCKAFPFHIIFD

RDLVVTQCGNAIYRVLPQLQPGNCSLLSVFSLVRPHIDISFHGILSHINTVFVLRS

KEGLLDVEKLECEDELTGTEISCLRLKGQMIYLPEADSILFLCSPSVMNLDDLTRR

GLYLSDIPLHDATRDLVLLGEQFREEYKLTQELEILTDRLQLTLRALED
```

*Homo sapiens* β2 (1-217)

(SEC ID NO: 15)
```
ATGTATGGATTCATCAACACCTGCCTGCAGTCTCTTGTGACAGAGAAATTTGGT

GAGGAGACATGGGAGAAGCTGAAGGCTCCTGCAGAAGTGCAAGATGTCTTCATG
```

-continued

```
ACCTACACCGTGTATGATGACATCATCACCATTAAGCTCATCCAAGAAGCCTGC

AAGGTTCTGGATGTGTCCATGGAAGCCATTCTGAAGCTCTTTGGCGAATACTTC

TTTAAGTTCTGTAAGATGTCTGGCTATGACAGGATGCTGCGGACACTTGGAGGA

AATCTCACCGAGTTTATTGAAAACCTAGATGCACTCCACAGTTACCTGGCACTG

TCCTATCAGGAAATGAACGCACCATCCTTTCGAGTGGAGGAAGGAGCTGACGGG

GCCATGCTTCTCCACTACTACTCAGACAGACATGGTCTGTGTCACATTGTACCA

GGTATCATTGAAGCTGTGGCCAAGGACTTCTTTGACACTGATGTGGCCATGAGT

ATCCTGGATATGAACGAAGAGGTGGAAAGGACAGGGAAGAAAGAACATGTTGTG

TTTCTGTTTCGTTTCAGAAGGCTCACAGACAGATAAGAGGAGCAAAGGCAAGCC

GGCCACAAGGCAGTGAGGACAGCCAGGCAGACCAGGAGGCTCTCCAGGGAACAC

TCCTT
```

(SEQ ID NO: 16)
```
MYGFINTCLQSLVTEKFGEEETWEKLKAPAEVQDVFMTYTVYDDIITIKLIQEACK

VLDVSMEAILKLFGEYFFKFCKMSGYDRMLRTLGGNLTEFIENLDALHSYLALSYQ

EMNAPSFRVEEGADGAMLLHYYSDRHGLCHIVPGIIEAVAKDFFDTDVAMSILDMN

EEVERTGKKEHVVFLVVQKAHRQIRGAKASRPQGSEDSQADQEALQGTLL
```

*Rattus norvegicus* β1(1-385)

(SEQ ID NO: 17)
```
ATGTACGGTTTTCTCAACCATGCCCTGGAGCTGCTGGTGATCCGCAATTACGGT

CCCGAGTTGTGGGAAGACATCAAAAAAGAGGCGCAGCTGGATGAAGAAGGCCAG

TTTCTTGTGAGAATAATCTACGATGATTCCAAAACCTATGACTTGGTGGCTGCT

GCGAGCAAAGTCCTCAACCTCAATGCTGGTGAAATCCTGCAGATGTTTGGGAAG

ATGTTTTTCGTCTTCTGTCAAGAGTCTGGCTATGATACCATCTTGCGTGTCCTC

GCCACCATATACCCAGGGATGCGCGCACCTTCCTTCCGGTGCACCGATGCAGAA

AAAGGCAAAGGGCTCATTCTGCACTACTACTCGGAAAGAGAGGGGCTTCAGGAC

ATTGTGATCGGGATTATCAAGACTGTAGCTCAACAGATCCATGGCACTGAGATA

GACATGAAGGTTATTCAGCAAAGAAGTGAAGAATGTGATCATACCCAATTTTTA

ATTGAAGAAAAGAATCAAAAGAAGAGGATTTTTATGAAGATCTGGACAGGTTT

GAAGAGAACGGTACCCAGGACTCCCGTATCAGCCCGTACACCTTCTGCAAAGCG

TTTCCTTTTCACATCATATTTGACCGGGACCTAGTAGTCACGCAGTGTGGAAAT

GCTATCTACAGAGTGCTCCCCCAGCTCCAGCCTGGGAAGTGCAGCCTTCTGTCT

GTCTTCTCTCTGGTCCGCCCTCATATTGACATCAGTTTCCACGGGATTCTTTCA

CACATCAATACCGTCTTTGTACTGAGAAGCAAGGAAGGGTTGCTGGATGTTGAG

AAACTTGAATGTGAGGATGAACTGACTGGGGCAGAGATTAGCTGCCTCCGTCTC

AAAGGCCAAATGATCTATTTACCGGAAGCAGATAGCATCCTCTTCCTCTGTTCA

CCAAGTGTGATGAACTTGGATGACCTAACAAGAAGAGGCCTGTACCTGAGTGAC

ATCCCTCTCCATGATGCTACACGAGACCTGGTCCTTTTGGGAGAACAGTTCCGG

GAGGAGTACAAACTGACACAAGAGCTGGAAATCCCTCACAGACAGGCTGCAGCT

CACACTGAGGGCTTTGGAGGATTGA
```

(SEQ ID NO: 18)
```
MYGFVNHALELLVIRNYGPEVWEDIKKEAQLDEEGQFLVRIIYDDSKTYDLVAAAS

KVLNLNAGEILQMFGKMFFVFCQESGYDTILRVLGSNVREFLQNLDALHDHLATIY
```

-continued

PGMRAPSFRCTDAEKGKLILHYYSEREGLQDIVIGIIKTVAQQIHGTEIDMKVIQQ

RSEECDHTQFLIEEKESKEEDFYEDLDRFEENGTQDSRISPYTFCKAFPFHIIFDR

DLVVTQCGNAIYRVLPQLQPKCSLLSVSFLVRPHIDISFHGILSHINTVFVFRSKE

GLLDVEKLECEDELTGAEISCLRLKGQMIYLPEADSILFLCSPSVMNLDDLTRRGL

YLSDIPLHDATRDLVLLGEQFREEYKLTQELEILTDRLQLTLRALED

*Rattus norvegicus* β1(1-385)

(SEQ ID NO: 19)

ATGTACGGTTTTGTGAACCATGCCCTGGAGCTGCTGGTGATCCGCAATTACGGT

CCCGAGGTGTGGGAAGACATCAAAAAGAGGCGCAGCTGGATGAAGAAGGCCAG

TTTCTTGTGAGAATAATCTACGATGATTCCAAAACCTATGACTTGGTGGCTGCT

GCGAGCAAAGTCCTCAACTCAATGCTGGTGAAATCCTGCAGATGTTTGGGAGAG

TGTTTTTCGTCTTCTGTCAAGAGTCTGGCTATGATACCATCTTGCGTGTCCTGG

GATCTAATGTCAGGGAGTTTTTGCAGAACCTCGACGCCCTGCACGACCACCTCG

CCACCATCTACCCAGGGATGCGCGCACCTTCCTTCCGGTGCACCGATGCAGAAA

AAGGCAAAGGGCTCATTCTGCACTACTACTCGGAAAGAGAGGGGCTTCAGGACA

TTGTGATCGGGATTATCAAGACTGTAGCTCAACAGATCCATGGCACTGAGATAG

ACATGAAGGTTATTCAGCAAAGAAGTGAAGAATGTGATCATACCCAATTTTTAA

TTGAAAAAAGAATCAAAAGAAGAGGATTTTTATGAAGATCTGGACAGGTTTGA

AGAGAACGGTACCCAGGACTCCCGTATCAGCCCGTACACCTTCTGCAAAGCGTT

TCCTTTTCACATCATATTTGACCGGGACCTAGTAGTCACGCAGTGTGGAAATGC

TATCTACAGAGTGCTCCCCCAGCTCCAGCCTGGGAAGTGCAGCCTTCTGTCTGT

CTTCTCTCTGGTCCGCCCTCATATTGACATCAGTTTCCACGGGATTCTTTCACA

CATCAATACCGTCTTTGTACTGAGAAGCAAGGAAGGGTTGCTGGATGTTGAGAA

ACTTGAATGTGAGGATGAACTGACTGGGGCAGAGATTAGCTGCCTCCGTCTCAA

AGGCCAAATGATCTATTTACCGGAAGCAGATAGCATCCTCTTCCTCTGTTCACC

AAGTGTGATGACTTGGATGACCTAACAAGAAGAGGCCTGTACCTGAGTGACATC

CCTCTCCATGATGCTACACGAGACCTGGTCCTTTTGGGAGAACAGTTCCGGGAG

GAGTACAAACTGACACAAGAGCTGGAAATCCTCACAGACAGGCTGCAGCTCACA

CTGAGGGCTTTGGAGGATTGA (SEQ ID NO: 20)

MYGFVNHALELLVIRNYGPEVWEDIKKEAQLDEEGQFLVRIIYDDSKTYDLVAAAS

KVLNLNAGEILQMFGKMFFVFCQESGYDTILRVLGSNVREFLQNLDALHDHLATIY

PGMRAPSFRCTDAEKGKGLILHYYSEREGLQDIVIGIIKTVAQQIHGTEIDMKVIQ

QRSEECDHTQFLIEEKESKEEDFYEDLDRFEENGTQDSRISPYTFCKAFPFHIIFD

RDLVVTQCGNAIYRVLPQLQPGKCSLLSVFSLVRPHIDISFHGILSHINTVFVLRS

KEGLLDVEKLECEDELTGAEISCLRLKGQMIYLPEADSILFLCSPSVMNLDDLTRR

GLYLSDIPLHDATRDLVLLGEDQFREEYKLTQELEILTDRLQLTLRALED

*Rattus norvegicus* β2

(SEQ ID NO: 21)

ATGTATGGATTGATCAACACCTGCCTGCAGTCTCTTGTGACAGAGAAATTTGGT

GAGGAGACATGGGAGAAGCTGAAGGCTCCTGCAGAAGTGCAAGATGTCTTCATG

ACCTACACCGTGTATGATGACATCATCACCATTAAGCTCATCCAAGAAGCCTGC

AAGCTTCTCGATGTGTCCATGGAAGCCATTTCTGAAGCTCTTTGGCGAATACTT

```
CTTTAAGTTCTGTAAGATGTCTGGCTATGACAGGATGCTGCGGACACTTGGAGG

AAATCTCACCGAGTTTATTGAAAACCTAGATCCACTCCACAGTTACCTGCCACT

CTCCTATCAGGAAATGAACGCACCATCCTTTCGAGTGGAGGAAGGAGCTGACGG

GGCGATGCTTCTCCACTACTACTCAGACAGACATGGTCTGTGTCACATTGTACC

AGGTATCATTGAAGCTGTGGCCAAGGACTTCTTTGACACTGATGTCGCCATGAG

TATCCTGGATATGAACGAAGAGGTGGAAAGGACAGGGAAGAAGAACATGTTGTG

TTTCTGGTCGTGCAGAAGGCTCACAGACAGATAAGAGGAGCAAAGGCAAGCCGG

CCACAAGGCAGTGAGGACAGCCAGGCAGACCAGGAGGCTCTCCAGGGAACACTC

CTTCGGATGAAGGAGAGATATTTAAACATCCCTGTTTGCCCTGGGGAGAAATCT

CACTCAACTGCTGTGAGGGCATCGGTCCTTTTTGGAAAAGGGCCCCTCAGGGAC

ACCTTCCAGCCCGTCTATCCTGAGAGACTATGGGTCGAAGAGGAGGTGTTCTGT

GATGCTTTTCCTTTCCACATTGTCTTTGATGAAGCACTAAGGGTCAAGCAAGCT

GGAGTGAATATTCAGAAGTATGTCCCTGGAATCTTAACCCAGAAGTTTGCACTA

GATGAGTATTTTTCCATCATCCACCCTCAAGTTACTTTCAACATCTCCAGCATC

TGCAAGTTCATTAACAGTCAGTTTGTCTTGAAGACAAGAAAAGAAATGATGCCC

AAAGCAAGGAAGAGCCAGCCGATGCTCAAACTCCGGGGTCAGATGATCTGGATG

GAGTCTCTGAGGTGCATGATCTTCATGTGTGTTCCCCAAACGTCCGCAGCCTGC

AAGAGCTGGAAGAGAGCAAGATGCATCTTTCTGATATCGCTCCGCACGACACGA

CCAGGGATCTCATCCTCCTCAACCAGCAGAGGCTGGCAGAGATGGAGCTGTCCT

GCCAACTGGAAAAGAAGAAGGAGGAGTTGCGTGTCCTTTCCAATCACCTGGCCA

TCGAGAAGAAGAAGACAGAGACCTTGCTGTATGCCATGCTCCCTGAACATGTGC

CCAACCAACTCAAGGAGGCCAGAAAGGTGGCTCCAGGAGAATTTGAAACATCTA

CAATCCTTTTCAGCGATGTTGTGACATTTACCAACATCTGTGCAGCCTGTGAAC

CTATCCAAATCGTGAACATGCTGAATTCAATGTACTCCAAGTTTGACAGGTTAA

CCAGTGTCCATGATGTCTACAAAGTAGAAACAATAGCGGATGCTTACATGGTGG

TGCGTGGAGTACCAGTACCCCTTGAAAGCCATGCTCAAAGAGTCGCCAATTTTG

CTCTGGGATGAGAATTTCTGCAAAAGAAGTGATGAATCCTGTCACTGGGGAAC

CTATCCAGATCAGAGTGGGAATCCACACTGGACCAGTCTTAGCAGGTGTTGTGG

GAGACAAGATGCCTCGGTACTGCTTGTTTGGTGACACTGTAAACACAGCCTCTA

GGATGGAAAGTCACGGGCTTCCCAGCAAAGTGCATCTGAGCCCCACAGCCCACA

GAGCCCTGAAAAACAAAGGGTTTGAAATTGTCAGGAGAGGCGAGATCGAAGTGA

AGGGGAAAGGAAAGATGACCACATACTTTCTGATCCAGAACCTGAATGCCACCG

AGGATGAGATAATGGGGCGACCTTCAGCCCCCCGCTGATGGGAAGGAAGTATGT

ACTCCCGGAAACCAAGTCAGGAAGTCCCCTGCTGTCCCGAGGAACACAGACCAT

CAGCAACAAGTCTACAAAGGAGACCCAGCAGACGCTTCTAATGAAGTCACACTT

GCTGGGAGCCCAGTGGCAGGGCGAAACTCCACAGATGCAGTCAATAACCAGCCA

TCACCAGATGAGACCAAGACAAGTGTCGTTGCTAGTGGCCCTGTGCTGTCTGCT

TTCTGTGTTGTGCTGTGA
```

(SEQ ID NO: 22)
MYGFINTCLQSLVTEKFGEETWEKLKAPAEVQDVFMTYTVYDDIITIKLIQEACKV

LDVSMEAILKLFGEYFFKFCKMSGYDRMLRTLGGNLTEFIENLDALHSYLALSYQE

-continued

MNAPSFRVEEGADGAMLLHYYSDRHGLCHIVPGIIEAVAKDFFDTDVAMSILDMNE

EVERTGKKEHVVFLVVQKAHRQIRGAKASRPQGSEDSQADQEALQGTLLRMKERYL

NIPVCPGEKSHSTAVRASVLFGKGPLRDTFQPVYPERLWVEEEVFCDAFPFHIVFD

EALRVKQAGVNIQKYVPGILTQKFALDEYFSIIHPQVTFNISSICKFINSQFVLKT

RKEMMPKARKSQPMLKLRGQMIWMESLRCMIFMCSPNVRSLQELEESKMHLSDIAP

HDTTRDLILLNQQRLAEMELSCQLEKKKEELRVLSNHLAIEKKKTETLLYAMLPEH

VANQLKEGRKVAAGEFETCTILFSDVVTFTNICAACEPIQIVNMLNSMYSKFDRLT

SVHDVYKVETIGDAYMVVGGVPVPVESHAQRVANFALGMRISAKEVMNPVTGEPIQ

IRVGIHTGPVLAGVVGDKMPRYCLFGDTVNTASRMESHGLPSKVHLSPTAHRALKN

KGFEIVRRGEIEVKGKGKMTTYFLIQNLNATEDIMGRPSAPADGKEVCTPGNQVRK

SPAVPRNTDHQQQVYKGDPADASNEVTLAGSPVAGRNSTDAVNNQPSPDETKTSVV

ASGPVLSAFCVVL

---

What is claimed is:

1. A method for treating cancer in a human individual having cancer comprising: (a) administering to the individual an effective amount of a trimeric H-NOX protein, wherein the trimeric H-NOX protein comprises three monomers, wherein the monomers each comprise a *T tengcongensis* H-NOX domain and a trimerization domain, wherein each of the three monomers is covalently bound to polyethylene glycol (PEG), wherein each *T tengcongensis* H-NOX domain has the amino acid sequence of SEQ ID NO:2 except for a L144F amino acid substitution in SEQ ID NO:2, and wherein the trimerization domain is a foldon domain of bacteriophage T4 fibritin; and (b) administering to the individual an immunotherapy, wherein the immunotherapy is an anti-PD-1 antibody therapy, or a dual PD-1/PD-L1 blockade antibody therapy; and wherein the cancer is glioblastoma.

2. The method of claim 1, wherein the C-terminus of the H-NOX domain is covalently linked to the trimerization domain.

3. The method of claim 1, wherein the H-NOX domain in each of the three monomers is linked via an amino acid linker to the foldon domain of T4 bacteriophage fibritin, wherein the amino acid linker is three, four, five, six, seven, eight, nine, or ten amino acids in length.

4. The method of claim 3, wherein the amino acid linker consists of Gly-Ser-Gly.

5. The method of claim 1, wherein each of the three monomers comprises three PEG molecules per monomer, wherein the molecular weight of each of the three PEG molecules is between 1 kDa and 10 kDa.

6. The method of claim 1, wherein each of the three monomers comprises the amino acid sequence of SEQ ID NO:8.

7. The method of claim 5, wherein each of the three monomers comprises the amino acid sequence of SEQ ID NO:8.

8. The method of claim 1, wherein the administering of the trimeric H-NOX protein is intravenous.

9. The method of claim 1, wherein the administering of the trimeric H-NOX protein is by a bolus and/or by infusion.

10. The method of claim 1, wherein the administering of the trimeric H-NOX protein is before or concurrently, wherein concurrently occurs with a time separation of no more than 60 minutes, with the administering of the immunotherapy.

11. The method of claim 1, further comprising administering a radiation therapy or chemotherapy to the individual.

12. The method of claim 1, wherein the immunotherapy is an anti-PD-1 antibody.

13. The method of claim 1, wherein the trimeric H-NOX protein is not encapsulated.

14. The method of claim 2, wherein the trimeric H-NOX protein is not encapsulated.

15. The method of claim 3, wherein the trimeric H-NOX protein is not encapsulated.

16. The method of claim 5, wherein the trimeric H-NOX protein is not encapsulated.

17. The method of claim 6, wherein the trimeric H-NOX protein is not encapsulated.

18. The method of claim 1, wherein the foldon domain comprises the amino acid sequence of SEQ ID NO:4.

* * * * *

SEQUENCE LISTING

<160> NUMBER OF SEQ ID NOS: 30

<210> SEQ ID NO 1
<211> LENGTH: 555
<212> TYPE: DNA
<213> ORGANISM: Thermoanaerobacter tengcongensis

<400> SEQUENCE: 1

```
atgaagggga caatcgtcgg gacatggata aagaccctga gggacctta cgggaatgat      60
gtggttgatg aatctttaaa aagtgtgggt tgggaaccag atagggtaat tacacctctg     120
gaggatattg atgacgatga ggttaggaga attttttgcta aggtgagtga aaaaactggt    180
aaaaatgtca acgaaatatg gagagaggta ggaaggcaga acataaaaac tttcagcgaa    240
tggtttccct cctatttttgc agggagaagg ctagtgaatt ttttaatgat gatggatgag    300
gtacacctac agcttaccaa gatgataaaa ggagccactc ctccaaggct tattgcaaag    360
cctgttgcaa aagatgccat tgaaatggag tacgtttcta aaagaaagat gtacgattac    420
ttttagggc ttatagaggg tagttctaaa tttttcaagg aagaaatttc agtggaagag    480
gtcgaaagag cgaaaaaga tggctttttca aggctaaaag tcaggataaa atttaaaaac    540
cccgtttttg agtga                                                     555
```

<210> SEQ ID NO 2
<211> LENGTH: 184
<212> TYPE: PRT
<213> ORGANISM: Thermoanaerobacter tengcongensis

<400> SEQUENCE: 2

```
Met Lys Gly Thr Ile Val Gly Thr Trp Ile Lys Thr Leu Arg Asp Leu
1               5                   10                  15

Tyr Gly Asn Asp Val Val Asp Glu Ser Leu Lys Ser Val Gly Trp Glu
                20                  25                  30

Pro Asp Arg Val Ile Thr Pro Leu Glu Asp Ile Asp Asp Asp Glu Val
            35                  40                  45

Arg Arg Ile Phe Ala Lys Val Ser Glu Lys Thr Gly Lys Asn Val Asn
        50                  55                  60

Glu Ile Trp Arg Glu Val Gly Arg Gln Asn Ile Lys Thr Phe Ser Glu
```

```
                65                  70                  75                  80
Trp Phe Pro Ser Tyr Phe Ala Gly Arg Arg Leu Val Asn Phe Leu Met
                    85                  90                  95

Met Met Asp Glu Val His Leu Gln Leu Thr Lys Met Ile Lys Gly Ala
                100                 105                 110

Thr Pro Pro Arg Leu Ile Ala Lys Pro Val Ala Lys Asp Ala Ile Glu
                115                 120                 125

Met Glu Tyr Val Ser Lys Arg Lys Met Tyr Asp Tyr Phe Leu Gly Leu
            130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180

<210> SEQ ID NO 3
<211> LENGTH: 81
<212> TYPE: DNA
<213> ORGANISM: Thermoanaerobacter tengcongensis

<400> SEQUENCE: 3
ggttatattc ctgaagctcc aagagatggg caagcttacg ttcgtaaaga tggcgaatgg      60
gtattacttt ctacctttt a                                                 81

<210> SEQ ID NO 4
<211> LENGTH: 27
<212> TYPE: PRT
<213> ORGANISM: Thermoanaerobacter tengcongensis

<400> SEQUENCE: 4

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 5
<211> LENGTH: 690
<212> TYPE: DNA
<213> ORGANISM: Thermoanaerobacter tengcongensis

<400> SEQUENCE: 5
atgaagggga caatcgtcgg acatggata aagaccctga gggacctta cgggaatgat       60 gtggttgatg aatctttaaa aagtgtgggt tgggaaccag atagggtaat tacacctctg     120
gaggatattg atgacgatga ggttaggaga atttttgcta aggtgagtga aaaaactggt     180
aaaaatgtca cgaaatatg gagagaggta ggaaggcaga acataaaaac tttcagcgaa     240
tggtttccct cctatttgc agggagaagg ctagtgaatt ttttaatgat gatggatgag     300
gtacacctac agcttaccaa gatgataaaa ggagccactc ctccaaggct tattgcaaag    360
cctgttgcaa agatgccat tgaaatggag tacgttttcta aagaaagat gtacgattac     420 ttttaggggt ttatagaggg tagttctaaa ttttcaagg aagaaatttc agtggaagag     480
gtcgaaagag gcgaaaaaga tggcttttca aggctaaaag tcaggataaa atttaaaaac    540 cccgttttg agtataagaa aaatctcgag gcagcggcg ttatattcc tgaagctcca      600 agagatgggc aggcttacgt tcgtaaagat ggcgaatggg tattactttc tacctttta    660
``` agggtagtc accatcacca tcaccattga 690

<210> SEQ ID NO 6
<211> LENGTH: 225
<212> TYPE: PRT
<213> ORGANISM: Thermoanaerobacter tengcongensis

<400> SEQUENCE: 6

```
Met Lys Gly Thr Ile Val Gly Thr Trp Ile Lys Thr Leu Arg Asp Leu
1               5                   10                  15
Tyr Gly Asn Asp Val Val Asp Glu Ser Leu Lys Ser Val Gly Trp Glu
            20                  25                  30
Pro Asp Arg Val Ile Thr Pro Leu Glu Asp Ile Asp Asp Glu Val
        35                  40                  45
Arg Arg Ile Phe Ala Lys Val Ser Glu Lys Thr Gly Lys Asn Val Asn
    50                  55                  60
Glu Ile Trp Arg Glu Val Gly Arg Gln Asn Ile Lys Thr Phe Ser Glu
65                  70                  75                  80
Trp Phe Pro Ser Tyr Phe Ala Gly Arg Arg Leu Val Asn Phe Leu Met
                85                  90                  95
Met Met Asp Glu Val His Leu Gln Leu Thr Lys Met Ile Lys Gly Ala
            100                 105                 110
Thr Pro Pro Arg Leu Ile Ala Lys Pro Val Ala Lys Asp Ala Ile Glu
        115                 120                 125
Met Glu Tyr Val Ser Lys Arg Lys Met Tyr Asp Tyr Phe Leu Gly Phe
    130                 135                 140
Ile Glu Gly Lys Phe Phe Lys Glu Glu Ile Glu Val Glu Arg Gly
145                 150                 155                 160
Glu Lys Asp Gly Phe Ser Arg Leu Lys Val Arg Ile Lys Phe Lys Asn
                165                 170                 175
Pro Val Phe Glu Tyr Lys Lys Asn Leu Glu Gly Ser Gly Tyr Ile
            180                 185                 190
Pro Glu Ala Pro Arg Asp Gly Gln Ala Tyr Val Arg Lys Asp Gly Glu
        195                 200                 205
Trp Val Leu Leu Ser Thr Phe Leu Arg Gly Ser His His His His
    210                 215                 220
His
225
```

<210> SEQ ID NO 7
<211> LENGTH: 663
<212> TYPE: DNA
<213> ORGANISM: Thermoanaerobacter tengcongensis

<400> SEQUENCE: 7 atgaaggga caatcgtcgg gacatggata aagaccctga gggacctta cgggaatgat 60 gtggttgatg aatcttaaa aagtgtggg tgggaaccag ataggtaat tacacctctg 120 gaggatattg atgacgatga ggttaggaga attttgcta aggtgagtga aaaaactggt 180
aaaaatgtca acgaaatatg gagagaggta ggaaggcaga acataaaaac tttcagcgaa 240
tggtttccct cctatttgc agggagaagg ctagtgaatt ttttaatgat gatggatgag 300
gtacacctac agcttaccaa gatgataaaa ggagccactc ctccaaggct tattgcaaag 360
cctgttgcaa aagatgccat tgaaatggag tacgttctta aaagaagat gtacgattac 420 ttttagggt ttatagaggg tagttctaaa tttttcaagg aagaaatttc agtggaagag 480

-continued

```
gtcgaaagag gcgaaaaaga tggcttttca aggctaaaag tcaggataaa atttaaaaac    540
cccgtttttg agtataagaa aaatctcgag ggcagcggcg gttatattcc tgaagctcca    600
agagatgggc aggcttacgt tcgtaaagat ggcgaatggg tattactttc tacctttttta    660 tga                                                                  663
```

<210> SEQ ID NO 8
<211> LENGTH: 220
<212> TYPE: PRT
<213> ORGANISM: Thermoanaerobacter tengcongensis

<400> SEQUENCE: 8

```
Met Lys Gly Thr Ile Val Gly Thr Trp Ile Lys Thr Leu Arg Asp Leu
1               5                   10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Phe
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu Gly Ser
            180                 185                 190

Gly Gly Tyr Ile Pro Glu Ala Pro Arg Asp Gly Gln Ala Tyr Val Arg
        195                 200                 205

Lys Asp Gly Glu Trp Val Leu Leu Ser Thr Phe Leu
    210                 215                 220
```

<210> SEQ ID NO 9
<211> LENGTH: 564
<212> TYPE: DNA
<213> ORGANISM: Legionella pneumophila

<400> SEQUENCE: 9

```
atgatgtcta tgaaaggaat catattcaac gaatttctca attttgtaga aaaaagtgaa     60
tcctacaccc tggtagatca aattattatg gatagtcatt tgaagtccca tggtgcctac    120
acgtctatcg gtacatactc tcccaaagaa ttatttcaat tggttaaagc gcttgctatg    180
aaaaatggca aaccaacatc agtgatttta caagaatatg gtgagtattt gtttgaggtt    240
tttgcaaaaa aatatcctca atttttcagg gaaaaaaagt cggtgtttca atttttggaa    300
gcgcttgaaa cacatattca tttcgaagtg aaaaaattgt atgactatac tgaactaccc    360
cattttgaat gccaatatca cagtcaaaat caaatggaaa tgatttacac ttcttcgcgt    420
```

```
cctttggccg attttgcgga aggtttaata aaaggttgta ttaaatatca taaagaaaac    480
atgactattg ttcgtgaaaa tctgcctgca aaaacaggct ttaaggtaag atttgtatta    540
acaaaaggcg atcctgatga gtga                                           564
```

<210> SEQ ID NO 10
<211> LENGTH: 187
<212> TYPE: PRT
<213> ORGANISM: Legionella pneumophila

<400> SEQUENCE: 10

```
Met Met Ser Met Lys Gly Ile Ile Phe Asn Glu Phe Leu Asn Phe Val
1               5                   10                  15

Glu Lys Ser Glu Ser Tyr Thr Leu Val Asp Gln Ile Ile Met Asp Ser
            20                  25                  30

His Leu Lys Ser His Gly Ala Tyr Thr Ser Ile Gly Thr Tyr Ser Pro
        35                  40                  45

Lys Glu Leu Phe Gln Leu Val Lys Ala Leu Ala Met Lys Asn Gly Lys
    50                  55                  60

Pro Thr Ser Val Ile Leu Gln Glu Tyr Gly Glu Tyr Leu Phe Glu Val
65                  70                  75                  80

Phe Ala Lys Lys Tyr Pro Gln Phe Phe Arg Glu Lys Lys Ser Val Phe
                85                  90                  95

Gln Phe Leu Glu Ala Leu Glu Thr His Ile His Phe Glu Val Lys Lys
            100                 105                 110

Leu Tyr Asp Tyr Thr Glu Leu Pro His Phe Glu Cys Gln Tyr His Ser
        115                 120                 125

Gln Asn Gln Met Glu Met Ile Tyr Thr Ser Ser Arg Pro Leu Ala Asp
    130                 135                 140

Phe Ala Glu Gly Leu Ile Lys Gly Cys Ile Lys Tyr His Lys Glu Asn
145                 150                 155                 160

Met Thr Ile Val Arg Glu Asn Leu Pro Ala Lys Thr Gly Phe Lys Val
                165                 170                 175

Arg Phe Val Leu Thr Lys Gly Asp Pro Asp Glu
            180                 185
```

<210> SEQ ID NO 11
<211> LENGTH: 543
<212> TYPE: DNA
<213> ORGANISM: Legionella pneumophila

<400> SEQUENCE: 11

```
atgaaaggta tcgttttttac ctccttaaat gacatgatta taaacaatt tggcatagaa    60 acctgggacc aactcgtatc ctcactagac cttccaagtg gtggaagtta tacagcaggc    120
ggcacttact cggatacaga atttcagcaa ttgattaagg ccattgcgaa gaggaccaat    180
cagcacgctt ctgttttttt agaggccttt ggtgaataca tgtttcctat cttatcgagt    240
aagtgcgcaa ttttttttaaa aaaggacatg acattaaaag aattttttaaa aagcattgat    300 ggaacaattc atgtggaagt agaaaagtta tacccagatg aaacattacc taccattagc    360
tatgaagagc ctgctgcaaa ccaattggtt atggtgtatc gatcgcatag aagactctgt    420
cattttgcaa tggggctcat ccagggagca gcgcaacatt ttaaaagaa aattaccatt    480 aagcagactc actgcatgtt aaaaaaagat gatcattgtc gtttggagat tacctttgag    540
tga                                                                  543
```

<210> SEQ ID NO 12
<211> LENGTH: 180
<212> TYPE: PRT
<213> ORGANISM: Legionella pneumophila

<400> SEQUENCE: 12

```
Met Lys Gly Ile Val Phe Thr Ser Leu Asn Asp Met Ile Ile Glu Gln
1               5                   10                  15

Phe Gly Ile Glu Thr Trp Asp Gln Leu Val Ser Ser Leu Asp Leu Pro
            20                  25                  30

Ser Gly Gly Ser Tyr Thr Ala Gly Gly Thr Tyr Ser Asp Thr Glu Phe
        35                  40                  45

Gln Gln Leu Ile Lys Ala Ile Ala Lys Arg Thr Asn Gln His Ala Ser
    50                  55                  60

Val Phe Leu Glu Ala Phe Gly Glu Tyr Met Phe Pro Ile Leu Ser Ser
65                  70                  75                  80

Lys Cys Ala Ile Phe Leu Lys Lys Asp Met Thr Leu Lys Glu Phe Leu
                85                  90                  95

Lys Ser Ile Asp Gly Thr Ile His Val Glu Val Glu Lys Leu Tyr Pro
            100                 105                 110

Asp Glu Thr Leu Pro Thr Ile Ser Tyr Glu Glu Pro Ala Ala Asn Gln
        115                 120                 125

Leu Val Met Val Tyr Arg Ser His Arg Arg Leu Cys His Phe Ala Met
    130                 135                 140

Gly Leu Ile Gln Gly Ala Ala Gln His Phe Lys Lys Lys Ile Thr Ile
145                 150                 155                 160

Lys Gln Thr His Cys Met Leu Lys Lys Asp Asp His Cys Arg Leu Glu
                165                 170                 175

Ile Thr Phe Glu
            180
```

<210> SEQ ID NO 13
<211> LENGTH: 1158
<212> TYPE: DNA
<213> ORGANISM: Homo sapiens

<400> SEQUENCE: 13

```
atgtacggat ttgtgaatca cgccctggag ttgctggtga tccgcaatta cggccccgag     60
gtgtgggaag acatcaaaaa agaggcacag ttagatgaag aaggacagtt tcttgtcaga    120
ataatatatg atgactccaa aacttatgat ttggttgctg ctgcaagcaa agtcctcaat    180
ctcaatgctg gagaaatcct ccaaatgttt gggaagatgt tttcgtcttt ttgccaagaa    240
tctggttatg atacaatctt gcgtgtcctg ggctctaatg tcagagaatt tctacagaac    300
cttgatgctc tgcacgacca ccttgctacc atctacccag gaatgcgtgc accttccttt    360
aggtgcactg atgcagaaaa gggcaaagga ctcattttgc actactactc agagagagaa    420
ggacttcagg atattgtcat tggaatcatc aaaacagtgg cacaacaaat ccatggcact    480
gaaatagaca tgaaggttat tcagcaaaga aatgaagaat gtgatcatac tcaattttta    540
attgaagaaa aagagtcaaa agaagaggat ttttatgaag atcttgacag atttgaagaa    600
aatggtaccc aggaatcacg catcagccca tatacattct gcaaagcttt tccttttcat    660
ataatatttg accgggacct agtggtcact cagtgtggca atgctatata cagagttctc    720 cccagctcc agcctgggaa ttgcagcctt ctgtctgtct tctcgctggt tcgtcctcat    780
attgatatta gtttccatgg gatcctttct cacatcaata ctgtttttgt attgagaagc    840
```

```
aaggaaggat tgttggatgt ggagaaatta gaatgtgagg atgaactgac tgggactgag      900
atcagctgct tacgtctcaa gggtcaaatg atctacttac ctgaagcaga tagcatactt      960
tttctatgtt caccaagtgt catgaacctg gacgatttga caaggagagg gctgtatcta     1020
agtgacatcc ctctgcatga tgccacgcgc gatcttgttc ttttgggaga acaatttaga     1080
gaggaataca aactcaccca gaactggaa atcctcactg acaggctaca gctcacgtta      1140
agagccctgg aagattga                                                   1158

<210> SEQ ID NO 14
<211> LENGTH: 385
<212> TYPE: PRT
<213> ORGANISM: Homo sapiens

<400> SEQUENCE: 14

Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
```

```
                305                 310                 315                 320
Phe Leu Cys Ser Pro Ser Val Met Asn Leu Asp Asp Leu Thr Arg Arg
                    325                 330                 335

Gly Leu Tyr Leu Ser Asp Ile Pro Leu His Asp Ala Thr Arg Asp Leu
                340                 345                 350

Val Leu Leu Gly Glu Gln Phe Arg Glu Glu Tyr Lys Leu Thr Gln Glu
            355                 360                 365

Leu Glu Ile Leu Thr Asp Arg Leu Gln Leu Thr Leu Arg Ala Leu Glu
        370                 375                 380

Asp
385

<210> SEQ ID NO 15
<211> LENGTH: 651
<212> TYPE: DNA
<213> ORGANISM: Homo sapiens

<400> SEQUENCE: 15
atgtatggat tcatcaacac ctgcctgcag tctcttgtga cagagaaatt tggtgaggag     60
acatgggaga agctgaaggc tcctgcagaa gtgcaagatg tcttcatgac ctacaccgtg    120
tatgatgaca tcatcaccat taagctcatc caagaagcct gcaaggttct ggatgtgtcc    180
atggaagcca ttctgaagct ctttggcgaa tacttcttta gttctgtaa gatgtctggc    240 tatgacagga tgctgcggac acttggagga aatctcaccg agtttattga aaacctagat    300
gcactccaca gttacctggc actgtcctat caggaaatga acgcaccatc ctttcgagtg    360
gaggaaggag ctgacggggc gatgcttctc cactactact cagacagaca tggtctgtgt    420
cacattgtac caggtatcat tgaagctgtg ccaaggact tctttgacac tgatgtggcc    480
atgagtatcc tggatatgaa cgaagaggtg gaaaggacag ggaagaaaga acatgttgtg    540
tttctggtcg tgcagaaggc tcacagacag ataagaggag caaaggcaag ccggccacaa    600
ggcagtgagg acagccaggc agaccaggag gctctccagg gaacactcct t            651

<210> SEQ ID NO 16
<211> LENGTH: 217
<212> TYPE: PRT
<213> ORGANISM: Homo sapiens

<400> SEQUENCE: 16

Met Tyr Gly Phe Ile Asn Thr Cys Leu Gln Ser Leu Val Thr Glu Lys
1               5                   10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125
```

```
Leu Leu His Tyr Tyr Ser Asp Arg His Gly Leu Cys His Ile Val Pro
    130                 135                 140
Gly Ile Ile Glu Ala Val Ala Lys Asp Phe Phe Asp Thr Asp Val Ala
145                 150                 155                 160
Met Ser Ile Leu Asp Met Asn Glu Val Glu Arg Thr Gly Lys Lys
                165                 170                 175
Glu His Val Val Phe Leu Val Val Gln Lys Ala His Arg Gln Ile Arg
                180                 185                 190
Gly Ala Lys Ala Ser Arg Pro Gln Gly Ser Glu Asp Ser Gln Ala Asp
                195                 200                 205
Gln Glu Ala Leu Gln Gly Thr Leu Leu
    210                 215

<210> SEQ ID NO 17
<211> LENGTH: 1158
<212> TYPE: DNA
<213> ORGANISM: Rattus norvegicus

<400> SEQUENCE: 17
atgtacggtt ttgtgaacca tgccctggag ctgctggtga tccgcaatta cggtcccgag    60
gtgtgggaag acatcaaaaa agaggcgcag ctggatgaag aaggccagtt tcttgtgaga   120
ataatctacg atgattccaa aacctatgac ttggtggctg ctgcgagcaa agtcctcaac   180
ctcaatgctg tgaaatcct gcagatgttt gggaagatgt ttttcgtctt ctgtcaagag   240
tctggctatg ataccatctt gcgtgtcctg ggatctaatg tcagggagtt tttgcagaac   300
ctcgacgccc tgcacgacca cctcgccacc atctacccag ggatgcgcgc accttccttc   360
cggtgcaccg atgcagaaaa aggcaaaggg ctcattctgc actactactc ggaaagagag   420
gggcttcagg acattgtgat cgggattatc aagactgtag ctcaacagat ccatggcact   480
gagatagaca tgaaggttat tcagcaaaga agtgaagaat gtgatcatac caattttta   540
attgaagaaa aagaatcaaa agaagaggat ttttatgaag atctggacag gtttgaagag   600
aacggtaccc aggactcccg tatcagcccg tacaccttct gcaaagcgtt tccttttcac   660
atcatatttg accgggacct agtagtcacg cagtgtggaa atgctatcta cagagtgctc   720
ccccagctcc agcctgggaa gtgcagcctt ctgtctgtct tctctctggt ccgccctcat   780
attgacatca gtttccacgg gattctttca cacatcaata ccgtctttgt actgagaagc   840
aaggaagggt tgctggatgt tgagaaactt gaatgtgagg atgaactgac tggggcagag   900
attagctgcc tccgtctcaa aggccaaatg atctatttac cggaagcaga tagcatcctc   960
ttcctctgtt caccaagtgt gatgaacttg gatgacctaa caagaagagg cctgtacctg  1020
agtgacatcc ctctccatga tgctacacga gacctggtcc ttttgggaga acagttccgg  1080
gaggagtaca aactgacaca agagctggaa atcctcacag acaggctgca gctcacactg  1140
agggctttgg aggattga                                                1158

<210> SEQ ID NO 18
<211> LENGTH: 385
<212> TYPE: PRT
<213> ORGANISM: Rattus norvegicus

<400> SEQUENCE: 18

Met Tyr Gly Phe Val Asn His Ala Leu Glu Leu Leu Val Ile Arg Asn
1               5                   10                  15
Tyr Gly Pro Glu Val Trp Glu Asp Ile Lys Lys Glu Ala Gln Leu Asp
                20                  25                  30
```

Glu Gly Gln Phe Leu Val Arg Ile Ile Tyr Asp Asp Ser Lys Thr
    35                  40                  45

Tyr Asp Leu Val Ala Ala Ser Lys Val Leu Asn Leu Asn Ala Gly
 50                  55                  60

Glu Ile Leu Gln Met Phe Gly Lys Met Phe Phe Val Phe Cys Gln Glu
 65                  70                  75                  80

Ser Gly Tyr Asp Thr Ile Leu Arg Val Leu Gly Ser Asn Val Arg Glu
                 85                  90                  95

Phe Leu Gln Asn Leu Asp Ala Leu His Asp His Leu Ala Thr Ile Tyr
                100                 105                 110

Pro Gly Met Arg Ala Pro Ser Phe Arg Cys Thr Asp Ala Glu Lys Gly
             115                 120                 125

Lys Gly Leu Ile Leu His Tyr Tyr Ser Glu Arg Glu Gly Leu Gln Asp
         130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Cys Asp His
                165                 170                 175

Thr Gln Phe Leu Ile Glu Glu Lys Glu Ser Lys Glu Gly Asp Phe Tyr
             180                 185                 190

Glu Asp Leu Asp Arg Phe Glu Glu Asn Gly Thr Gln Asp Ser Arg Ile
                195                 200                 205

Ser Pro Tyr Thr Phe Cys Lys Ala Phe Pro Phe His Ile Ile Phe Asp
     210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
             260                 265                 270

Asn Thr Val Phe Val Leu Arg Ser Lys Glu Gly Leu Leu Asp Val Glu
         275                 280                 285

Lys Leu Glu Cys Glu Asp Glu Leu Thr Gly Ala Glu Ile Ser Cys Leu
290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
             340                 345                 350

Val Leu Leu Gly Glu Gln Phe Arg Glu Glu Tyr Lys Leu Thr Gln Glu
         355                 360                 365

Leu Glu Ile Leu Thr Asp Arg Leu Gln Leu Thr Leu Arg Ala Leu Glu
370                 375                 380

Asp
385

<210> SEQ ID NO 19
<211> LENGTH: 1158
<212> TYPE: DNA
<213> ORGANISM: Rattus norvegicus

<400> SEQUENCE: 19
atgtacggtt ttgtgaacca tgccctggag ctgctggtga tccgcaatta cggtcccgag    60

```
gtgtgggaag acatcaaaaa agaggcgcag ctggatgaag aaggccagtt tcttgtgaga      120
ataatctacg atgattccaa aacctatgac ttggtggctg ctgcgagcaa agtcctcaac      180
ctcaatgctg gtgaaatcct gcagatgttt gggaagatgt ttttcgtctt ctgtcaagag      240
tctggctatg ataccatctt gcgtgtcctg ggatctaatg tcagggagtt tttgcagaac      300
ctcgacgccc tgcacgacca cctcgccacc atctacccag ggatgcgcgc accttccttc      360
cggtgcaccg atgcagaaaa aggcaaaggg ctcattctgc actactactc ggaaagagag      420
gggcttcagg acattgtgat cgggattatc aagactgtag ctcaacagat ccatggcact      480
gagatagaca tgaaggttat tcagcaaaga agtgaagaat gtgatcatac ccaatttta       540 attgaagaaa aagaatcaaa agaagaggat ttttatgaag atctggacag gtttgaagag      600
aacggtaccc aggactcccg tatcagcccg tacaccttct gcaaagcgtt tccttttcac      660
atcatatttg accgggacct agtagtcacg cagtgtggaa atgctatcta cagagtgctc      720
ccccagctcc agcctgggaa gtgcagcctt ctgtctgtct tctctctggt ccgccctcat      780
attgacatca gtttccacgg gattctttca cacatcaata ccgtctttgt actgagaagc      840
aaggaagggt tgctggatgt tgagaaactt gaatgtgagg atgaactgac tggggcagag      900
attagctgcc tccgtctcaa aggccaaatg atctatttac cggaagcaga tagcatcctc      960
ttcctctgtt caccaagtgt gatgaacttg gatgacctaa caagaagagg cctgtacctg     1020
agtgacatcc ctctccatga tgctacacga gacctggtcc ttttgggaga acagttccgg     1080
gaggagtaca aactgacaca agagctggaa atcctcacag acaggctgca gctcacactg     1140
agggctttgg aggattga                                                   1158

<210> SEQ ID NO 20
<211> LENGTH: 385
<212> TYPE: PRT
<213> ORGANISM: Rattus norvegicus

<400> SEQUENCE: 20

Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
                20                  25                  30

Glu Glu Gly Gln Phe Leu Val Arg Ile Ile Tyr Asp Asp Ser Lys Thr
            35                  40                  45

Tyr Asp Leu Val Ala Ala Ala Ser Lys Val Leu Asn Leu Asn Ala Gly
        50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175
```

```
Thr Gln Phe Leu Ile Glu Glu Lys Glu Ser Lys Glu Asp Phe Tyr
        180                 185                 190
Glu Asp Leu Asp Arg Phe Glu Asn Gly Thr Gln Asp Ser Arg Ile
            195                 200                 205
Ser Pro Tyr Thr Phe Cys Lys Ala Phe Pro His Ile Ile Phe Asp
        210                 215                 220
Arg Asp Leu Val Val Thr Gln Cys Gly Asn Ala Ile Tyr Arg Val Leu
225                 230                 235                 240
Pro Gln Leu Gln Pro Gly Lys Cys Ser Leu Leu Ser Val Phe Ser Leu
                245                 250                 255
Val Arg Pro His Ile Asp Ile Ser Phe His Gly Ile Leu Ser His Ile
            260                 265                 270
Asn Thr Val Phe Val Leu Arg Ser Lys Glu Gly Leu Leu Asp Val Glu
        275                 280                 285
Lys Leu Glu Cys Glu Asp Glu Leu Thr Gly Ala Glu Ile Ser Cys Leu
    290                 295                 300
Arg Leu Lys Gly Gln Met Ile Tyr Leu Pro Glu Ala Asp Ser Ile Leu
305                 310                 315                 320
Phe Leu Cys Ser Pro Ser Val Met Asn Leu Asp Leu Thr Arg Arg
                325                 330                 335
Gly Leu Tyr Leu Ser Asp Ile Pro Leu His Asp Ala Thr Arg Asp Leu
            340                 345                 350
Val Leu Leu Gly Glu Gln Phe Arg Glu Glu Tyr Lys Leu Thr Gln Glu
                355                 360                 365
Leu Glu Ile Leu Thr Asp Arg Leu Gln Leu Thr Leu Arg Ala Leu Glu
    370                 375                 380
Asp
385

<210> SEQ ID NO 21
<211> LENGTH: 2229
<212> TYPE: DNA
<213> ORGANISM: Rattus norvegicus

<400> SEQUENCE: 21
atgtatggat tcatcaacac ctgcctgcag tctcttgtga cagagaaatt tggtgaggag      60
acatgggaga agctgaaggc tcctgcagaa gtgcaagatg tcttcatgac ctacaccgtg     120
tatgatgaca tcatcaccat taagctcatc caagaagcct gcaaggttct ggatgtgtcc     180
atggaagcca ttctgaagct ctttggcgaa tacttcttta gttctgtaa gatgtctggc     240 tatgacagga tgctgcggac acttggagga atctcaccg agtttattga aaacctagat     300
gcactccaca gttacctggc actgtcctat caggaaatga acgcaccatc ctttcgagtg     360
gaggaaggag ctgacggggc gatgcttctc cactactact cagacagaca tggtctgtgt     420
cacattgtac caggtatcat tgaagctgtg gccaaggact ctttgacac tgatgtggcc     480 atgagtatcc tggatatgaa cgaagaggtg gaaaggacag ggaagaaaga acatgttgtg     540
tttctggtcg tgcagaaggc tcacagacag ataagaggag caaaggcaag ccggccacaa     600
ggcagtgagg acagccaggc agaccaggag gctctccagg gaacactcct tcggatgaag     660
gagagatatt taaacatccc tgtttgccct ggggagaaat ctcactcaac tgctgtgagg     720
gcatcggtcc tttttggaaa agggcccctc agggacacct tccagcccgt ctatcctgag     780
agactatggg tcgaagagga ggtgttctgt gatgcttttc ctttccacat tgtctttgat     840
```

```
gaagcactaa gggtcaagca agctggagtg aatattcaga agtatgtccc tggaatctta    900
acccagaagt ttgcactaga tgagtatttt tccatcatcc accctcaagt tactttcaac    960
atctccagca tctgcaagtt cattaacagt cagtttgtct tgaagacaag aaaagaaatg   1020
atgcccaaag caaggaagag ccagccgatg ctcaaactcc ggggtcagat gatctggatg   1080
gagtctctga ggtgcatgat cttcatgtgt tccccaaacg tccgcagcct gcaagagctg   1140
gaagagagca agatgcatct ttctgatatc gctccgcacg acacgaccag ggatctcatc   1200
ctcctcaacc agcagaggct ggcagagatg gagctgtcct gccaactgga aaagaagaag   1260
gaggagttgc gtgtcctttc caatcacctg gccatcgaga agaagaagac agagaccttg   1320
ctgtatgcca tgctgcctga acatgtggcc aaccaactca aggagggcag aaaggtggct   1380
gcaggagaat ttgaaacatg tacaatcctt ttcagcgatg ttgtgacatt taccaacatc   1440
tgtgcagcct gtgaacctat ccaaatcgtg aacatgctga attcaatgta ctccaagttt   1500
gacaggttaa ccagtgtcca tgatgtctac aaagtagaaa caatagggga tgcttacatg   1560
gtggtgggtg gagtaccagt acccgttgaa agccatgctc aaagagtcgc caattttgct   1620
ctggggatga gaatttctgc aaaagaagtg atgaatcctg tcactgggga acctatccag   1680
atcagagtgg aatccacac tggaccagtc ttagcaggtg ttgtgggaga caagatgcct   1740
cggtactgct tgtttggtga cactgtaaac acagcctcta ggatggaaag tcacgggctt   1800
cccagcaaag tgcatctgag ccccacagcc cacagagccc tgaaaaacaa agggtttgaa   1860
attgtcagga gaggcgagat cgaagtgaag gggaaaggaa agatgaccac atactttctg   1920
atccagaacc tgaatgccac cgaggatgag ataatgggc gaccttcagc ccccgctgat   1980
gggaaggaag tatgtactcc cggaaaccaa gtcaggaagt cccctgctgt cccgaggaac   2040
acagaccatc agcaacaagt ctacaaagga gacccagcag acgcttctaa tgaagtcaca   2100
cttgctggga gcccagtggc agggcgaaac tccacagatg cagtcaataa ccagccatca   2160
ccagatgaga ccaagacaag tgtcgttgct agtggccctg tgctgtctgc tttctgtgtt   2220
gtgctgtga                                                           2229
```

<210> SEQ ID NO 22
<211> LENGTH: 742
<212> TYPE: PRT
<213> ORGANISM: Rattus norvegicus

<400> SEQUENCE: 22

```
Met Tyr Gly Phe Ile Asn Thr Cys Leu Gln Ser Leu Val Thr Glu Lys
1               5                   10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125
```

```
Leu Leu His Tyr Tyr Ser Asp Arg His Gly Leu Cys His Ile Val Pro
    130                 135                 140

Gly Ile Ile Glu Ala Val Ala Lys Asp Phe Phe Asp Thr Asp Val Ala
145                 150                 155                 160

Met Ser Ile Leu Asp Met Asn Glu Glu Val Glu Arg Thr Gly Lys Lys
                165                 170                 175

Glu His Val Val Phe Leu Val Val Gln Lys Ala His Arg Gln Ile Arg
            180                 185                 190

Gly Ala Lys Ala Ser Arg Pro Gln Gly Ser Glu Asp Ser Gln Ala Asp
        195                 200                 205

Gln Glu Ala Leu Gln Gly Thr Leu Leu Arg Met Lys Glu Arg Tyr Leu
210                 215                 220

Asn Ile Pro Val Cys Pro Gly Glu Lys Ser His Ser Thr Ala Val Arg
225                 230                 235                 240

Ala Ser Val Leu Phe Gly Lys Gly Pro Leu Arg Asp Thr Phe Gln Pro
                245                 250                 255

Val Tyr Pro Glu Arg Leu Trp Val Glu Glu Val Phe Cys Asp Ala
                260                 265                 270

Phe Pro Phe His Ile Val Phe Asp Glu Ala Leu Arg Val Lys Gln Ala
    275                 280                 285

Gly Val Asn Ile Gln Lys Tyr Val Pro Gly Ile Leu Thr Gln Lys Phe
290                 295                 300

Ala Leu Asp Glu Tyr Phe Ser Ile Ile His Pro Gln Val Thr Phe Asn
305                 310                 315                 320

Ile Ser Ser Ile Cys Lys Phe Ile Asn Ser Gln Phe Val Leu Lys Thr
                325                 330                 335

Arg Lys Glu Met Met Pro Lys Ala Arg Lys Ser Gln Pro Met Leu Lys
            340                 345                 350

Leu Arg Gly Gln Met Ile Trp Met Glu Ser Leu Arg Cys Met Ile Phe
        355                 360                 365

Met Cys Ser Pro Asn Val Arg Ser Leu Gln Glu Leu Glu Glu Ser Lys
370                 375                 380

Met His Leu Ser Asp Ile Ala Pro His Asp Thr Thr Arg Asp Leu Ile
385                 390                 395                 400

Leu Leu Asn Gln Gln Arg Leu Ala Glu Met Glu Leu Ser Cys Gln Leu
                405                 410                 415

Glu Lys Lys Lys Glu Glu Leu Arg Val Leu Ser Asn His Leu Ala Ile
            420                 425                 430

Glu Lys Lys Lys Thr Glu Thr Leu Leu Tyr Ala Met Leu Pro Glu His
        435                 440                 445

Val Ala Asn Gln Leu Lys Glu Gly Arg Lys Val Ala Ala Gly Glu Phe
450                 455                 460

Glu Thr Cys Thr Ile Leu Phe Ser Asp Val Val Thr Phe Thr Asn Ile
465                 470                 475                 480

Cys Ala Ala Cys Glu Pro Ile Gln Ile Val Asn Met Leu Asn Ser Met
                485                 490                 495

Tyr Ser Lys Phe Asp Arg Leu Thr Ser Val His Asp Val Tyr Lys Val
            500                 505                 510

Glu Thr Ile Gly Asp Ala Tyr Met Val Val Gly Val Pro Val Pro
        515                 520                 525

Val Glu Ser His Ala Gln Arg Val Ala Asn Phe Ala Leu Gly Met Arg
530                 535                 540
```

```
Ile Ser Ala Lys Glu Val Met Asn Pro Val Thr Gly Glu Pro Ile Gln
545                 550                 555                 560

Ile Arg Val Gly Ile His Thr Gly Pro Val Leu Ala Gly Val Val Gly
                565                 570                 575

Asp Lys Met Pro Arg Tyr Cys Leu Phe Gly Asp Thr Val Asn Thr Ala
            580                 585                 590

Ser Arg Met Glu Ser His Gly Leu Pro Ser Lys Val His Leu Ser Pro
        595                 600                 605

Thr Ala His Arg Ala Leu Lys Asn Lys Gly Phe Glu Ile Val Arg Arg
    610                 615                 620

Gly Glu Ile Glu Val Lys Gly Lys Gly Lys Met Thr Thr Tyr Phe Leu
625                 630                 635                 640

Ile Gln Asn Leu Asn Ala Thr Glu Asp Glu Ile Met Gly Arg Pro Ser
                645                 650                 655

Ala Pro Ala Asp Gly Lys Glu Val Cys Thr Pro Gly Asn Gln Val Arg
            660                 665                 670

Lys Ser Pro Ala Val Pro Arg Asn Thr Asp His Gln Gln Val Tyr
        675                 680                 685

Lys Gly Asp Pro Ala Asp Ala Ser Asn Glu Val Thr Leu Ala Gly Ser
690                 695                 700

Pro Val Ala Gly Arg Asn Ser Thr Asp Ala Val Asn Asn Gln Pro Ser
705                 710                 715                 720

Pro Asp Glu Thr Lys Thr Ser Val Val Ala Ser Gly Pro Val Leu Ser
                725                 730                 735

Ala Phe Cys Val Val Leu
            740

<210> SEQ ID NO 23
<211> LENGTH: 19
<212> TYPE: PRT
<213> ORGANISM: Artificial Sequence
<220> FEATURE:
<223> OTHER INFORMATION: Synthetic Construct

<400> SEQUENCE: 23

Cys Ala Ala Thr Cys Gly Ala Gly Ala Cys Cys Thr Gly Gly Thr
1               5                   10                  15

Gly Gly Ala

<210> SEQ ID NO 24
<211> LENGTH: 18
<212> TYPE: PRT
<213> ORGANISM: Artificial Sequence
<220> FEATURE:
<223> OTHER INFORMATION: Synthetic Construct

<400> SEQUENCE: 24

Gly Cys Ala Cys Ala Cys Ala Cys Thr Cys Cys Ala Gly Gly Cys Cys
1               5                   10                  15

Cys Thr

<210> SEQ ID NO 25
<211> LENGTH: 19
<212> TYPE: PRT
<213> ORGANISM: Artificial Sequence
<220> FEATURE:
<223> OTHER INFORMATION: Synthetic Construct

<400> SEQUENCE: 25
```

```
Cys Ala Ala Cys Cys Ala Gly Ala Cys Ala Thr Gly Gly Gly Thr Cys
1               5                   10                  15

Cys Ala Cys
```

<210> SEQ ID NO 26
<211> LENGTH: 21
<212> TYPE: PRT
<213> ORGANISM: Artificial Sequence
<220> FEATURE:
<223> OTHER INFORMATION: Synthetic Construct

<400> SEQUENCE: 26

```
Gly Thr Thr Ala Ala Cys Gly Ala Ala Ala Gly Gly Cys Cys Cys
1               5                   10                  15

Ala Cys Ala Gly Ala
            20
```

<210> SEQ ID NO 27
<211> LENGTH: 21
<212> TYPE: PRT
<213> ORGANISM: Artificial Sequence
<220> FEATURE:
<223> OTHER INFORMATION: Synthetic Construct

<400> SEQUENCE: 27

```
Gly Thr Thr Gly Thr Gly Gly Ala Thr Cys Cys Ala Gly Thr Cys Ala
1               5                   10                  15

Cys Cys Thr Cys Thr
            20
```

<210> SEQ ID NO 28
<211> LENGTH: 21
<212> TYPE: PRT
<213> ORGANISM: Artificial Sequence
<220> FEATURE:
<223> OTHER INFORMATION: Synthetic Construct

<400> SEQUENCE: 28

```
Gly Ala Thr Thr Cys Thr Cys Ala Gly Thr Gly Thr Gly Cys Thr Gly
1               5                   10                  15

Gly Thr Cys Ala Cys
            20
```

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

```
Cys Ala Ala Gly Gly Ala Gly Gly Ala Ala Gly Cys Thr Thr Ala Thr
1               5                   10                  15

Cys Thr Ala Thr Gly Ala Ala
            20
```

<210> SEQ ID NO 30
<211> LENGTH: 22
<212> TYPE: PRT
<213> ORGANISM: Artificial Sequence
<220> FEATURE:
<223> OTHER INFORMATION: Synthetic Construct

<400> SEQUENCE: 30

-continued

```
Ala Thr Thr Thr Gly Ala Cys Gly Ala Ala Gly Gly Cys Gly Ala Ala
1               5                   10                  15

Gly Ala Ala Gly Cys Thr
            20
```